US010336782B2

(12) United States Patent
Koiso et al.

(10) Patent No.: US 10,336,782 B2
(45) Date of Patent: Jul. 2, 2019

(54) SUBSTITUTED CYCLOPENTADIENYL COBALT COMPLEX AND METHOD FOR PRODUCTION THEREOF, AND COBALT-CONTAINING THIN FILM AND METHOD FOR PRODUCTION THEREOF

(71) Applicants: TOSOH CORPORATION, Shunan-shi, Yamaguchi (JP); SAGAMI CHEMICAL RESEARCH INSTITUTE, Ayase-shi, Kanagawa (JP)

(72) Inventors: Naoyuki Koiso, Ayase (JP); Yuki Yamamoto, Ayase (JP); Hiroyuki Oike, Ayase (JP); Teppei Hayakawa, Ayase (JP); Taishi Furukawa, Ayase (JP); Ken-ichi Tada, Ayase (JP)

(73) Assignee: SAGAMI CHEMICAL RESEARCH INSTITUTE, Ayase-shi, Kanagawa (JP)

( * ) Notice: Subject to any disclaimer, the term of this patent is extended or adjusted under 35 U.S.C. 154(b) by 0 days.

(21) Appl. No.: 16/061,049

(22) PCT Filed: Dec. 12, 2016

(86) PCT No.: PCT/JP2016/086932
§ 371 (c)(1),
(2) Date: Jun. 11, 2018

(87) PCT Pub. No.: WO2017/104619
PCT Pub. Date: Jun. 22, 2017

(65) Prior Publication Data
US 2018/0362568 A1   Dec. 20, 2018

(30) Foreign Application Priority Data

Dec. 16, 2015 (JP) .................................. 2015-245678
Jun. 30, 2016 (JP) .................................. 2016-129885
Oct. 18, 2016 (JP) .................................. 2016-204107

(51) Int. Cl.
*C07F 15/06* (2006.01)
*C07F 17/00* (2006.01)
(Continued)

(52) U.S. Cl.
CPC ............... *C07F 17/02* (2013.01); *C07F 15/06* (2013.01); *C07F 17/00* (2013.01); *C07F 19/00* (2013.01);
(Continued)

(58) Field of Classification Search
CPC ......... H01L 21/28518; H01L 21/02175; H01L 21/02271; H01L 21/28097; H01L 29/4975;
(Continued)

(56) References Cited

U.S. PATENT DOCUMENTS

| 5,245,064 A * | 9/1993 | Gassman | .............. C07C 22/02 |
| | | | 526/943 |
| 6,743,935 B2 * | 6/2004 | Salzer | .............. C07F 15/0046 |
| | | | 549/512 |

(Continued)

FOREIGN PATENT DOCUMENTS

| JP | 09-235287 | 9/1997 |
| JP | 2010-528183 | 8/2010 |

(Continued)

OTHER PUBLICATIONS

International Search Report for PCT/JP2016/086932, dated Jan. 24, 2017, 4 pages.

(Continued)

*Primary Examiner* — Victor A Mandala
(74) *Attorney, Agent, or Firm* — Nixon & Vanderhye P.C.

(57) ABSTRACT

Provided is a cobalt complex which is useful for the production of a cobalt-containing thin film under conditions where no oxidizing gas is used. A cobalt complex repre- (Continued)

sented by general formula (1) (wherein $R^1$ represents a silyloxy group represented by general formula (2) (wherein $R^6$, $R^7$ and $R^8$ independently represent an alkyl group having 1 to 6 carbon atoms); $R^2$ represents a hydrogen atom, an alkyl group having 1 to 6 carbon atoms, or a silyloxy group represented by general formula (2); $R^3$, $R^4$ and $R^5$ independently represent a hydrogen atom or an alkyl group having 1 to 6 carbon atoms; and L represents a diene having 4 to 10 carbon atoms) is used.

11 Claims, 1 Drawing Sheet

(51) Int. Cl.
    *C07F 17/02*     (2006.01)
    *C07F 19/00*     (2006.01)
    *C23C 16/18*     (2006.01)
    *H01L 21/02*     (2006.01)
    *H01L 21/28*     (2006.01)
    *H01L 29/45*     (2006.01)
    *H01L 29/49*     (2006.01)
    *H01L 21/285*     (2006.01)
    *H01L 21/768*     (2006.01)
    *H01L 23/532*     (2006.01)

(52) U.S. Cl.
    CPC ........ *C23C 16/18* (2013.01); *H01L 21/02175* (2013.01); *H01L 21/02271* (2013.01); *H01L 21/28* (2013.01); *H01L 21/285* (2013.01); *H01L 21/28097* (2013.01); *H01L 21/28518* (2013.01); *H01L 21/28556* (2013.01); *H01L 21/76889* (2013.01); *H01L 23/53238* (2013.01); *H01L 29/456* (2013.01); *H01L 29/4975* (2013.01)

(58) Field of Classification Search
    CPC ......... H01L 21/28556; H01L 21/76889; H01L 29/456; H01L 23/53238; H01L 21/285; H01L 21/28; C07F 17/02; C07F 15/06; C07F 19/00; C07F 17/00; C23C 16/18
    See application file for complete search history.

(56) References Cited

U.S. PATENT DOCUMENTS 9,381,506 B2 *   7/2016   Diao ..................... C07F 15/06
2018/0036724 A1 *   2/2018   Dash ..................... C07F 15/02

FOREIGN PATENT DOCUMENTS

JP     2016-147819     8/2016
WO     2015/190420     12/2015

OTHER PUBLICATIONS

Sisak: "Silylations of alpha, beta-unsaturated and aromatic carbonyl compounds with cobalt carbonyls", Journal of Organometallic Chemistry, vol. 586, No. 1, 1999, pp. 48-53, XP004177514.

* cited by examiner

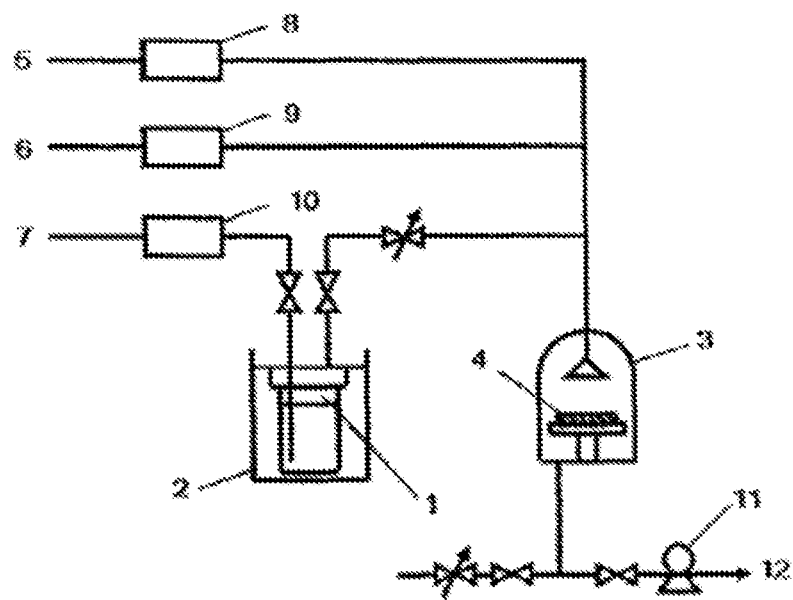

SUBSTITUTED CYCLOPENTADIENYL COBALT COMPLEX AND METHOD FOR PRODUCTION THEREOF, AND COBALT-CONTAINING THIN FILM AND METHOD FOR PRODUCTION THEREOF

This application is the U.S. national phase of International Application No. PCT/JP2016/086932 filed Dec. 12, 2016, which designated the U.S. and claims priority to JP Patent Application No. 2015-245678 filed Dec. 16, 2015, JP Patent Application No. 2016-129885 filed Jun. 30, 2016, and JP Patent Application No. 2016-204107 filed Oct. 18, 2016, the entire contents of each of which are hereby incorporated by reference.

TECHNICAL FIELD

The present invention relates to a cobalt complex useful as a raw material in the manufacture of semiconductor elements and a production method therefor, and cobalt-containing thin film produced using this cobalt complex and a production method therefor.

BACKGROUND ART

Because cobalt has high conductivity and a high work function, can form a conductive silicide, and has excellent lattice matching with copper, it has gathered attention as a raw material for gate electrodes in semiconductor elements such as transistors, for contacts on diffusion layers in source-drain sections, and for copper wiring sheet layers/liner layers. In next-generation semiconductor elements, highly miniaturized three-dimensional designs are being used to further improve memory capacity and responsiveness. Therefore, in order to use cobalt as a material in next-generation semiconductor elements, a technique is needed to form a cobalt-containing thin film evenly on a three-dimensional substrate to a thickness ranging from several nanometers to tens nanometers. As a technique for preparing a metal thin film on a three-dimensional substrate, utilization of vapor phase deposition method based on chemical reaction such as atomic layer deposition method (ALD method) or chemical vapor deposition method (CVD method) is strongly expected. $CoSi_2$ obtained by forming a cobalt film and then subjecting the film to silicidation is being considered as gate electrodes and as contacts on diffusion layers in the source-drain sections of next-generation semiconductor elements. When cobalt is used as a copper wiring sheet layer/liner layer, a barrier metal such as titanium nitride or tantalum nitride is expected to be used underneath. When silicon or a barrier metal is oxidized in the production of a cobalt-containing thin film, problems such as poor conduction with the transistor due to an increase in the resistance value occur. In order to avoid this problem, there is a demand for a material that enables fabrication of a cobalt-containing thin film under the condition that no oxidizing gas such as oxygen or ozone is used as the decomposition gas.

Non-Patent Documents 1 and 2 mention dicarbonyl [$\eta^5$-(1-diethylmethylsilyloxy-2,3,4,5-tetraphenyl)cyclopentadienyl]cobalt and dicarbonyl[$\eta^5$-(1-dimethyl(phenyl)silyloxy-3,4-diphenyl-2,5-dimethyl(phenyl)silyl)cyclopentadienyl]cobalt as compounds having a structure resembling a cobalt complex (1) of the present invention from the viewpoint of having an $\eta^5$-silyloxycyclopentadienyl ligand, but these differ from a cobalt complex of the present invention from the viewpoint of having a phenyl group. Also, neither of these documents mentions the use of these complexes as a material in the production of a cobalt-containing thin film.

PRIOR ART DOCUMENTS

Non-Patent Documents

Non-Patent Document 1: Journal of Organometallic Chemistry, Vol. 586, p. 48 (1999)
Non-Patent Document 2: Organometallics, Vol. 33, p. 5622, Supporting Information (2014)

SUMMARY OF THE INVENTION

Problem to be Solved by the Invention

An object of the present invention is to provide a cobalt complex that is useful as a raw material in the production of a cobalt-containing thin film under conditions in which no oxidizing gas is used.

Means for Solving the Problem

As a result of conducting extensive research to solve this problem, the present inventors discovered that a cobalt complex represented by Formula (1) was a useful material for the production of a cobalt-containing thin film under conditions in which no oxidizing gas is used, that is, under conditions in which a reducing gas is used.

The following is a summary of the present invention.

(1) A cobalt complex represented by Formula (1)

[Formula 1]

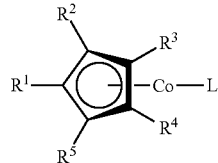

(1)

[where $R^1$ is a silyloxy group represented by Formula (2)

[Formula 2]

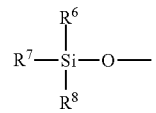

(2)

(where $R^6$, $R^7$ and $R^8$ each independently represent an alkyl group having from 1 to 6 carbon atoms); $R^2$ is a hydrogen atom, an alkyl group having from 1 to 6 carbon atoms, or a silyloxy group represented by Formula (2); $R^3$, $R^4$ and $R^5$ each independently represent a hydrogen atom or an alkyl group having from 1 to 6 carbon atoms; and L is a diene having from 4 to 10 carbon atoms].

(2) A cobalt complex according to (1), wherein $R^3$, $R^4$ and $R^5$ are each independently a hydrogen atom or a methyl group.

(3) A cobalt complex according to (1) or (2), wherein $R^6$, $R^7$ and $R^8$ are each independently an alkyl group having from 1 to 4 carbon atoms.

(4) A method for producing a cobalt complex according to any of (1) to (3), the method comprising the steps of: reacting a trisphosphine complex represented by Formula (3)

[Formula 3]

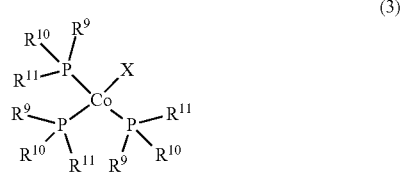

(3)

(where $R^9$, $R^{10}$ and $R^{11}$ are each independently a phenyl group, a tolyl group, an alkyl group having from 1 to 6 carbon atoms, or an alkyloxy group having from 1 to 6 carbon atoms; and X is a halogen atom) with a lithium cyclopentadienide represented by Formula (4)

[Formula 4]

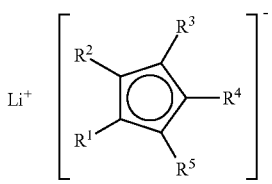

(4)

(where $R^1$, $R^2$, $R^3$, $R^4$ and $R^5$ are the same as $R^1$, $R^2$, $R^3$, $R^4$ and $R^5$ in Formula (1)); and reacting the product with a diene having from 4 to 10 carbon atoms.

(5) A method for producing a cobalt-containing thin film using, as a raw material in a vapor phase deposition method based on a chemical reaction, a cobalt complex represented by Formula (1)

[Formula 5]

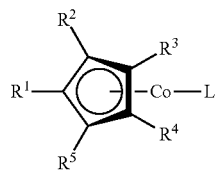

(1)

[where $R^1$ is a silyloxy group represented by Formula (2)

[Formula 6]

(2)

(where $R^6$, $R^7$ and $R^8$ each independently represent an alkyl group having from 1 to 6 carbon atoms); $R^2$ is a hydrogen atom, an alkyl group having from 1 to 6 carbon atoms, or a silyloxy group represented by Formula (2); $R^3$, $R^4$ and $R^5$ each independently represent a hydrogen atom or an alkyl group having from 1 to 6 carbon atoms; and L is a diene having from 4 to 10 carbon atoms].

(6) A method for producing a cobalt-containing thin film according to (5), wherein the vapor phase deposition method based on a chemical reaction is the chemical vapor phase deposition method.

(7) A method for producing a cobalt-containing thin film according to (5) or (6), wherein a decomposition gas is used in the vapor phase deposition method based on a chemical reaction.

(8) A method for producing a cobalt-containing thin film according to (7), wherein a reductive gas is used as the decomposition gas.

(9) A method for producing a cobalt-containing thin film according to any of (5) to (8), wherein the cobalt-containing thin film is a metal cobalt thin film.

(10) A cobalt-containing thin film produced using a method for producing a cobalt-containing thin film according to any of (5) to (9).

(11) A semiconductor device using a cobalt-containing thin film according to (10) as at least one of a transistor gate electrode, a contact on a diffusion layer in a source-drain section, and a copper wiring sheet layer/liner layer.

Effect of the Invention

A cobalt-containing thin film can be produced under conditions in which a reducing gas is used as a reaction gas by using a cobalt complex (1) of the present invention as a raw material.

BRIEF DESCRIPTION OF THE DRAWINGS

FIG. 1 is a diagram showing the CVD device used in Examples 8, 9 and 16-33 and in Comparative Example 1.

MODE FOR CARRYING OUT THE INVENTION

The following is a more detailed description of the present invention. First, the definition of $R^1$, $R^2$, $R^3$, $R^4$, $R^5$, $R^6$, $R^7$ and $R^8$ in Formulas (1) and (2) will be explained.

$R^1$ is a silyloxy group represented by Formula (2), and $R^2$ may be a hydrogen atom, an alkyl group having from 1 to 6 carbon atoms, or a silyloxy group represented by Formula (2). $R^3$, $R^4$ and $R^5$ may be a hydrogen atom or an alkyl group having from 1 to 6 carbon atoms.

The alkyl groups having from 1 to 6 carbon atoms that are represented by $R^6$, $R^7$ and $R^8$ in Formula (2) may be linear, branched or cyclic. Specific examples include a methyl group, ethyl group, propyl group, isopropyl group, cyclopropyl group, butyl group, isobutyl group, sec-butyl group, tert-butyl group, cyclobutyl group, pentyl group, 1-ethylpropyl group, 1-methylbutyl group, 2-methylbutyl group, isopentyl group, neopentyl group, tert-pentyl group, cyclopentyl group, cyclobutylmethyl group, hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, cyclohexyl group, cyclopentylmethyl group, 1-cyclobutylethyl group, and 2-cyclobutylethyl group. In view of the fact that the cobalt complex (1) of the present invention has vapor pressure and thermal stability suitable for CVD material and ALD material, $R^6$, $R^7$ and $R^8$ are preferably an alkyl group having from 1 to 4 carbon atoms, and more preferably a methyl group, ethyl group or tert-butyl group.

The following are specific examples of a silyloxy group represented by Formula (2).

[Formula 7]

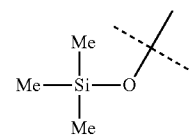
(2-1)

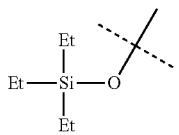
(2-2)

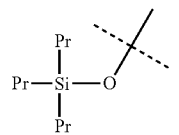
(2-3)

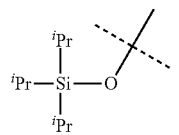
(2-4)

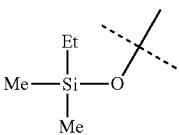
(2-5)

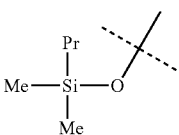
(2-6)

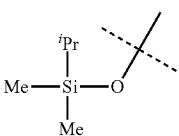
(2-7)

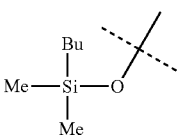
(2-8)

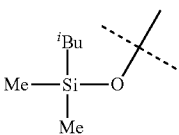
(2-9)

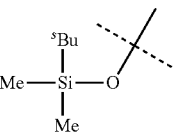
(2-10)

-continued

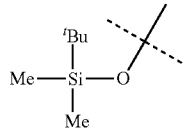
(2-11)

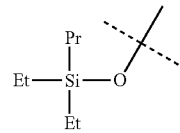
(2-12)

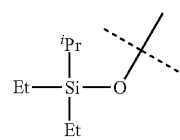
(2-13)

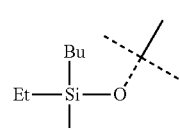
(2-14)

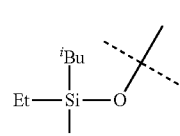
(2-15)

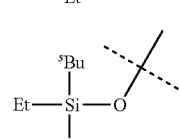
(2-16)

(2-17)

In the present specification, Me, Et, Pr, $^i$Pr, Bu, $^i$Bu, $^s$Bu and $^t$Bu represent, respectively, methyl group, ethyl group, propyl group, isopropyl group, butyl group, isobutyl group, sec-butyl group, and tert-butyl group.

The silyloxy group represented by $R^1$ is preferably (2-1), (2-2), (2-5) or (2-11) and more preferably (2-1).

The alkyl group having from 1 to 6 carbon atoms that is represented by $R^2$ may be linear, branched or cyclic. Specific examples include a methyl group, ethyl group, propyl group, isopropyl group, cyclopropyl group, butyl group, isobutyl group, sec-butyl group, tert-butyl group, cyclobutyl group, pentyl group, 1-ethylpropyl group, 1-methylbutyl group, 2-methylbutyl group, isopentyl group, neopentyl group, tert-pentyl group, cyclopentyl group, cyclobutylmethyl group, hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, cyclohexyl group, cyclopentylmethyl group, 1-cyclobutylethyl group, and 2-cyclobutylethyl group.

In view of the fact that the cobalt complex (1) of the present invention has vapor pressure and thermal stability suitable for CVD material and ALD material, $R^2$ is preferably a hydrogen atom, an alkyl group having from 1 to 4 carbon atoms or a silyloxy group represented by (2-1), (2-2), (2-5) or (2-11), more preferably a hydrogen atom, a methyl group, an ethyl group, (2-1), (2-2) or (2-11), and even more preferably a hydrogen atom, a methyl group or (2-1).

The alkyl group having from 1 to 6 carbon atoms that is represented by $R^3$, $R^4$ and $R^5$ may be linear, branched or cyclic. Specific examples include a methyl group, ethyl group, propyl group, isopropyl group, cyclopropyl group, butyl group, isobutyl group, sec-butyl group, tert-butyl group, cyclobutyl group, pentyl group, 1-ethylpropyl group, 1-methylbutyl group, 2-methylbutyl group, isopentyl group, neopentyl group, tert-pentyl group, cyclopentyl group, cyclobutylmethyl group, hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, cyclohexyl group, cyclopentylmethyl group, 1-cyclobutylethyl group and 2-cyclobutylethyl group.

In view of the fact that the cobalt complex (1) of the present invention has vapor pressure and thermal stability suitable for CVD material and ALD material, $R^3$, $R^4$ and $R^5$ is preferably a hydrogen atom or an alkyl group having from 1 to 4 carbon atoms, more preferably a hydrogen atom, methyl group, ethyl group, propyl group, isopropyl group, butyl group, isobutyl group, sec-butyl group, or tert-butyl group, even more preferably a hydrogen atom, methyl group, or tert-butyl group, and still more preferably a hydrogen atom or a methyl group.

The following is a description of the dienes having from 4 to 10 carbon atoms that are represented by L. A diene represented by L may be a linear diene or a cyclic diene.

The linear dienes among the dienes having from 4 to 10 carbon atoms that are represented by L can be any linear diene able to coordinate with cobalt in the s-cis type $\eta^4$ bonding mode. Examples include buta-1,3-diene (butadiene), 2-methylbuta-1,3-diene (isoprene), 2,3-dimethylbuta-1,3-diene, 2-methylpenta-1,3-diene, 2,3-dimethylpenta-1,3-diene, penta-1,3-diene, hexa-2,4-diene, 3-methylpenta-1,3-diene, 3-methylene-pent-1-ene, hexa-1,3-diene, hepta-1,3-diene, octa-1,3-diene, nona-1,3-diene, deca-1,3-diene, 4-methyl-3-methylene-pent-1-ene, and 2-cyclohexyl-1,3-butadiene.

The cyclic dienes among the dienes having from 4 to 10 carbon atoms that are represented by L can be any cyclic diene able to coordinate with cobalt in the s-cis type $\eta^4$ bonding mode or $\eta^2:\eta^2$ bonding mode. Examples include cyclohexa-1,3-diene, methylcyclohexa-1,3-diene, ethylcyclohexa-1,3-diene, propylcyclohexa-1,3-diene, isopropylcyclohexa-1,3-diene, butylcyclohexa-1,3-diene, isobutylcyclohexa-1,3-diene, sec-butylcyclohexa-1,3-diene, tert-butylcyclohexa-1,3-diene, pentylcyclohexa-1,3-diene, hexylcyclohexa-1,3-diene, cyclohexylcyclohexa-1,3-diene, α-phellandrene, α-terpinene, γ-terpinene, norbornadiene, 1,5-cyclooctadiene, and dimethyl-1,5-cyclooctadiene.

In view of the fact that the cobalt complex (1) of the present invention has vapor pressure and thermal stability suitable for CVD material and ALD material, the diene represented by L is preferably a diene having from 4 to 8 carbon atoms, and more preferably butadiene, isoprene, 2,3-dimethylbuta-1,3-diene, 2-methylpenta-1,3-diene, cyclohexa-1,3-diene, norbornadiene, and 1,5-cyclooctadiene.

The following are specific examples of cobalt complexes (1) of the present invention.

[Formula 8]

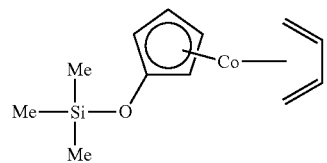
(1-1)

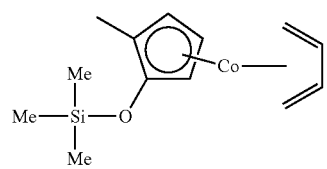
(1-2)

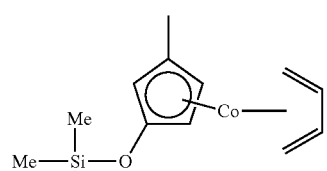
(1-3)

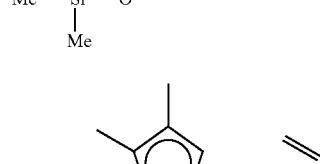
(1-4)

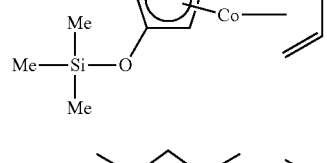
(1-5)

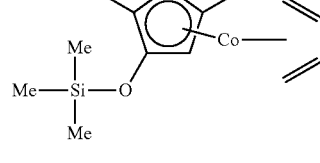
(1-6)

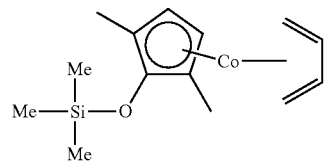
(1-7)

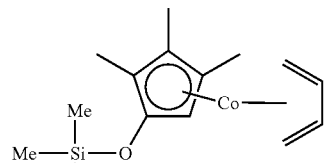
(1-8)

(1-9)
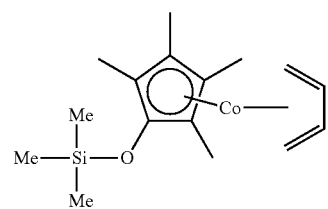
(1-10)
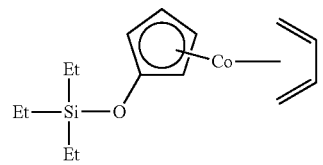
(1-11)
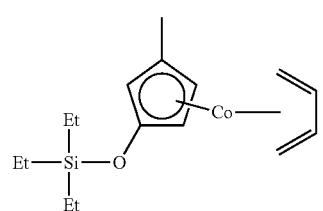
(1-12)
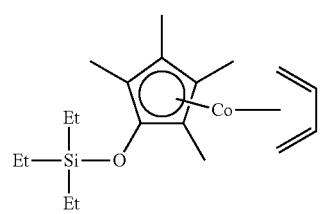
(1-13)
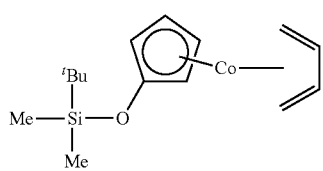
(1-14)
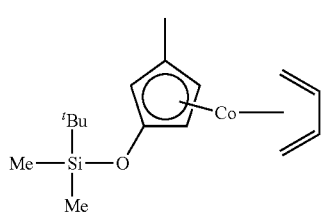
(1-15)
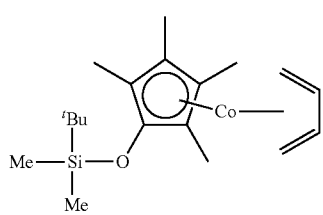
(1-16)
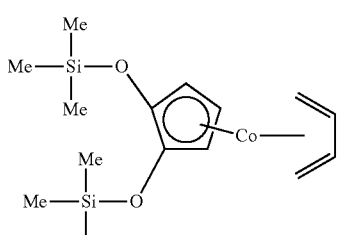
(1-17)
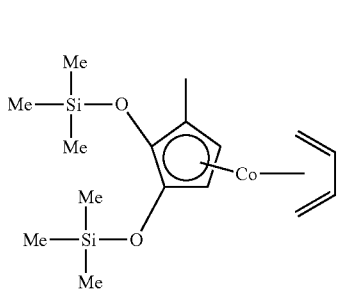
(1-18)
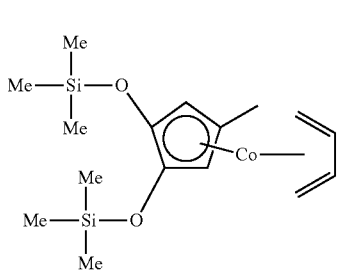
[Formula 9]
(1-19)
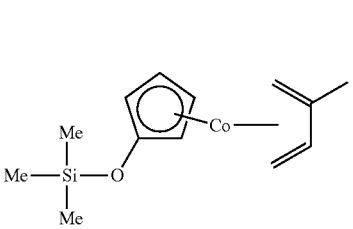
(1-20)
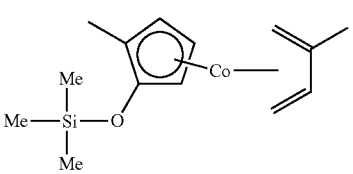
(1-21)
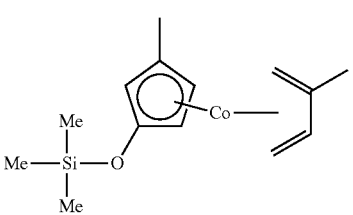

-continued
(1-22)
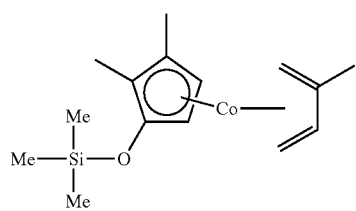
(1-23)
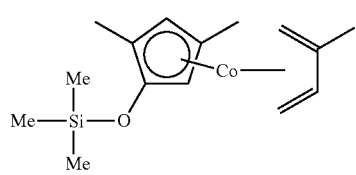
(1-24)
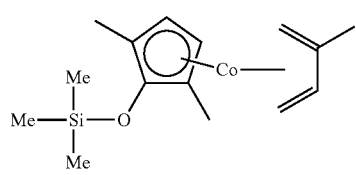
(1-25)
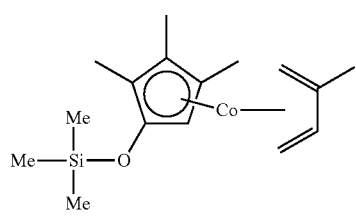
(1-26)
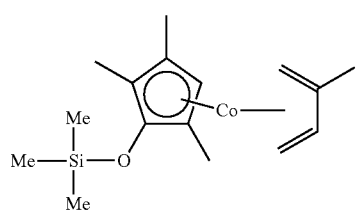
(1-27)
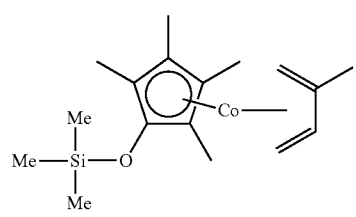
(1-28)
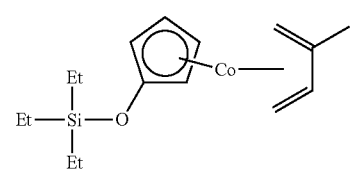
(1-29)
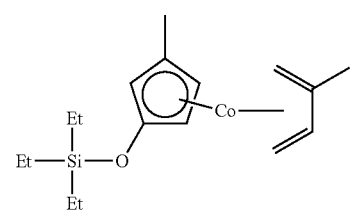
-continued
(1-30)
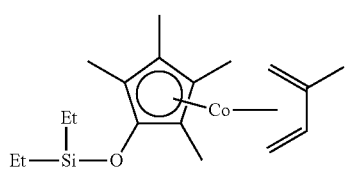
(1-31)
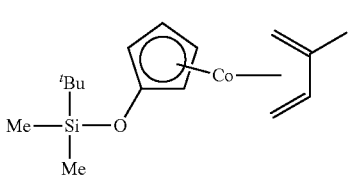
(1-32)
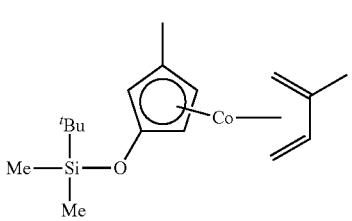
(1-33)
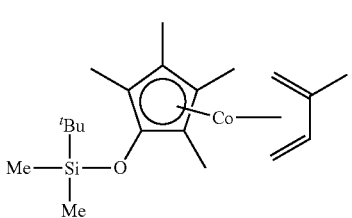
(1-34)
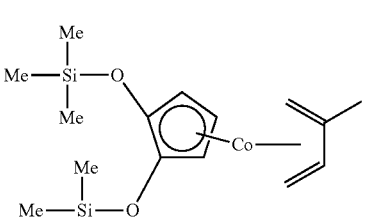
(1-35)
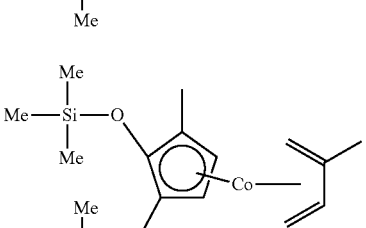
(1-36)
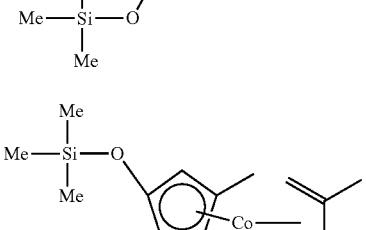

[Formula 10]
(1-37) 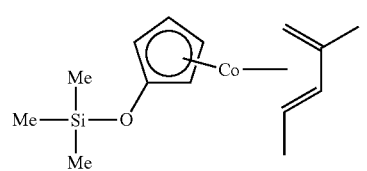
(1-38) 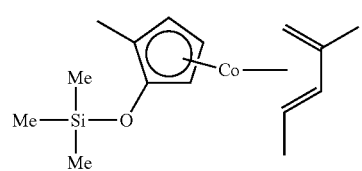
(1-39) 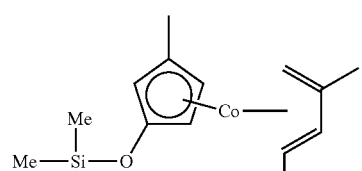
(1-40) 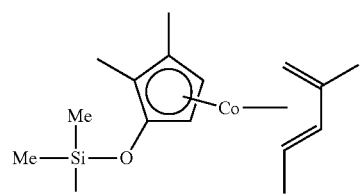
(1-41) 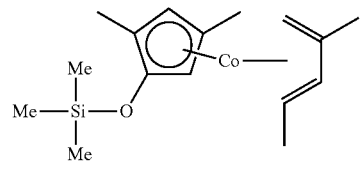
(1-42) 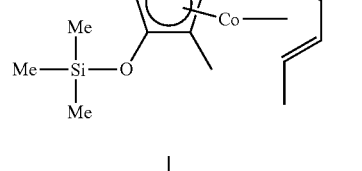
(1-43) 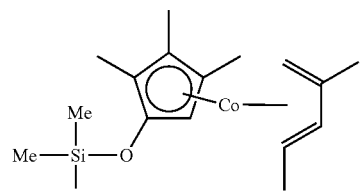
(1-44) 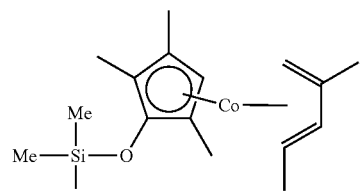
-continued
(1-45) 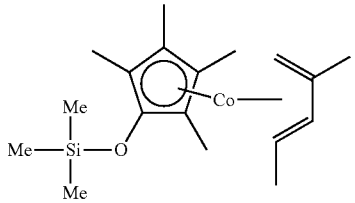
(1-46) 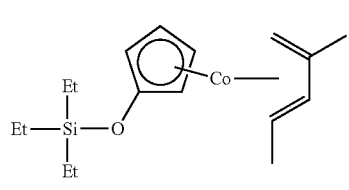
(1-47) 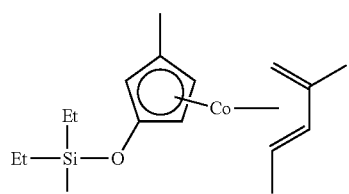
(1-48) 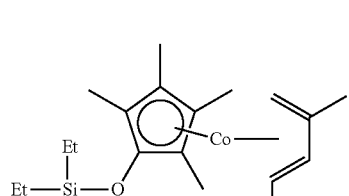
(1-49) 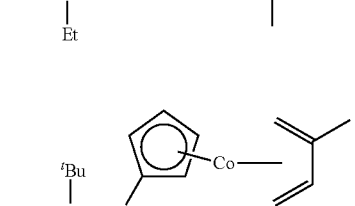
(1-50) 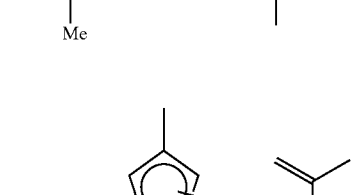
(1-51) 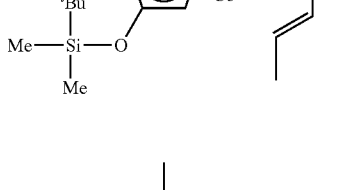

(1-52)
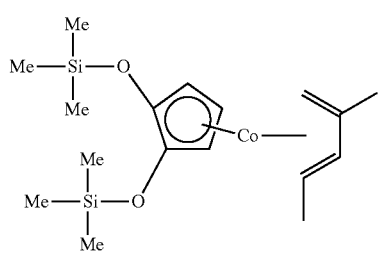
(1-53)
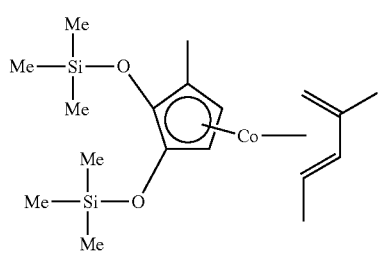
(1-54)
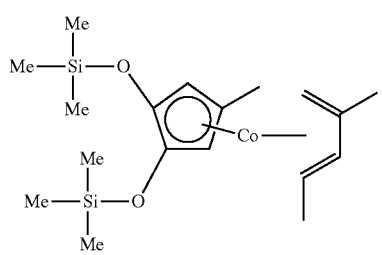
[Formula 11]
(1-55)
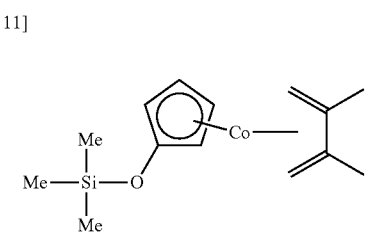
(1-56)
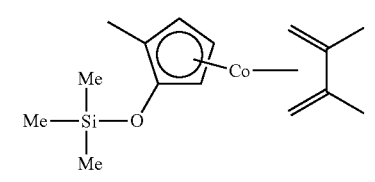
(1-57)
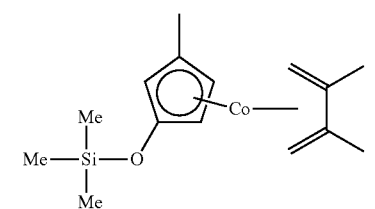
(1-58)
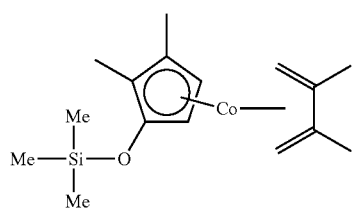
(1-59)
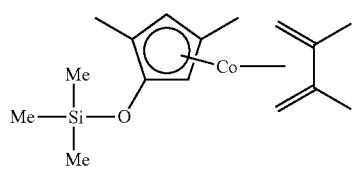
(1-60)
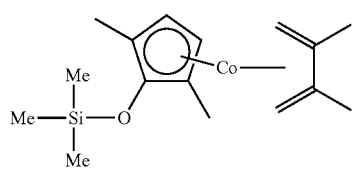
(1-61)
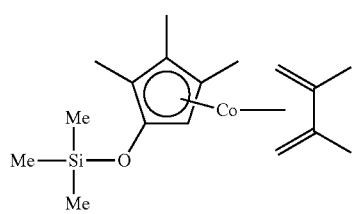
(1-62)
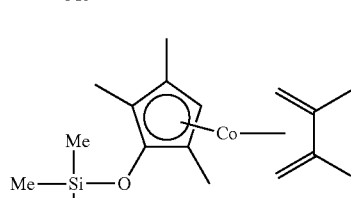
(1-63)
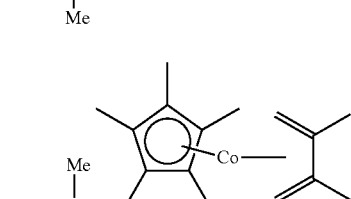
(1-64)
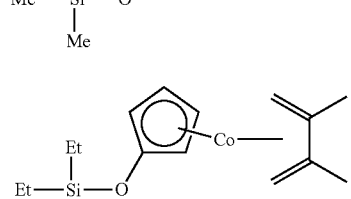
(1-65)
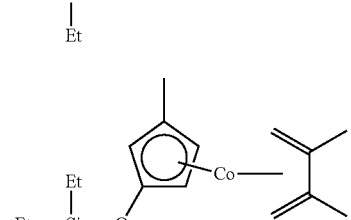

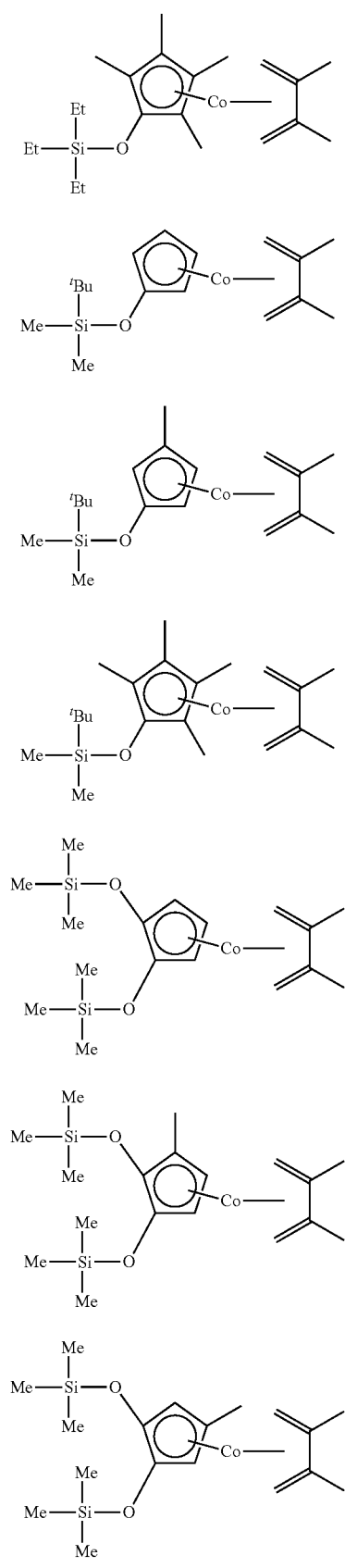
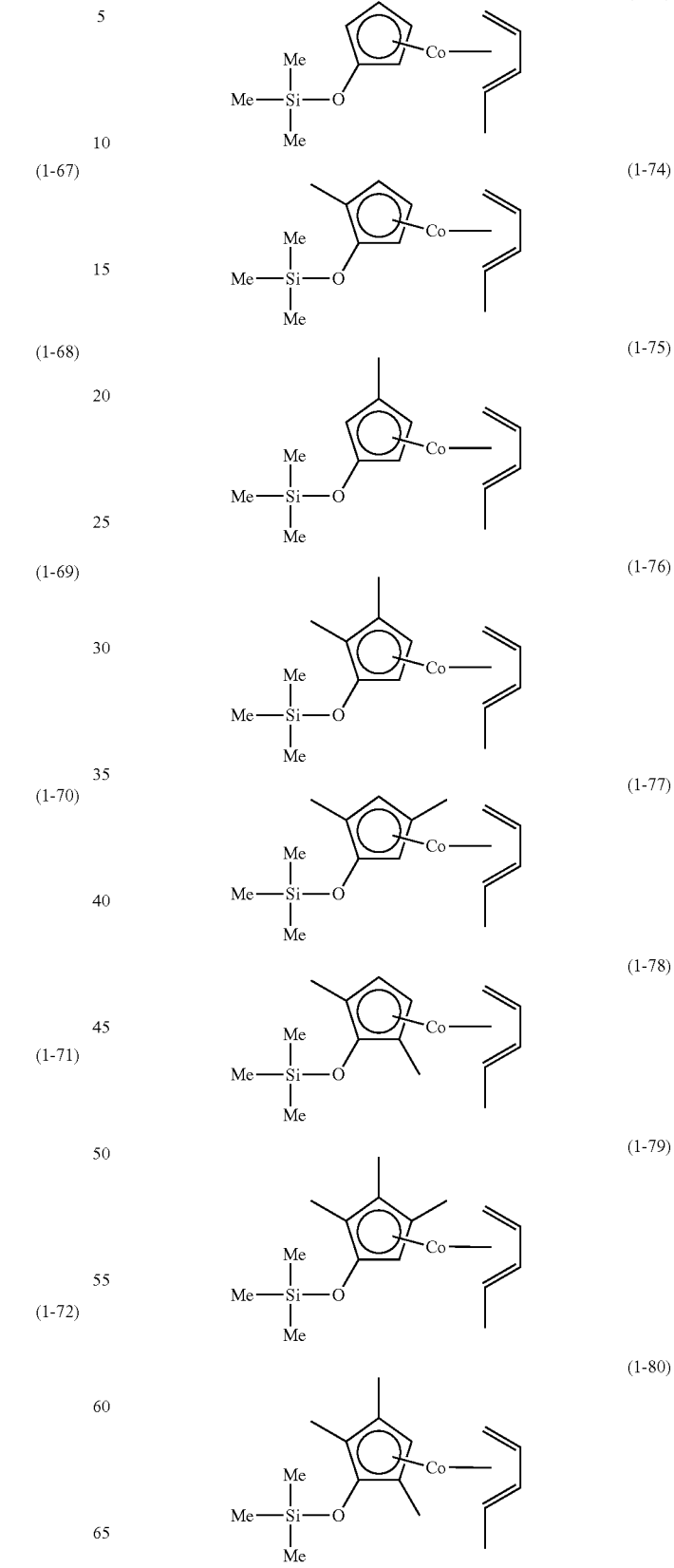

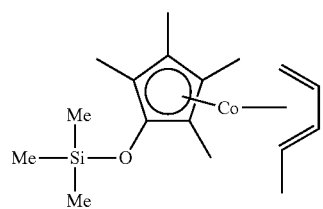 (1-81)
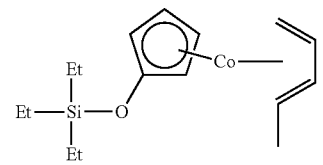 (1-82)
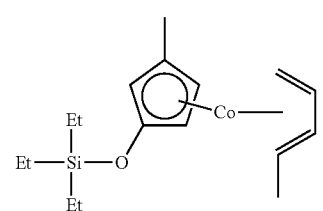 (1-83)
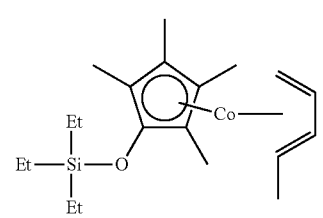 (1-84)
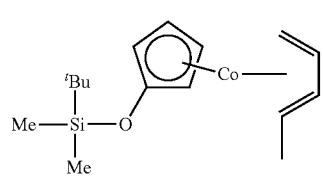 (1-85)
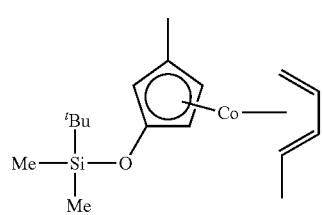 (1-86)
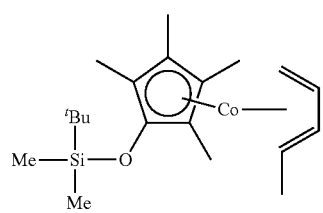 (1-87)
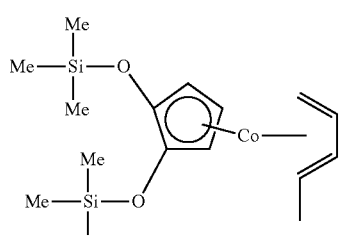 (1-89)
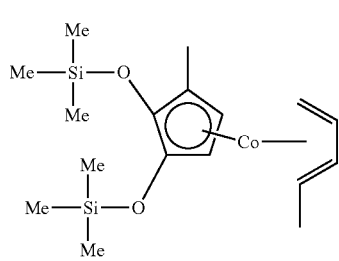 (1-90)
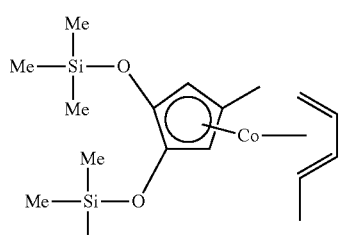 (1-91)
[Formula 13]
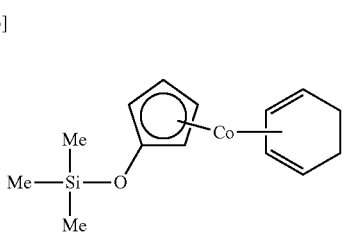 (1-92)
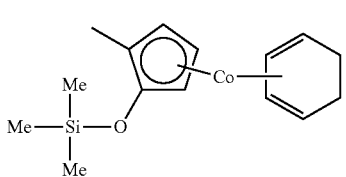 (1-93)
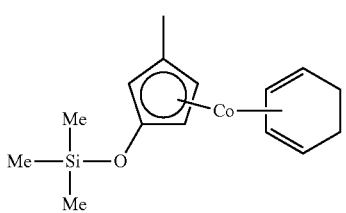 (1-94)

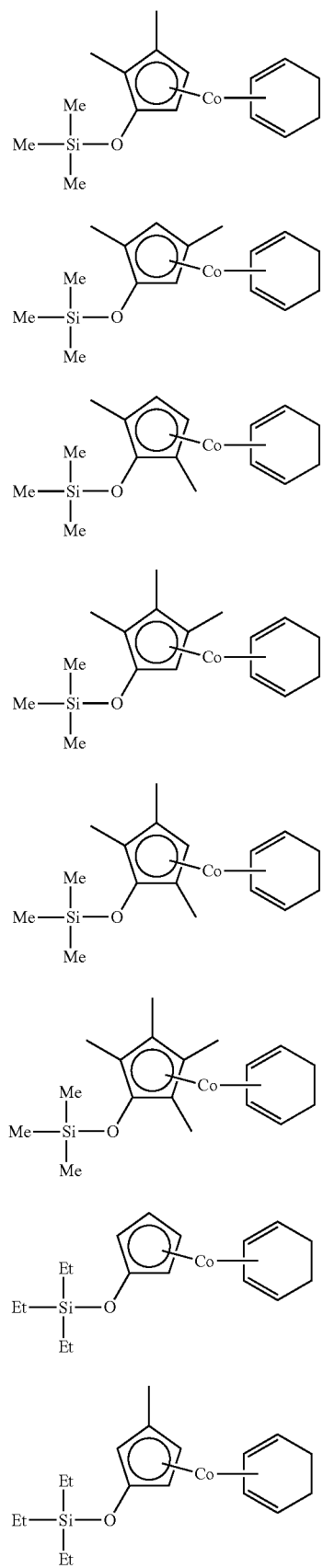
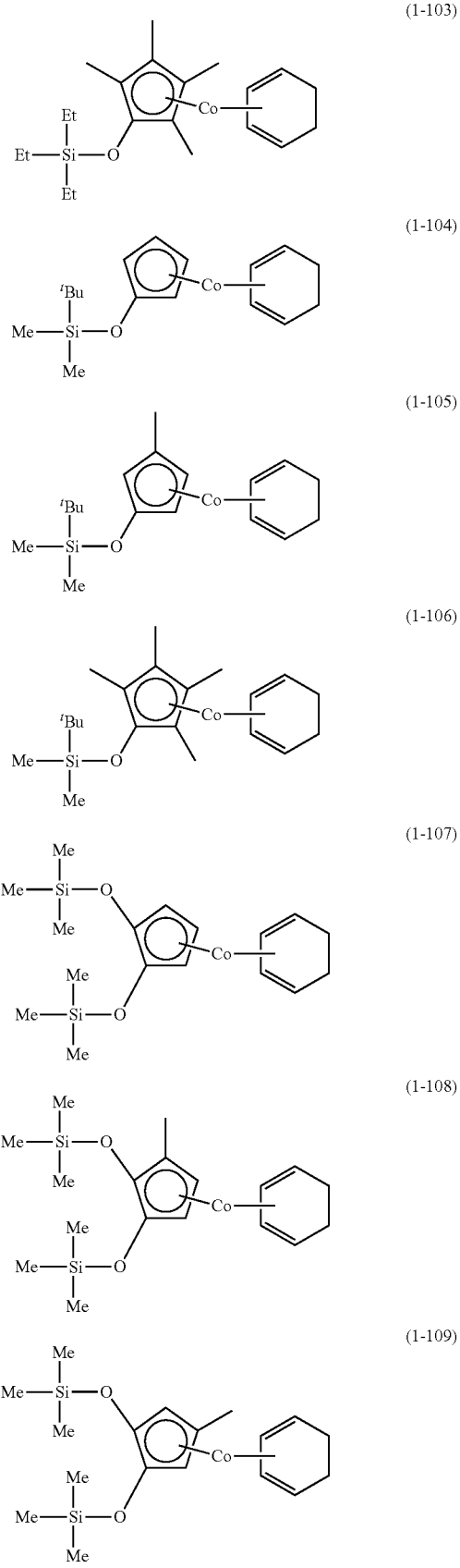

[Formula 14]
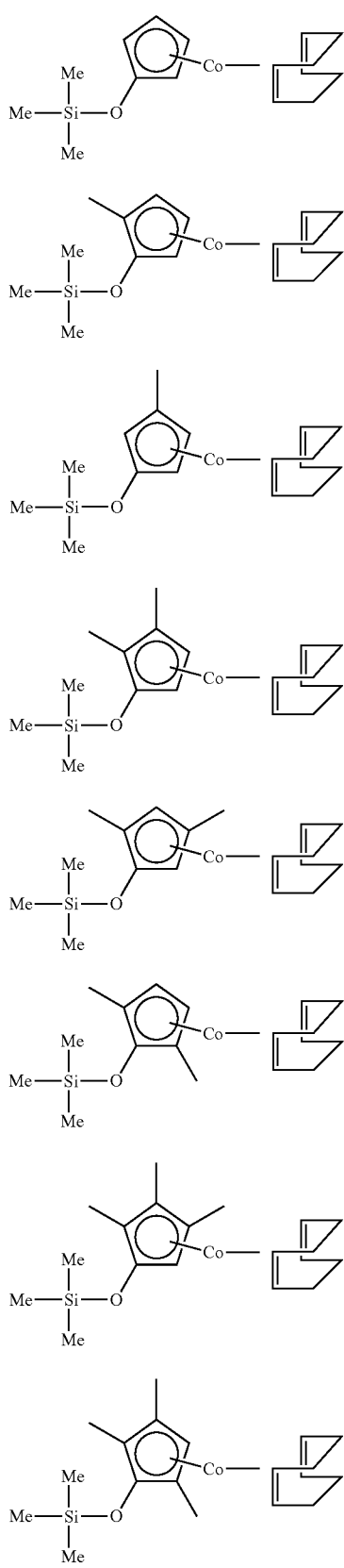
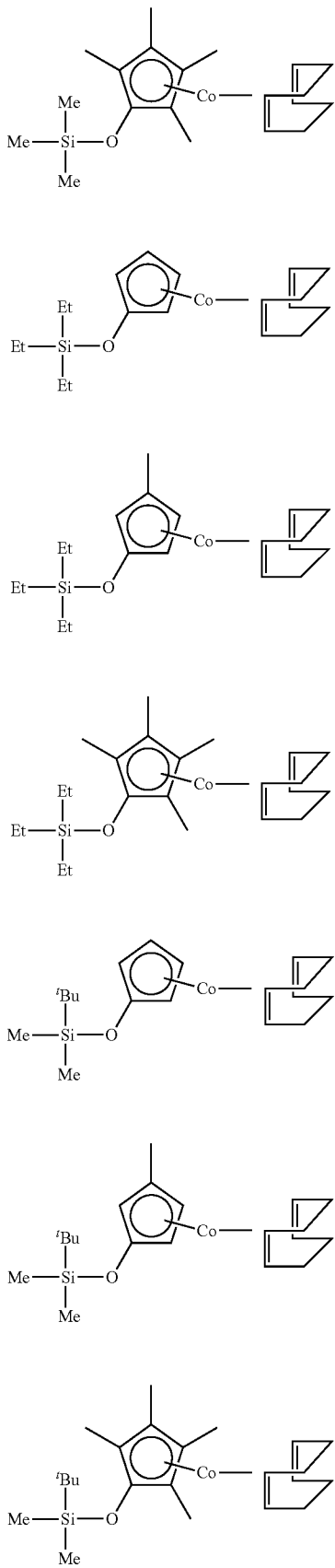

-continued
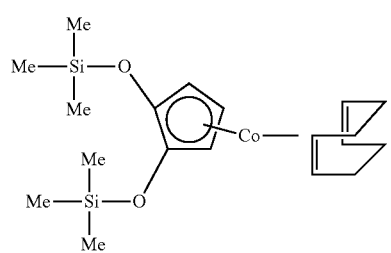
(1-125)
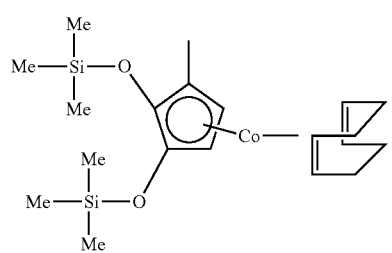
(1-126)
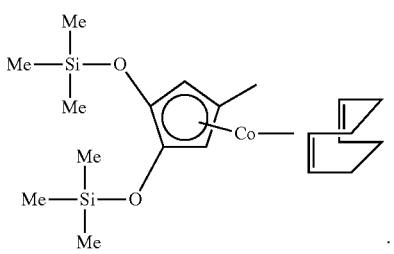
(1-127)
[Formula 15]
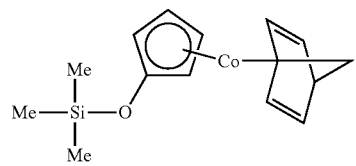
(1-128)
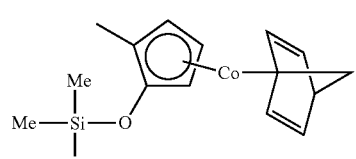
(1-129)
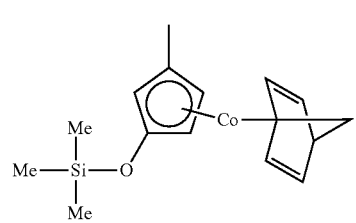
(1-130)
-continued
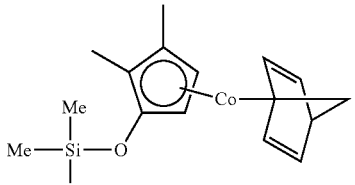
(1-131)
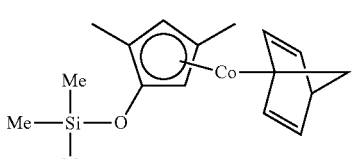
(1-132)
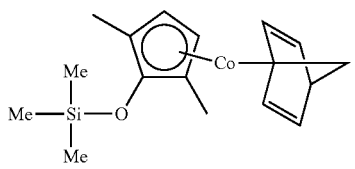
(1-133)
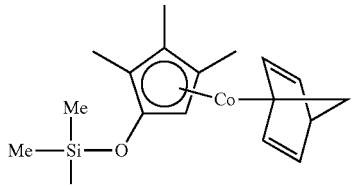
(1-134)
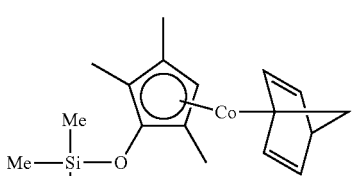
(1-135)
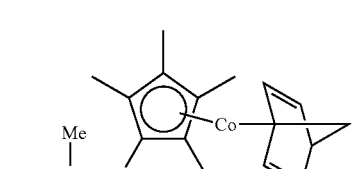
(1-136)
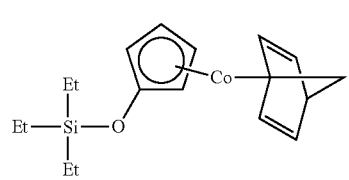
(1-137)
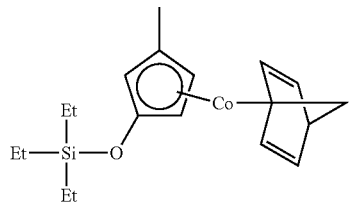
(1-138)

-continued

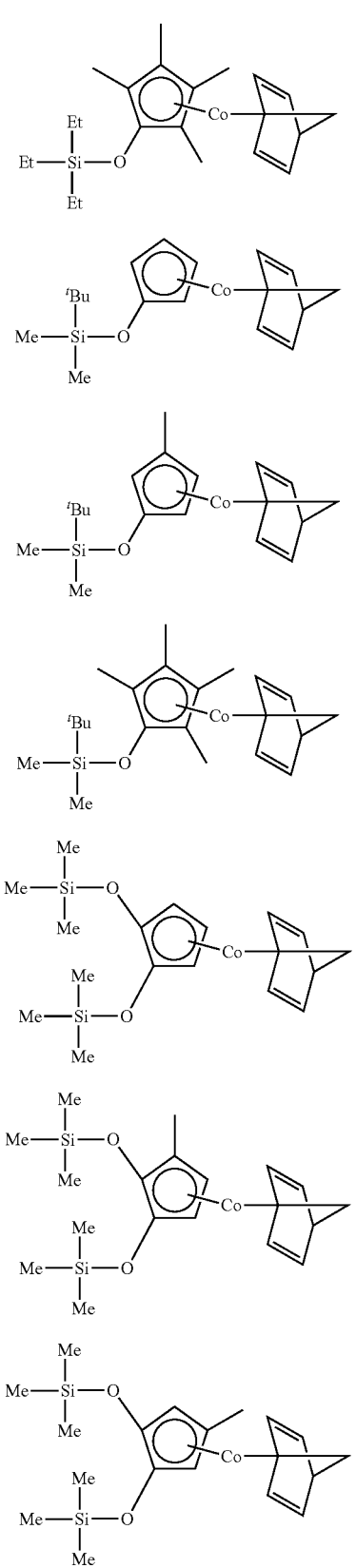

(1-139)

(1-140)

(1-141)

(1-142)

(1-143)

(1-144)

(1-145)

From the viewpoint of vapor pressure and thermal stability suitable for a CVD material or an ALD material, (1-1), (1-2), (1-3), (1-9), (1-17), (1-18), (1-19), (1-20), (1-21), (1-27), (1-35), (1-36), (1-37), (1-38), (1-39), (1-45), (1-53), (1-54), (1-55), (1-56), (1-57), (1-63), (1-71), (1-72), (1-73), (1-74), (1-75), (1-81), (1-90), (1-91), (1-92), (1-93), (1-94), (1-100), (1-108), (1-109), (1-110), (1-111), (1-112), (1-118), (1-126), (1-127), (1-128), (1-129), (1-130), (1-136), (1-144) and (1-145) are preferred, and (1-1), (1-3), (1-19), (1-21), (1-37), (1-39), (1-55), (1-57), (1-73), (1-75), (1-92), (1-94), (1-110), (1-112), (1-128) and (1-130) are especially preferred.

The following is a description of methods for producing a cobalt complex (1) of the present invention. Production Method 1 is a method for producing a cobalt complex (1) in which a trisphosphine complex represented by Formula (3) is reacted with lithium cyclopentadienide represented by Formula (4), and the product is reacted with a diene having from 4 to 10 carbon atoms.

Production Method 1

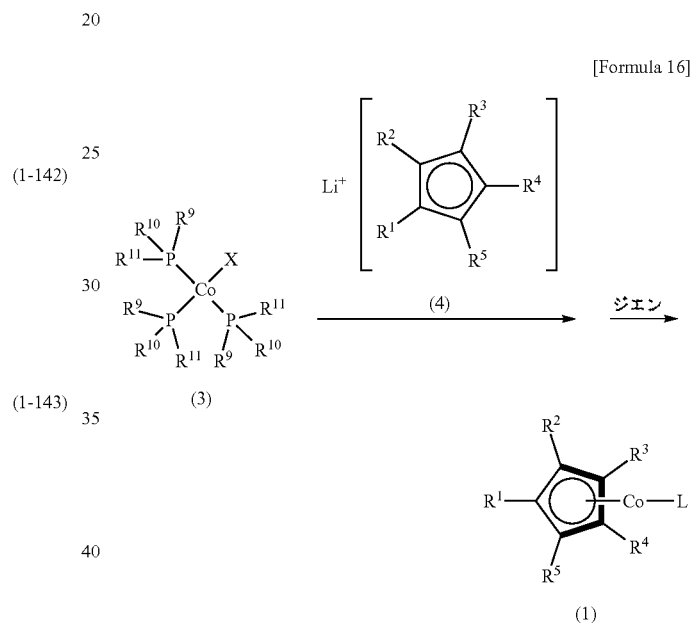

[Formula 16]

(In this formula, $R^1$, $R^2$, $R^3$, $R^4$ and $R^5$ have the same meaning as in Formula (1). $R^9$, $R^{10}$ and $R^{11}$ each individually represent a phenyl group, tolyl group, alkyl group having from 1 to 6 carbon atoms or an alkyloxy group having from 1 to 6 carbon atoms. X represents a halogen atom.)

The following is an explanation of the definition of $R^9$, $R^{10}$, $R^{11}$ and X in Formula (3). An alkyl group having from 1 to 6 carbon atoms that is represented by $R^9$, $R^{10}$ and $R^{11}$ may be linear, branched or cyclic. Specific examples include a methyl group, ethyl group, propyl group, isopropyl group, cyclopropyl group, butyl group, isobutyl group, sec-butyl group, tert-butyl group, cyclobutyl group, pentyl group, 1-ethylpropyl group, 1-methylbutyl group, 2-methylbutyl group, isopentyl group, neopentyl group, tert-pentyl group, cyclopentyl group, cyclobutylmethyl group, hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, cyclohexyl group, cyclopentylmethyl group, 1-cyclobutylethyl group, and 2-cyclobutylethyl group.

An alkyloxy group having from 1 to 6 carbon atoms that is represented by $R^9$, $R^{10}$ and $R^{11}$ may be linear, branched or cyclic. Specific examples include a methoxy group, ethoxy group, propyloxy group, isopropyloxy group, cyclopropyloxy group, butoxy group, isobutyloxy group, sec-butyloxy group, tert-butyloxy group, cyclobutyloxy group, pentyloxy group, 1-ethylpropyloxy group, 1-methylbutyloxy group, 2-methylbutyloxy group, isopentyloxy group, neopentyloxy group, tert-pentyloxy group, cyclopentyloxy group, cyclobutylmethyloxy group, hexyloxy group, 1-methylpentyloxy group, 2-methylpentyloxy group, 3-methylpentyloxy group, 4-methylpentyl group oxy, 1,1-dimethylbutyloxy group, 1,2-dimethylbutyloxy group, 1,3-dimethylbutyloxy group, 2,2-dimethylbutyloxy group, 2,3-dimethylbutyloxy group, 3,3-dimethylbutyloxy group, cyclohexyloxy group, cyclopentylmethyloxy group, 1-cyclobutylethyloxy group, and 2-cyclobutylethyloxy group.

The tolyl group represented by $R^9$, $R^{10}$ and $R^{11}$ may be an ortho-tolyl group (2-methylphenyl group), a meta-tolyl group (3-methylphenyl group) or a para-tolyl group (4-methylphenyl group).

From the viewpoint of a high yield of cobalt complex (1), $R^9$, $R^{10}$ and $R^{11}$ are preferably a phenyl group, an alkyl group having from 1 to 4 carbon groups, or an isopropyloxy group, are more preferably a phenyl group, methyl group or isopropyloxy group, and are even more preferably a phenyl group.

The halogen atom represented by X may be a chlorine atom, a bromine atom or an iodine atom. From the viewpoint of a high yield, a chlorine atom is preferred.

Examples of trisphosphine complexes (3) that can be used in Production Method 1 include chlorotris(triphenylphosphine)cobalt, bromotris(triphenylphosphine)cobalt, iodotris(triphenylphosphine)cobalt, chlorotris(tris(2-methylphenyl)phosphine)cobalt, bromotris(tris(2-methylphenyl)phosphine)cobalt, iodotris(tris(2-methylphenyl)phosphine)cobalt, chlorotris(tris(3-methylphenyl)phosphine)cobalt, bromotris(tris(3-methylphenyl)phosphine)cobalt, iodotris(tris(3-methylphenyl)phosphine)cobalt, chlorotris(tris(4-methylphenyl)phosphine)cobalt, bromotris(tris(4-methylphenyl)phosphine)cobalt, iodotris(tris(4-methylphenyl)phosphine)cobalt, chlorotris(tris(methyldiphenylphosphine)cobalt, bromotris(tris(methyldiphenylphosphine)cobalt, iodotris(tris(methyldiphenylphosphine)cobalt, chlorotris(tris(dimethylphenylphosphine)cobalt, bromotris(tris(dimethylphenylphosphine)cobalt, iodotris(tris(dimethylphenylphosphine)cobalt, chlorotris(trimethylphosphine)cobalt, bromotris(trimethylphosphine)cobalt, iodotris(trimethylphosphine)cobalt, chlorotris(triethylphosphine)cobalt, bromotris(triethylphosphine)cobalt, iodotris(triethylphosphine)cobalt, chlorotris(tripropylphosphine)cobalt, bromotris(tripropylphosphine)cobalt, iodotris(tripropylphosphine)cobalt, chlorotris(triisopropylphosphine)cobalt, bromotris(triisopropylphosphine)cobalt, iodotris(triisopropylphosphine)cobalt, chlorotris(tributylphosphine)cobalt, bromotris(tributylphosphine)cobalt, iodotris(tributylphosphine)cobalt, chlorotris(triisobutylphosphine)cobalt, bromotris(triisobutylphosphine)cobalt, iodotris(triisobutylphosphine)cobalt, chlorotris(trimethylphosphite)cobalt, bromotris(trimethylphosphite)cobalt, iodotris(trimethylphosphite)cobalt, chlorotris(triethylphosphite)cobalt, bromotris(triethylphosphite)cobalt, iodotris(triethylphosphite)cobalt, chlorotris(tripropylphosphite)cobalt, bromotris(tripropylphosphite)cobalt, iodotris(tripropylphosphite)cobalt, chlorotris(triisopropylphosphite)cobalt, bromotris(triisopropylphosphite)cobalt, iodotris(triisopropylphosphite)cobalt, chlorotris(tributylphosphite)cobalt, bromotris(tributylphosphite)cobalt, iodotris(tributylphosphite)cobalt, chlorotris(triisobutylphosphite)cobalt, bromotris(triisobutylphosphite)cobalt, iodotris(triisobutylphosphite)cobalt, chlorotris(tri sec-butylphosphite)cobalt, bromotris(tri sec-butylphosphite)cobalt, and iodotris(tri sec-butylphosphite)cobalt. From the viewpoint of low cost chlorotris(triphenylphosphine)cobalt, chlorotris(trimethylphosphine)cobalt, chlorotris(triethylphosphine)cobalt, chlorotris(tripropylphosphine)cobalt, chlorotris(tributylphosphine)cobalt and chlorotris(triisopropyl phosphite)cobalt are preferred, chlorotris(triphenylphosphine)cobalt, chlorotris(trimethylphosphine)cobalt, chlorotris(triethylphosphine)cobalt and chlorotris(triisopropylphosphite)cobalt are more preferred, and chlorotris(triphenylphosphine)cobalt is even more preferred.

A trisphosphine complex (3) that can be used in Production Method 1 can be obtained using the methods described in Chemische Berichte, vol. 108, p. 944 (1975), Inorganic Syntheses, vol. 26, p. 190 (1989), and Journal of the American Chemical Society, vol. 99, p. 739 (1977).

Examples of lithium cyclopentadienide (4) that can be used in Production Method 1 include the following.

[Formula 17]

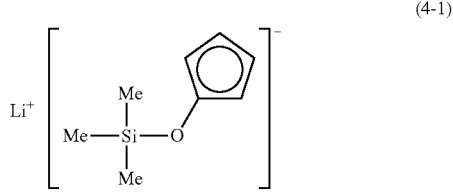

(4-1)

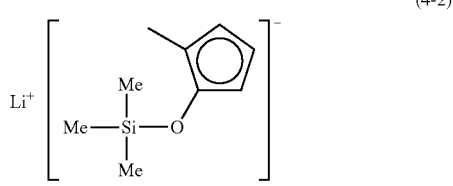

(4-2)

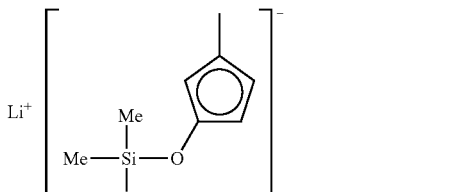

(4-3)

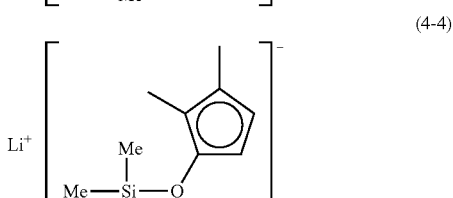

(4-4)

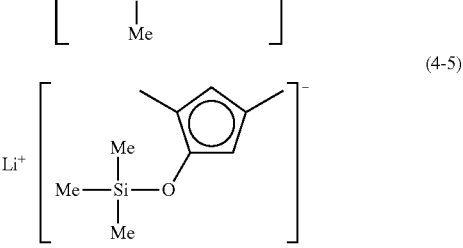

(4-5)

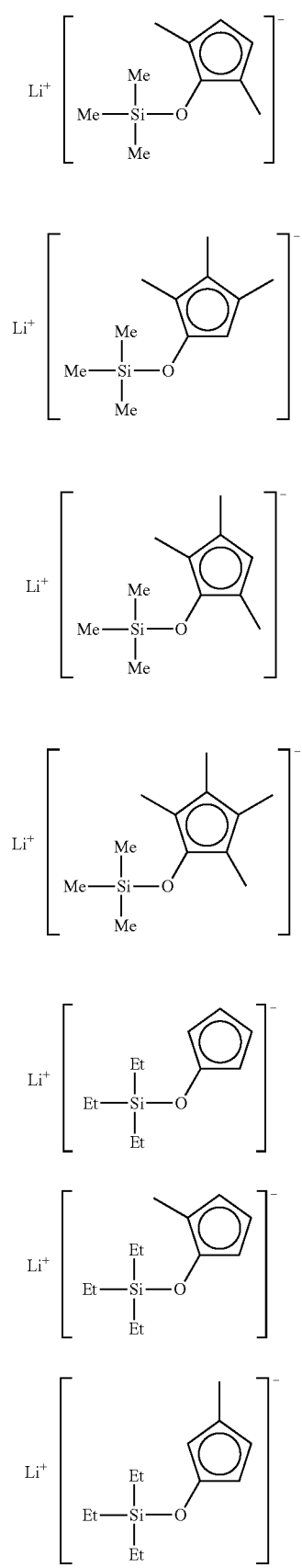
(4-6)
(4-7)
(4-8)
(4-9)
(4-10)
(4-11)
(4-12)
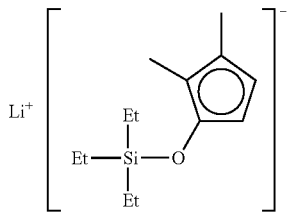
(4-13)
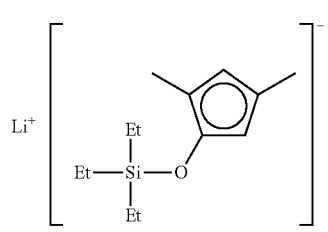
(4-14)
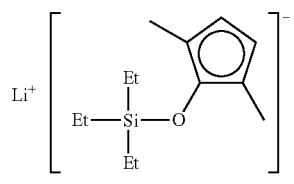
(4-15)
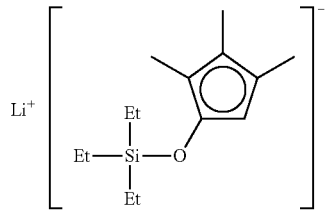
(4-16)
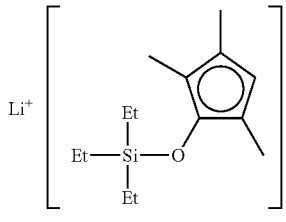
(4-17)
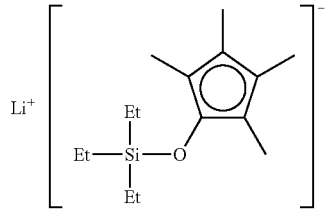
(4-18)

[Formula 18]
(4-19)
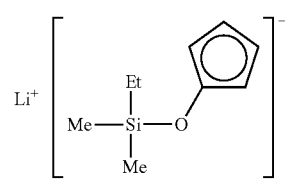
(4-20)
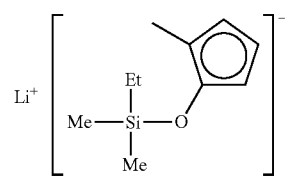
(4-21)
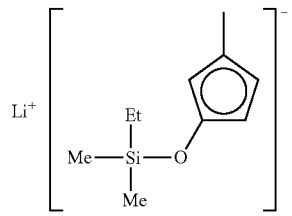
(4-22)
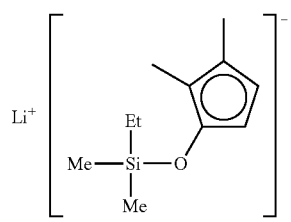
(4-23)
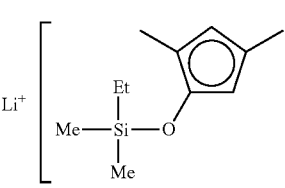
(4-24)
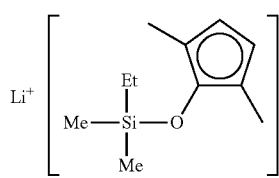
(4-25)
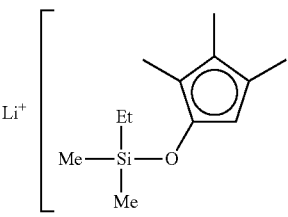
-continued
(4-26)
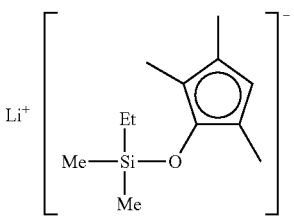
(4-27)
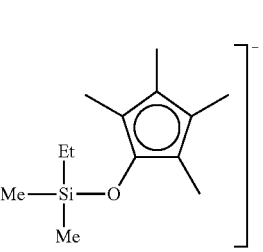
(4-28)
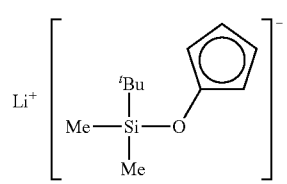
(4-29)
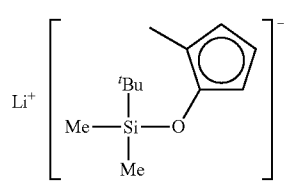
(4-30)
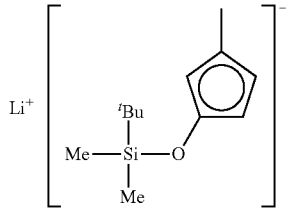
(4-31)
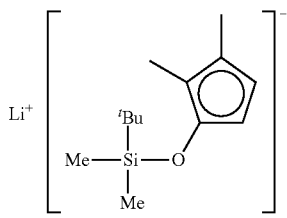
(4-32)
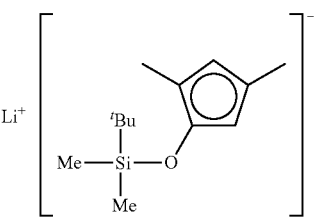

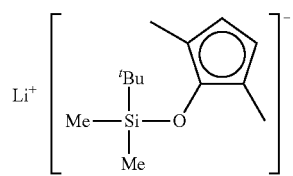 (4-33)
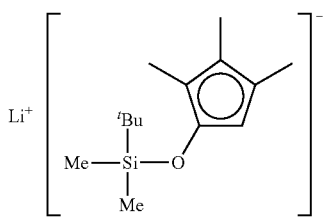 (4-34)
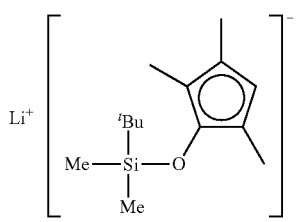 (4-35)
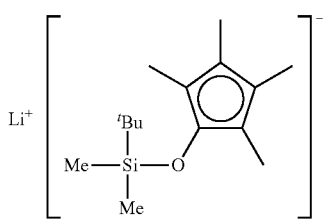 (4-36)
[Formula 19]
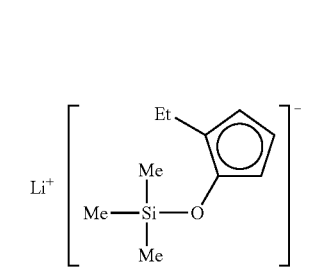 (4-37)
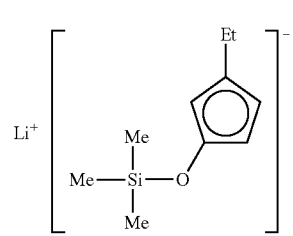 (4-38)
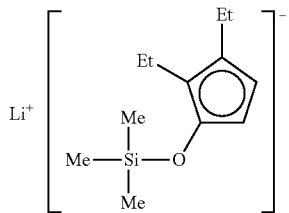 (4-39)
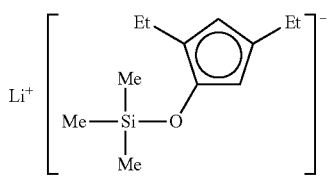 (4-40)
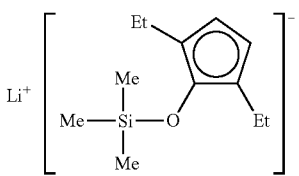 (4-41)
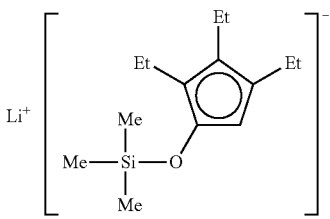 (4-42)
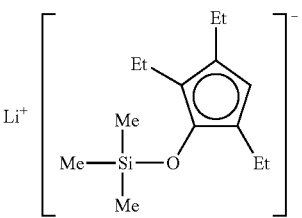 (4-43)
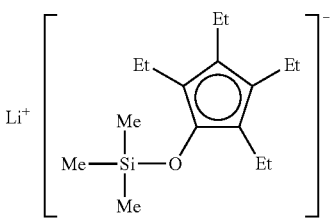 (4-44)
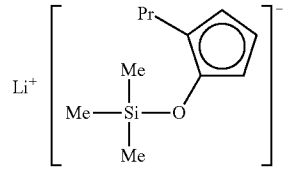 (4-45)

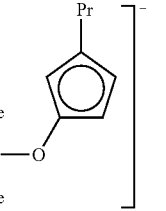 (4-46)
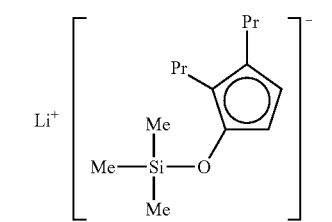 (4-47)
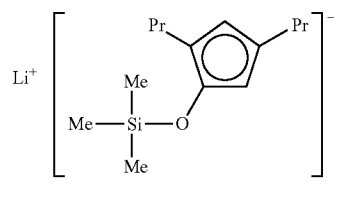 (4-48)
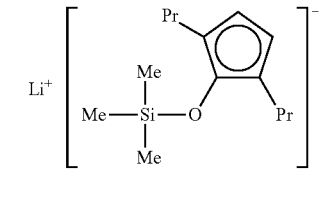 (4-49)
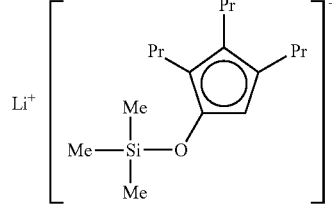 (4-50)
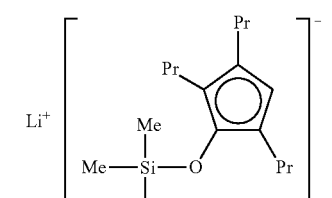 (4-51)
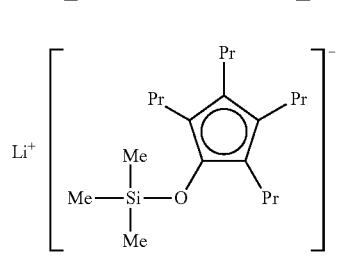 (4-52)
[Formula 20]
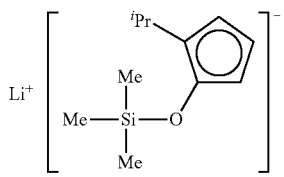 (4-53)
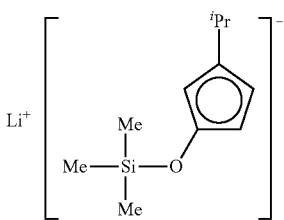 (4-54)
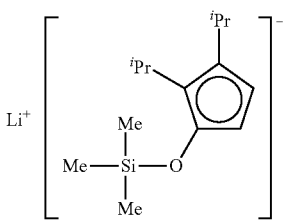 (4-55)
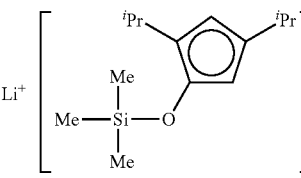 (4-56)
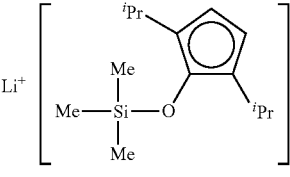 (4-57)
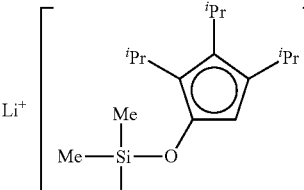 (4-58)
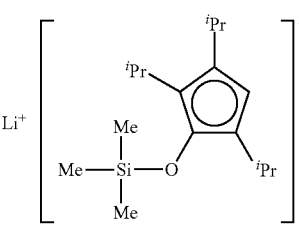 (4-59)

-continued
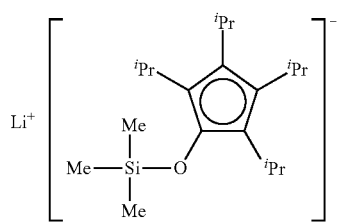 (4-60)
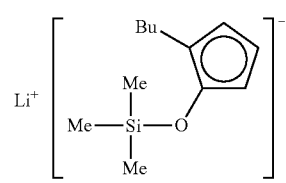 (4-61)
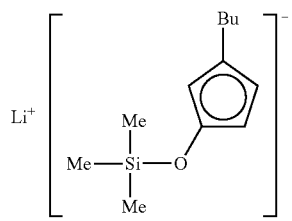 (4-62)
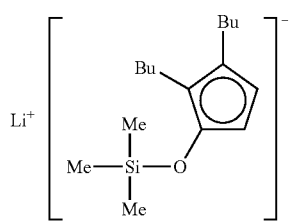 (4-63)
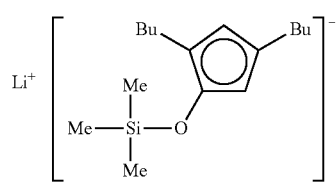 (4-64)
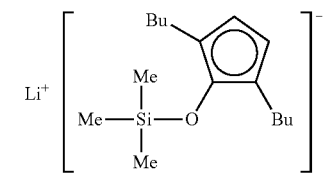 (4-65)
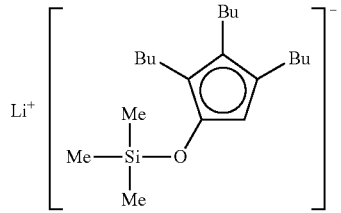 (4-66)
-continued
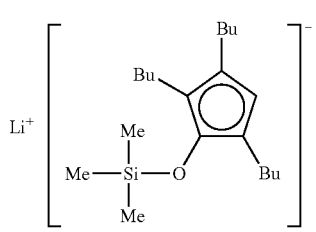 (4-67)
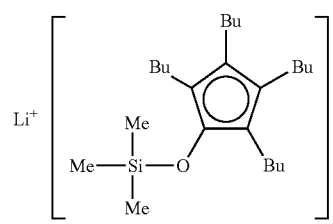 (4-68)
[Formula 21]
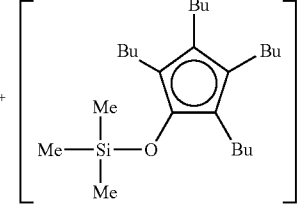 (4-69)
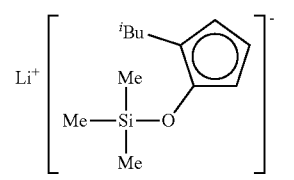 (4-70)
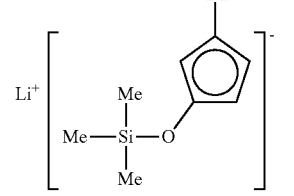 (4-71)
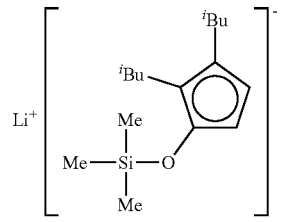 (4-72)
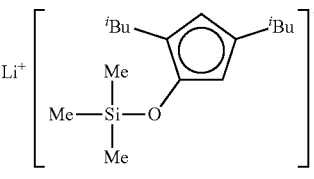 (4-73)

-continued
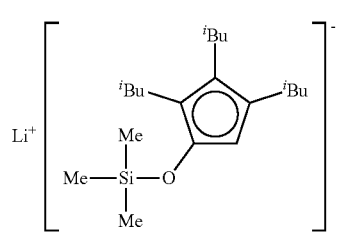
(4-74)
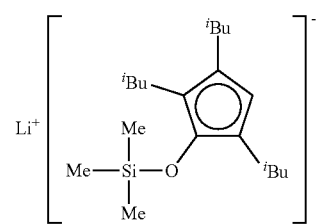
(4-75)
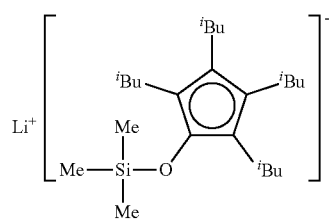
(4-76)
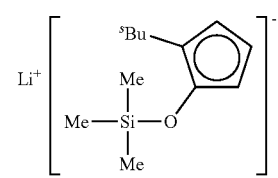
(4-77)
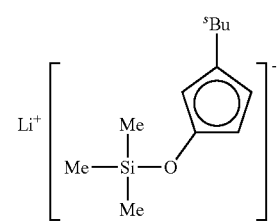
(4-78)
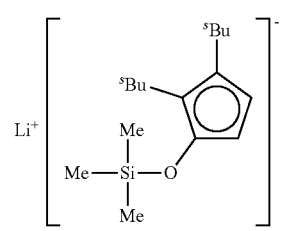
(4-79)
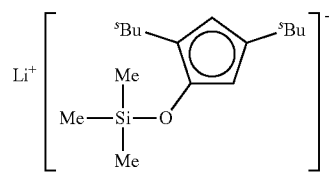
(4-80)
-continued
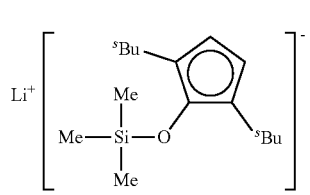
(4-81)
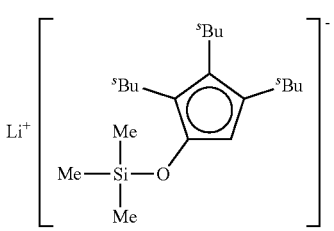
(4-82)
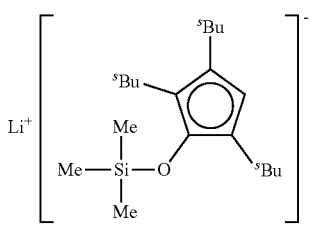
(4-83)
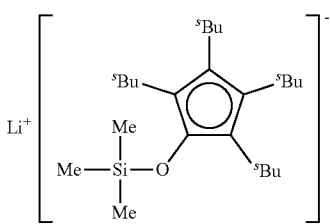
(4-84)
[Formula 22]
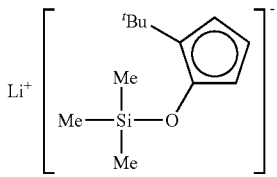
(4-85)
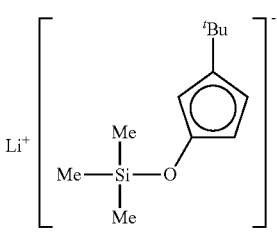
(4-86)

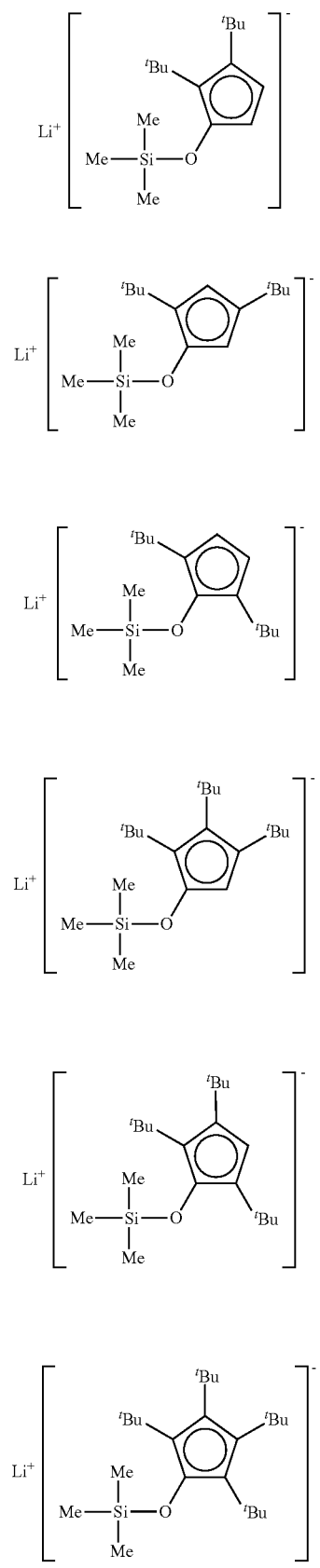
[Formula 23]
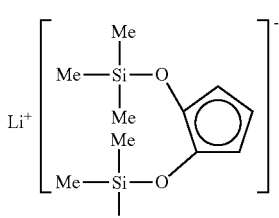
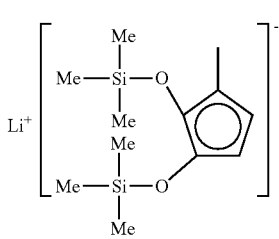
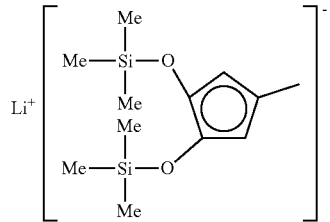
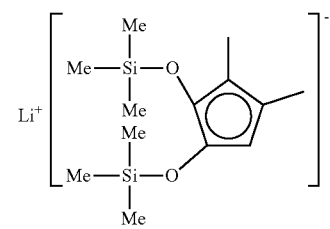
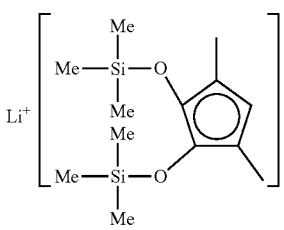
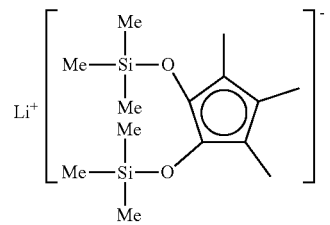
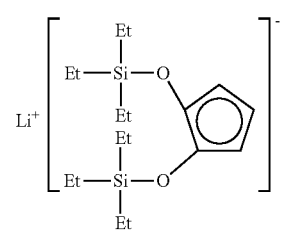

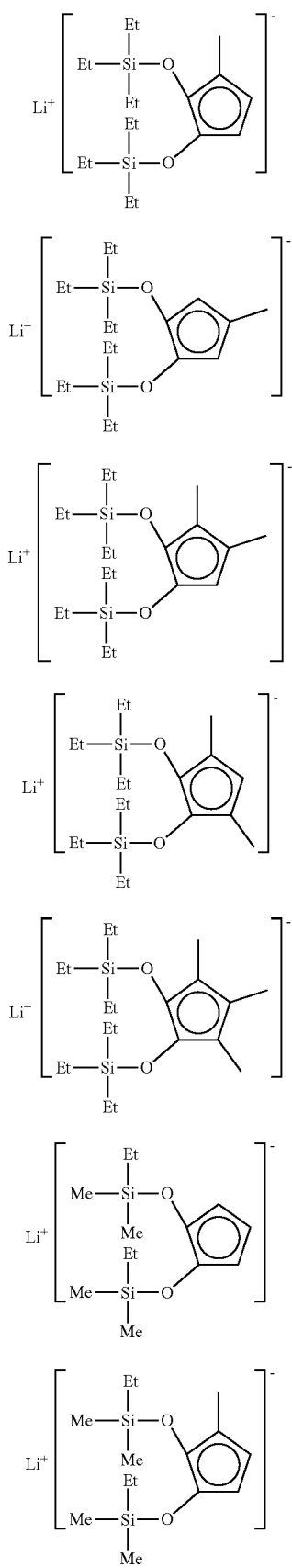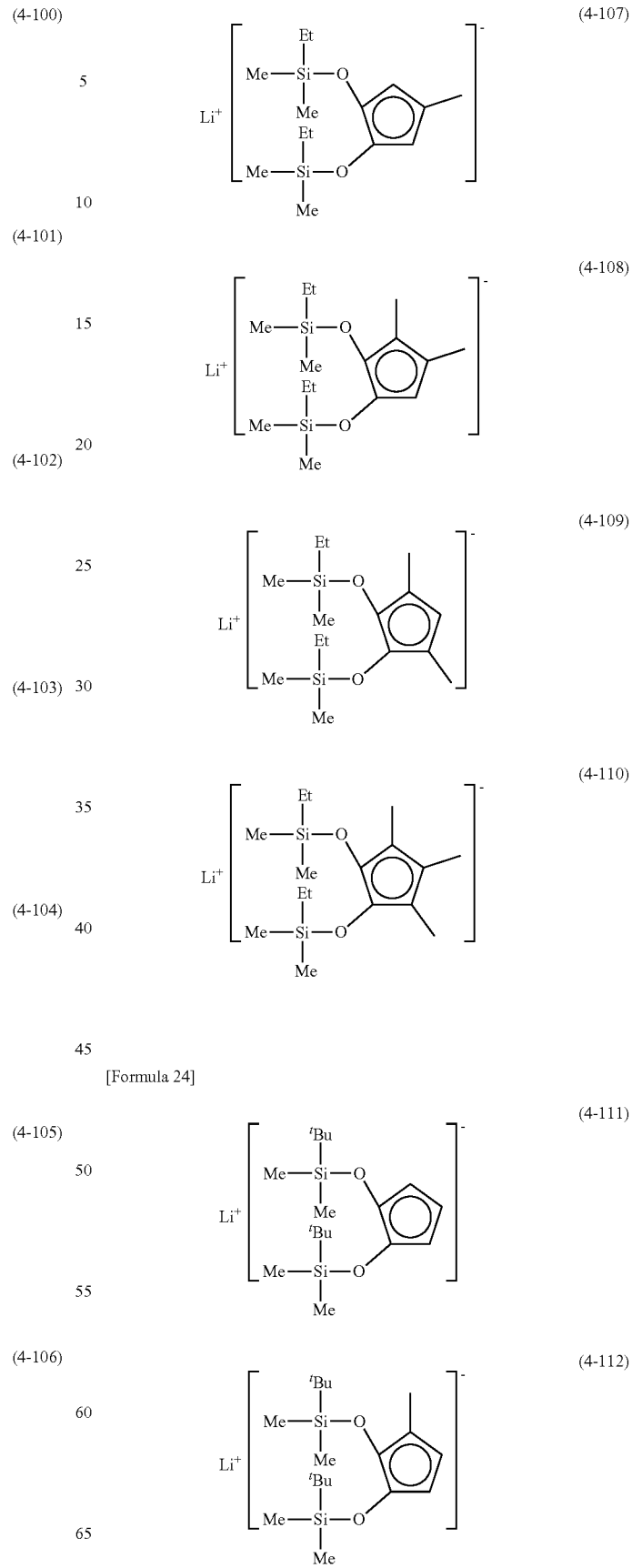
[Formula 24]

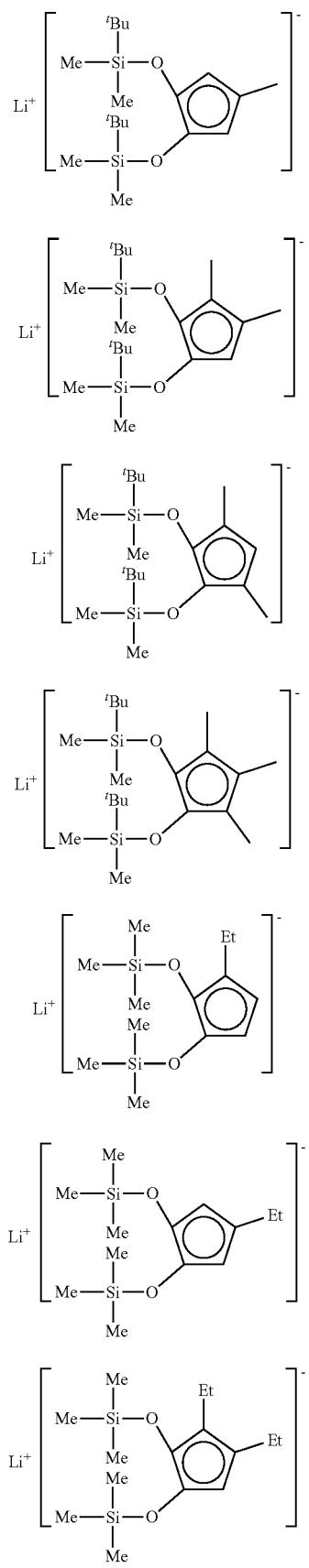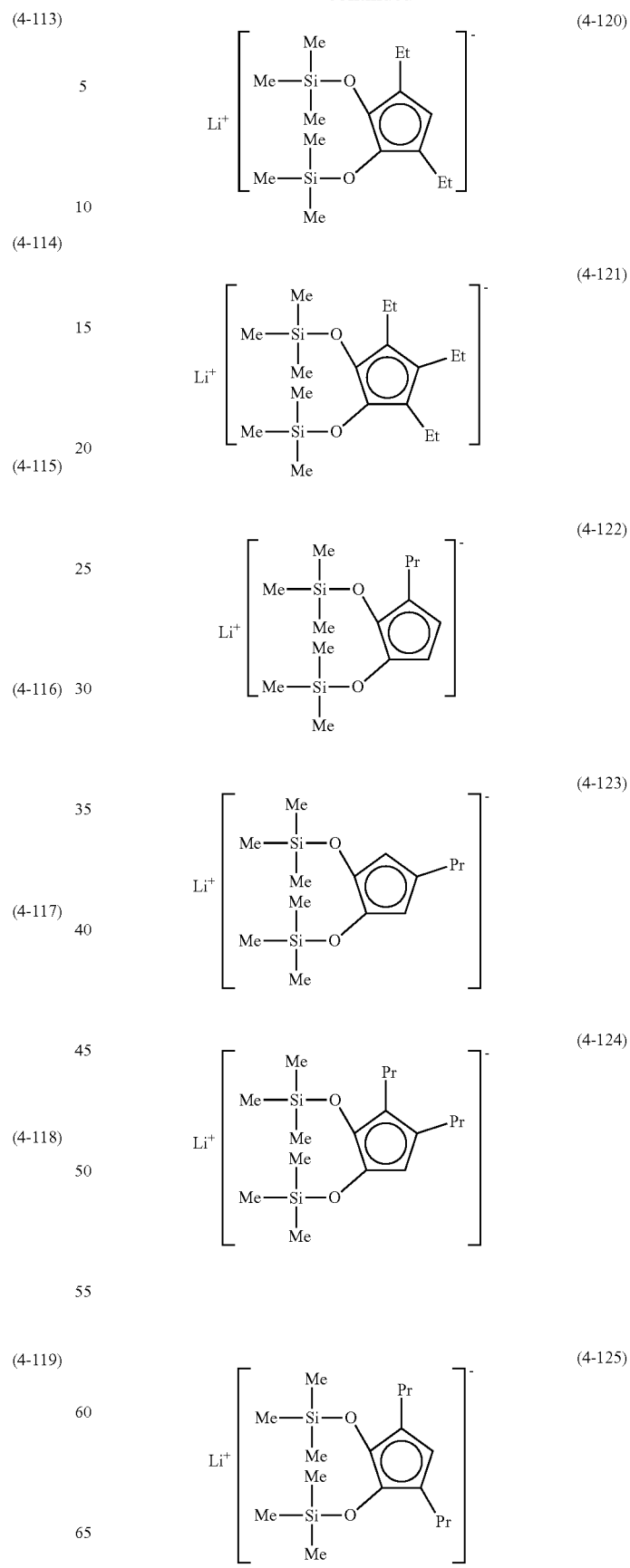

(4-126)
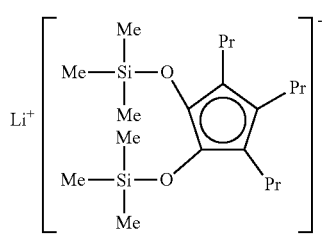
[Formula 25]
(4-127)
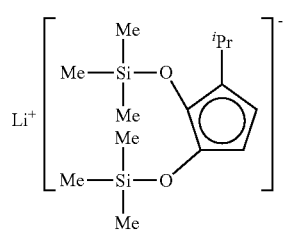
(4-128)
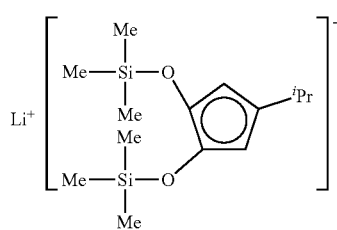
(4-129)
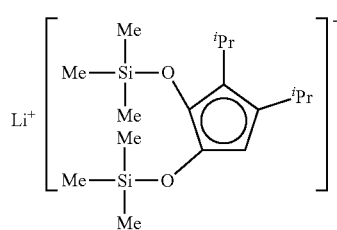
(4-130)
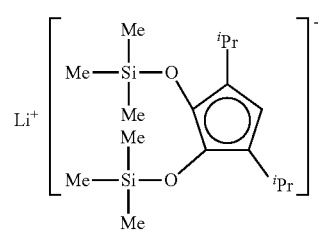
(4-131)
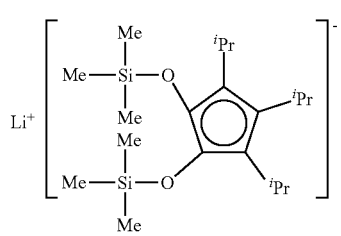
(4-132)
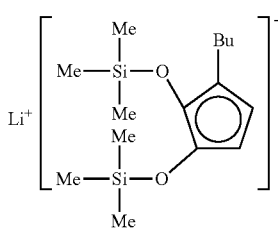
(4-133)
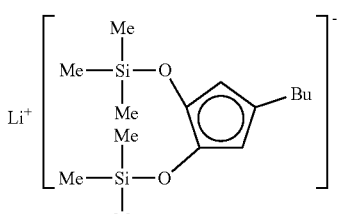
(4-134)
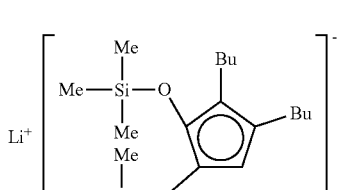
(4-135)
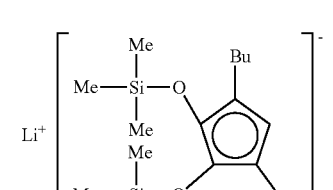
(4-136)
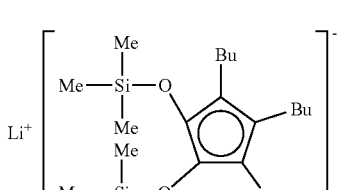
(4-137)
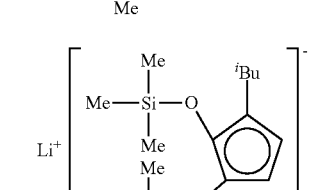
(4-138)
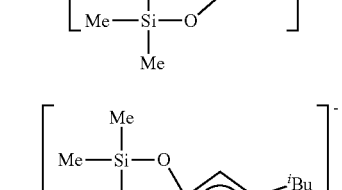

(4-139)
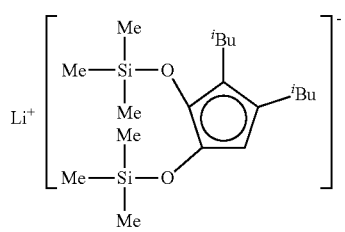
(4-140)
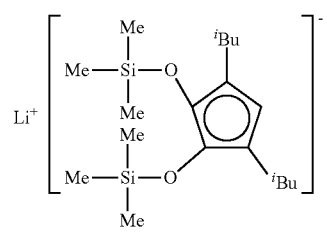
(4-141)
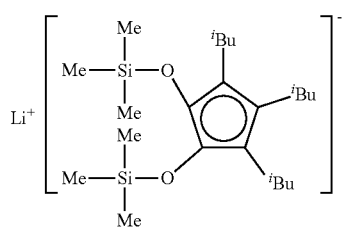
[Formula 26]
(4-142)
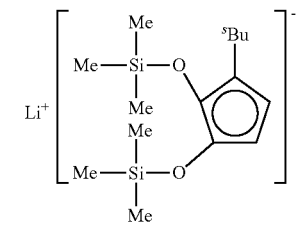
(4-143)
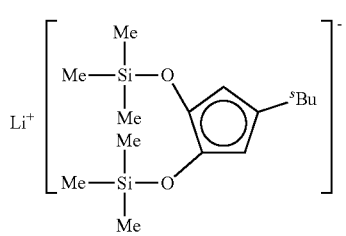
(4-144)
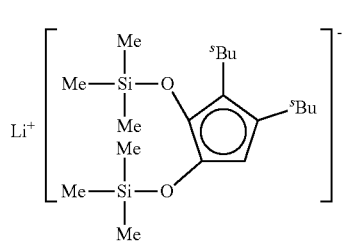
(4-145)
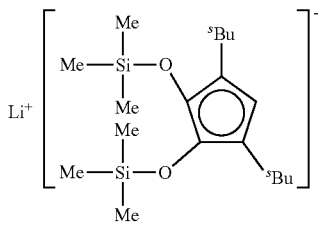
(4-146)
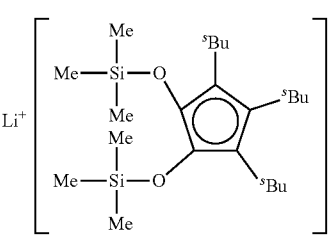
(4-147)
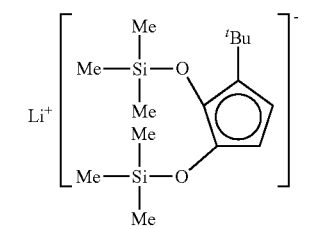
(4-148)
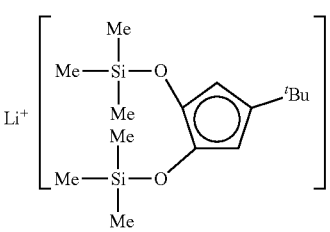
(4-149)
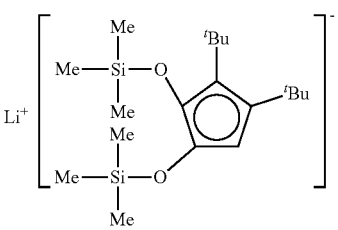
(4-150)
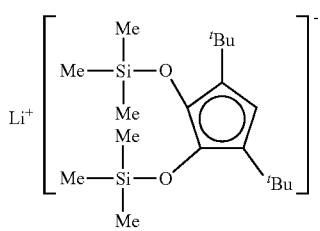
(4-151)
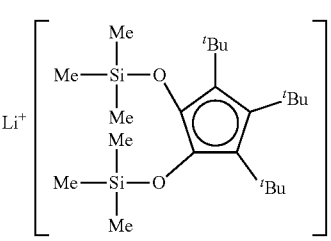

From the viewpoint of obtaining a cobalt complex (1) having vapor pressure and thermal stability suitable for a CVD material or an ALD material, (4-1), (4-2), (4-3), (4-4), (4-5), (4-6), (4-7), (4-8), (4-9), (4-10), (4-11), (4-12), (4-13), (4-14), (4-15), (4-16), (4-17), (4-18), (4-28), (4-29), (4-30), (4-31), (4-32), (4-33), (4-34), (4-35), (4-36), (4-93), (4-94), (4-95), (4-96), (4-97) or (4-98) is preferred, (4-1), (4-2), (4-3), (4-4), (4-5), (4-6), (4-7), (4-8), (4-9), (4-93), (4-94), (4-95), (4-96), (4-97) or (4-98) is more preferred, and (4-1), (4-3), (4-93) or (4-94) is even more preferred.

The lithium cyclopentadienide (4) used in Production Method 1 can be obtained by reacting and lithiating a substituted cyclopentadiene (5) with a lithiating agent.

The substituted cyclopentadiene (5) may have the structure represented by Formula (5), but may also be an isomer represented by Formulas (5a), (5b), (5c) or (5d), or a mixture of any one of compounds represented by Formula (5) or Formulas (5a) to (5d).

[Formula 27]

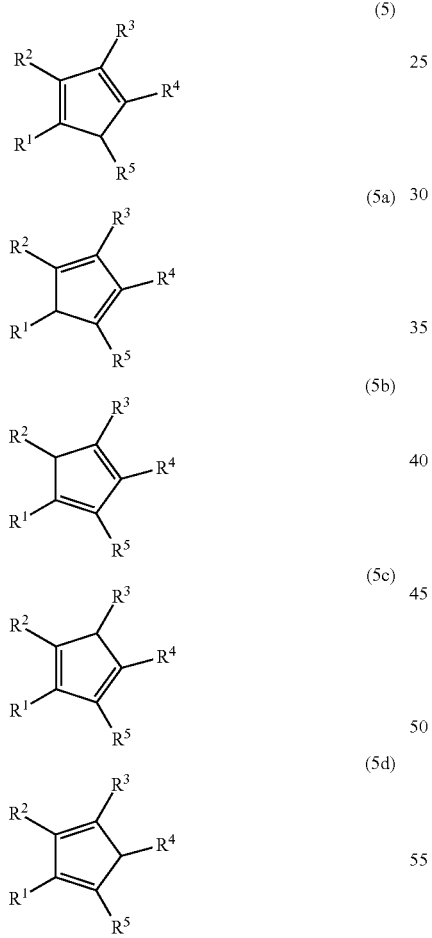

(In these formulas, $R^1$, $R^2$, $R^3$, $R^4$ and $R^5$ have the same meaning as $R^1$, $R^2$, $R^3$, $R^4$ and $R^5$ in Formula (1).)

For the sake of simplicity, Formulas (5) and (5a) to (5d) are referred to collectively herein as Formula (5).

These substituted cyclopentadienes (5) can be obtained using the methods described in Reference Examples 1-3 in the present specification, Organometallics, vol. 16, p. 5950 (1997), Acta Chemica Scandinavica, vol. 43, p. 188 (1989), Chemical Communication, p. 2123 (1996), Journal of Organometallic Chemistry, vol. 544, p. 133 (1997), and Journal of Organometallic Chemistry, vol. 558, p. 231 (1998).

The following are examples of substituted cyclopentadienes (5).

[Formula 28]

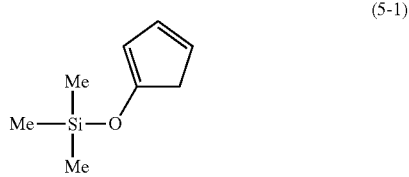

(5-1)

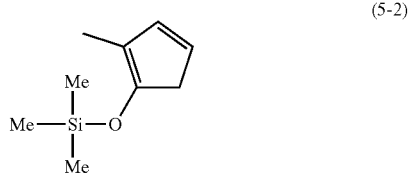

(5-2)

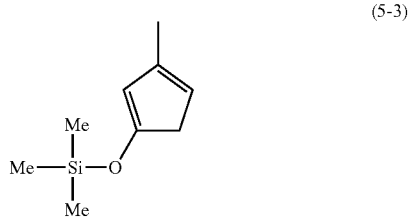

(5-3)

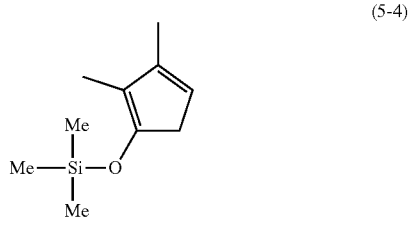

(5-4)

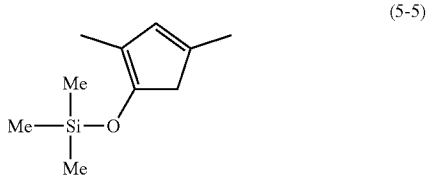

(5-5)

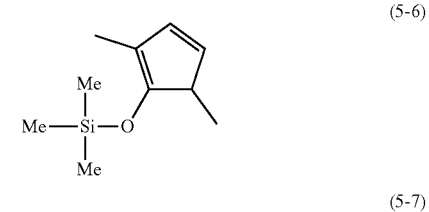

(5-6)

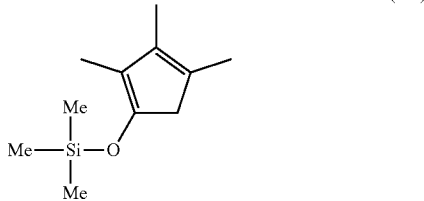

(5-7)

-continued
(5-8)
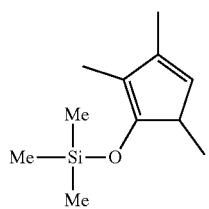
(5-9)
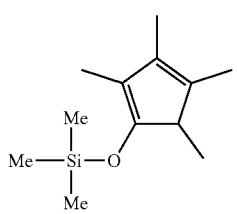
(5-10)
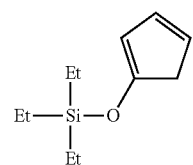
(5-11)
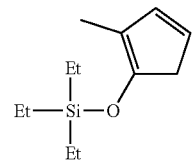
(5-12)
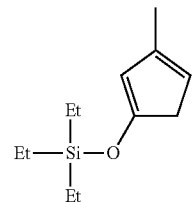
(5-13)
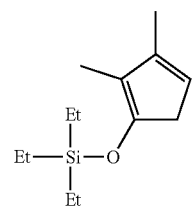
(5-14)
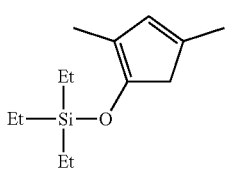
(5-15)
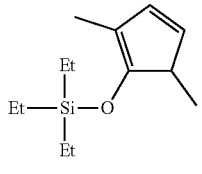
-continued
(5-16)
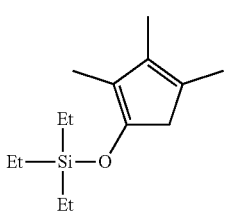
(5-17)
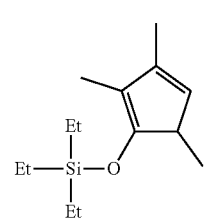
(5-18)
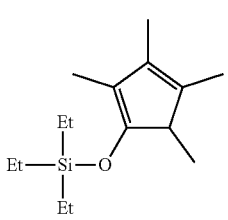
[Formula 29]
(5-19)
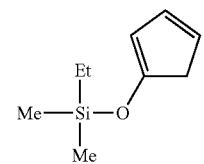
(5-20)
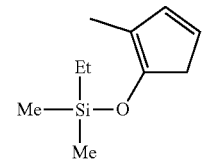
(5-21)
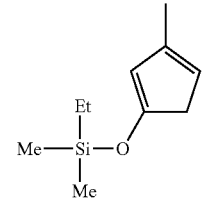
(5-22)
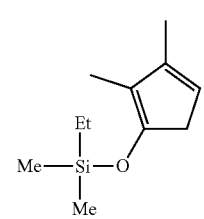

-continued
(5-23) 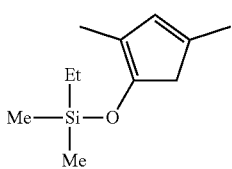
(5-24) 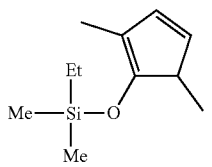
(5-25) 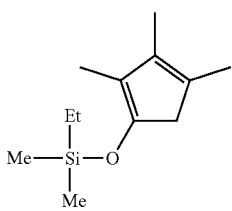
(5-26) 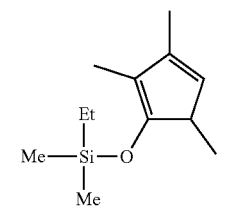
(5-27) 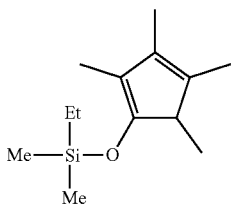
(5-28) 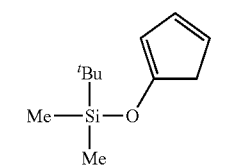
(5-29) 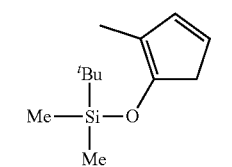
(5-30) 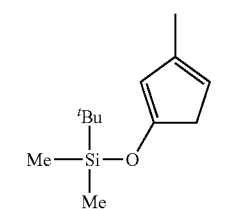
-continued
(5-31) 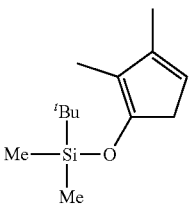
(5-32) 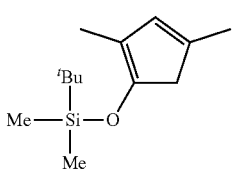
(5-33) 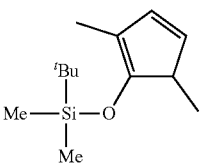
(5-34) 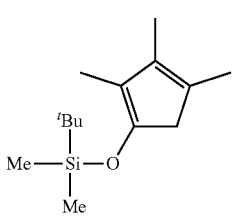
(5-35) 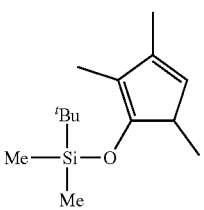
(5-36) 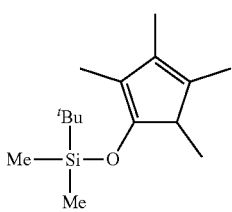
[Formula 30]
(5-37) 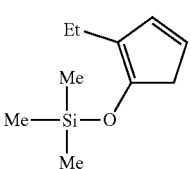

(5-38) 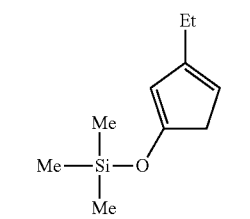
(5-39) 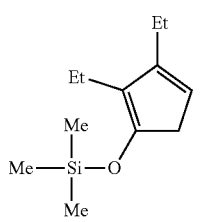
(5-40) 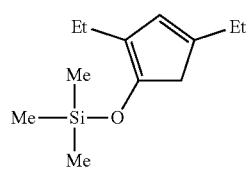
(5-41) 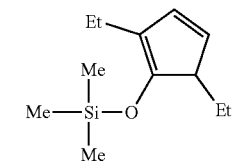
(5-42) 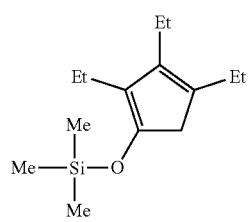
(5-43) 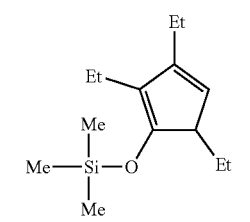
(5-44) 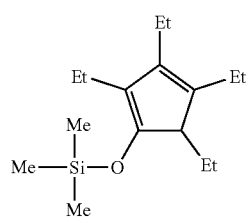
(5-45) 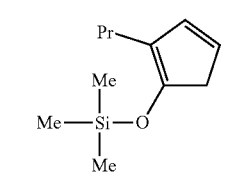
(5-46) 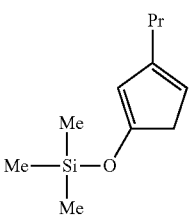
(5-47) 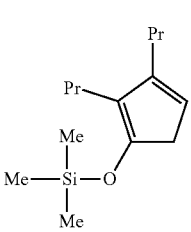
(5-48) 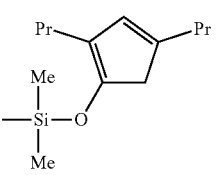
(5-49) 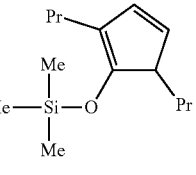
(5-50) 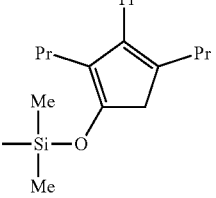
(5-51) 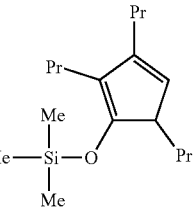
(5-52) 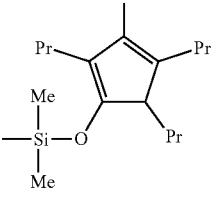

[Formula 31]
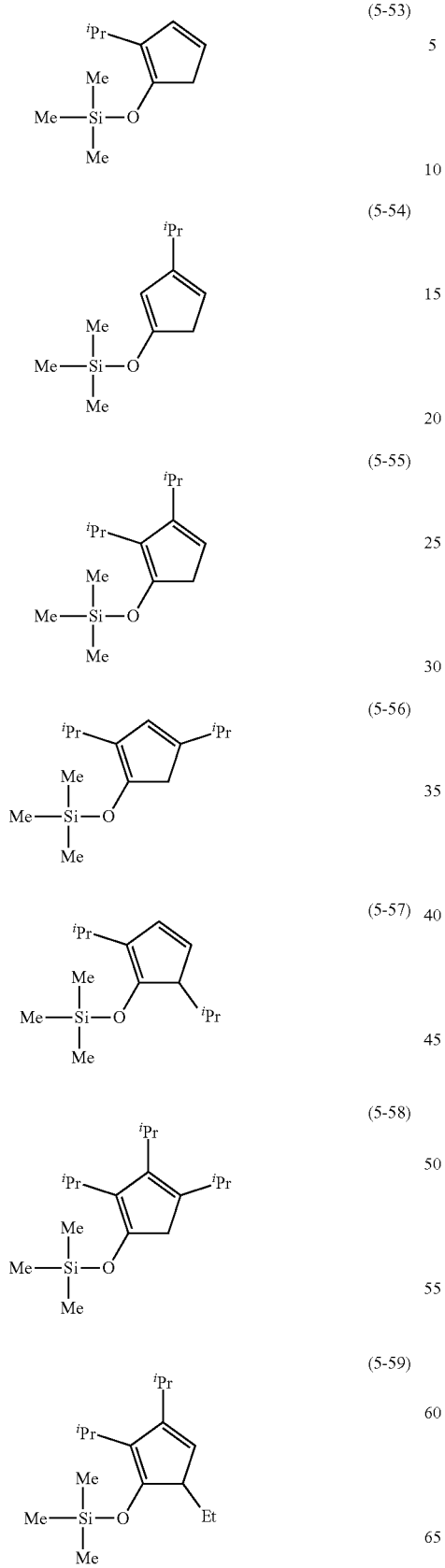
(5-53)
(5-54)
(5-55)
(5-56)
(5-57)
(5-58)
(5-59)
-continued
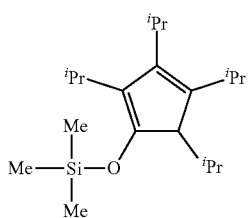 (5-60)
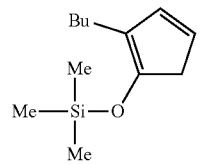 (5-61)
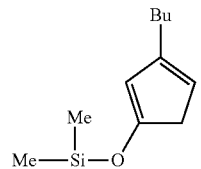 (5-62)
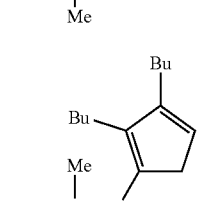 (5-63)
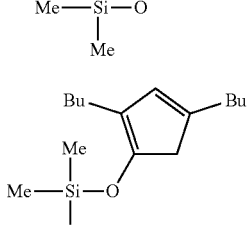 (5-64)
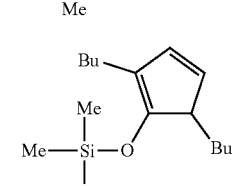 (5-65)
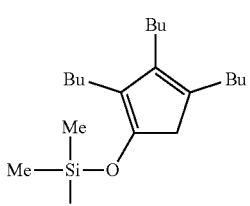 (5-66)
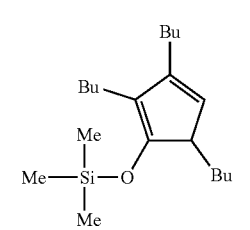 (5-67)

(5-68) 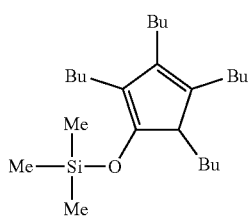
[Formula 32]
(5-69) 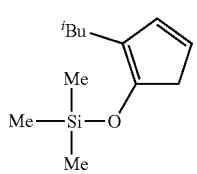
(5-70) 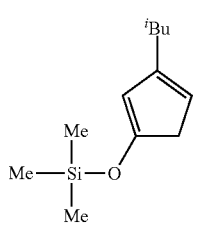
(5-71) 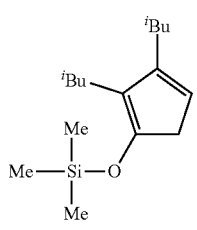
(5-72) 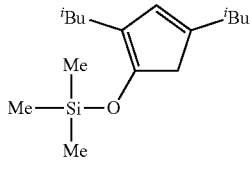
(5-73) 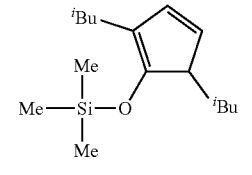
(5-74) 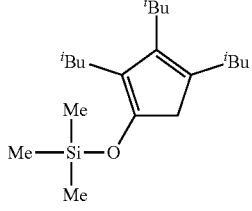
(5-75) 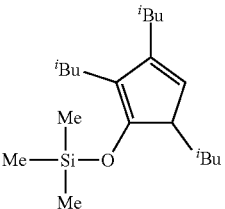
(5-76) 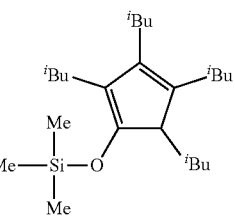
(5-77) 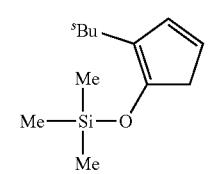
(5-78) 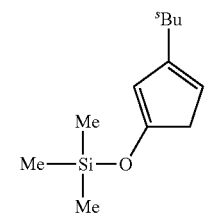
(5-79) 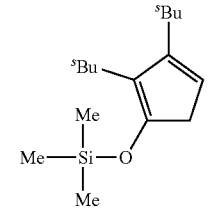
(5-80) 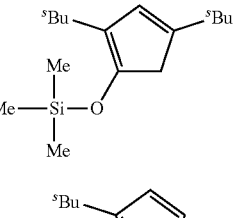
(5-81) 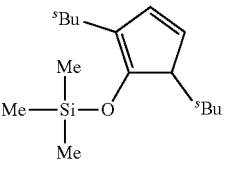
(5-82) 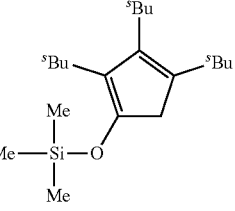

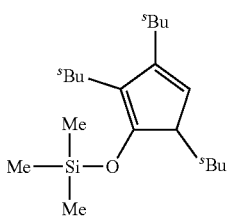 (5-83)
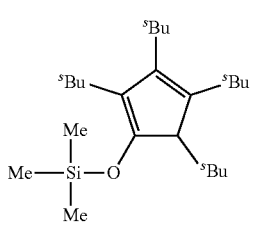 (5-84)
[Formula 33]
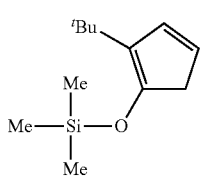 (5-85)
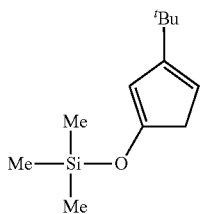 (5-86)
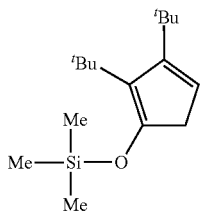 (5-87)
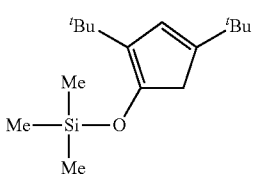 (5-88)
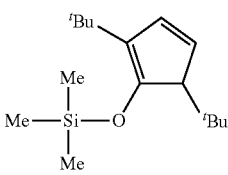 (5-89)
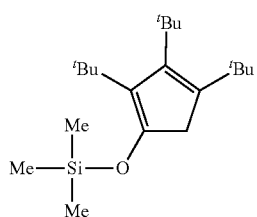 (5-90)
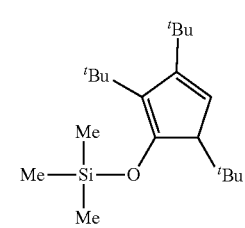 (5-91)
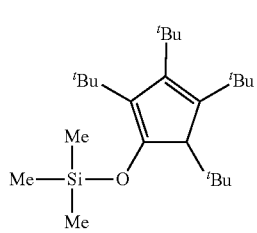 (5-92)
[Formula 34]
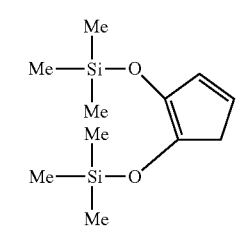 (5-93)
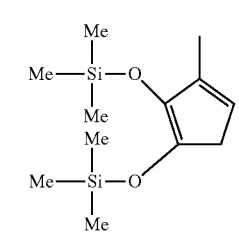 (5-94)
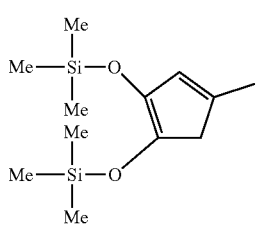 (5-95)

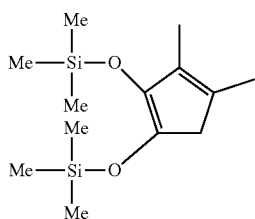 (5-96)
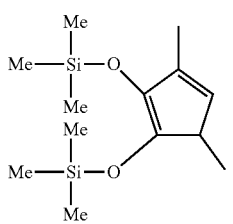 (5-97)
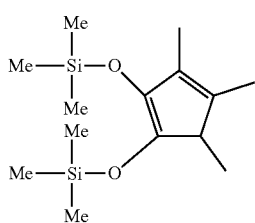 (5-98)
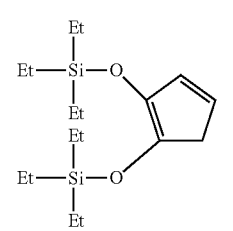 (5-99)
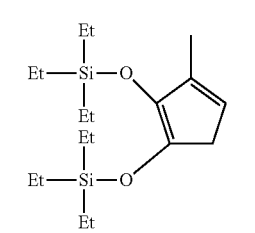 (5-100)
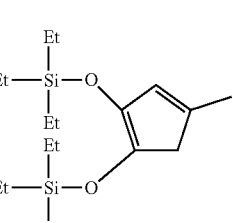 (5-101)
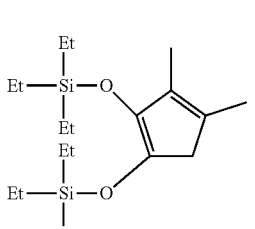 (5-102)
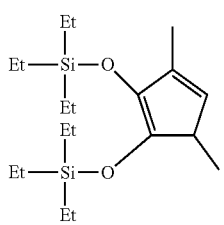 (5-103)
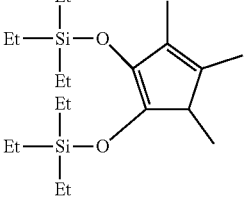 (5-104)
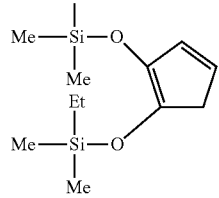 (5-105)
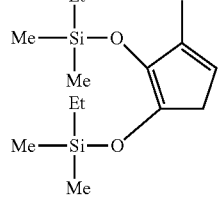 (5-106)
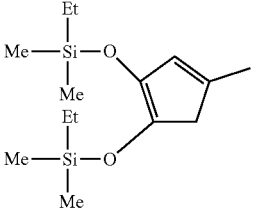 (5-107)
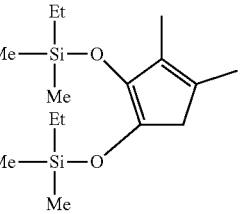 (5-108)
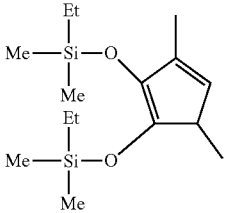 (5-109)

(5-110) 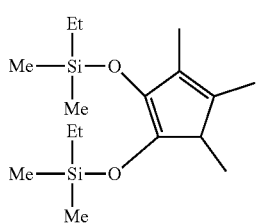
[Formula 35]
(5-111) 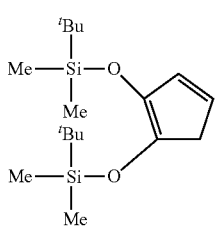
(5-112) 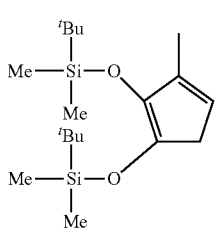
(5-113) 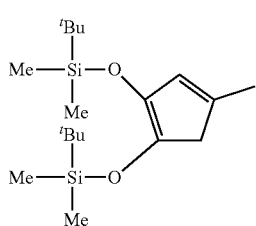
(5-114) 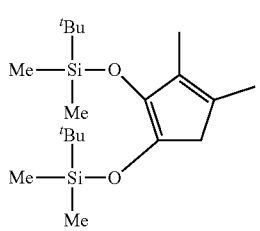
(5-115) 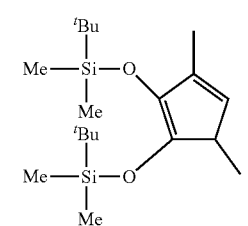
(5-116) 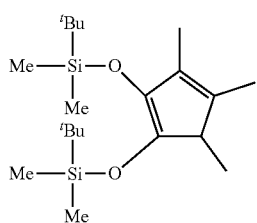
(5-117) 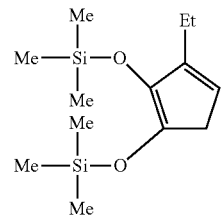
(5-118) 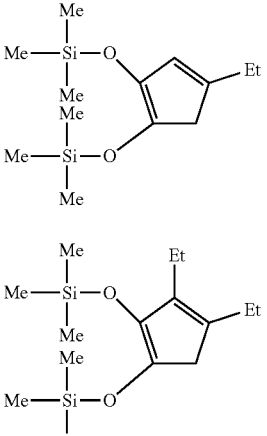
(5-119) 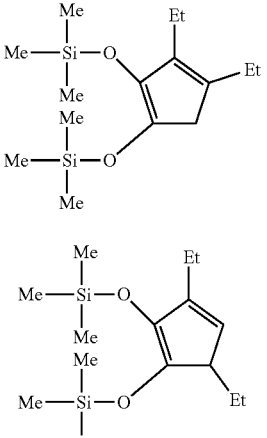
(5-120) 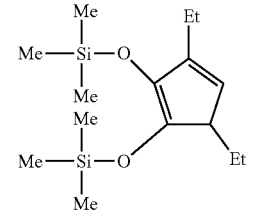
(5-121) 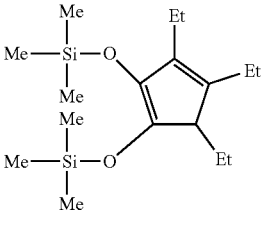
(5-122) 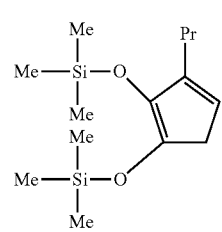

-continued
(5-123)
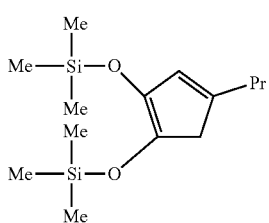
(5-124)
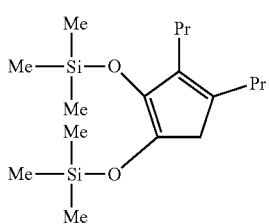
(5-125)
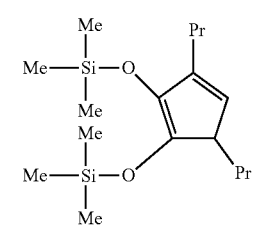
(5-126)
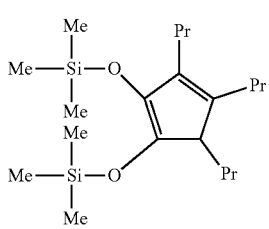
[Formula 36]
(5-127)
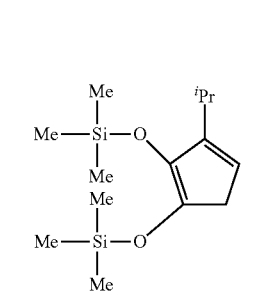
(5-128)
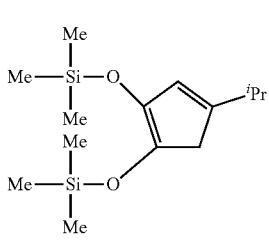
-continued
(5-129)
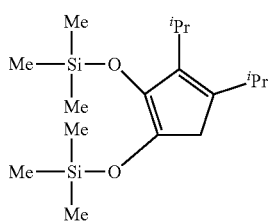
(5-130)
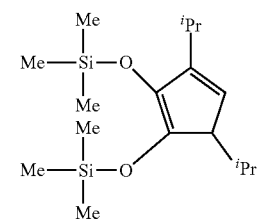
(5-131)
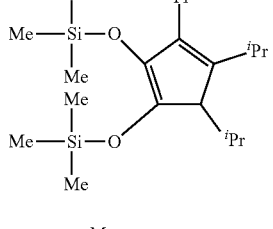
(5-132)
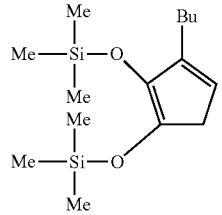
(5-133)
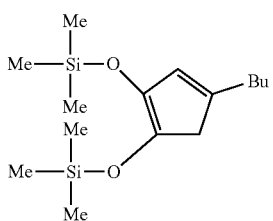
(5-134)
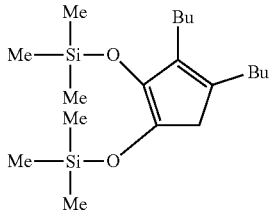
(5-135)
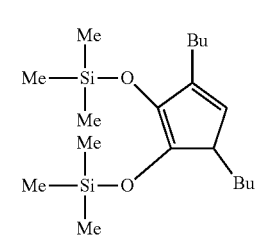

-continued
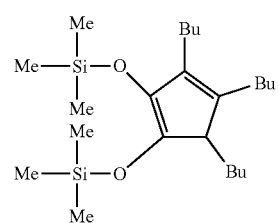
(5-136)
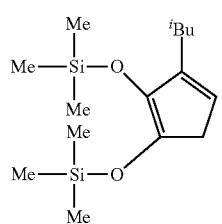
(5-137)
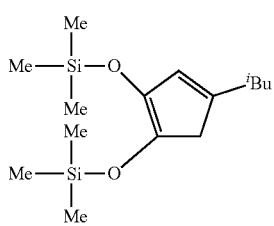
(5-138)
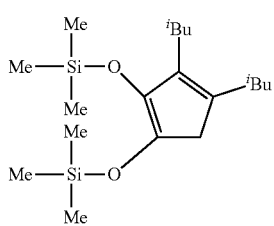
(5-139)
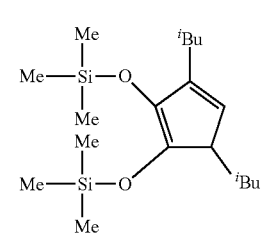
(5-140)
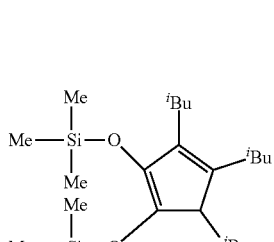
(5-141)
[Formula 37]
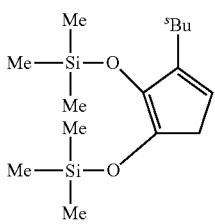
(5-142)
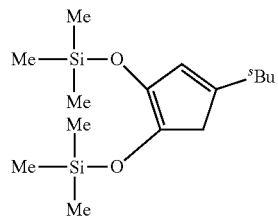
(5-143)
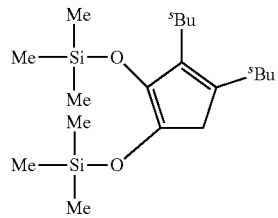
(5-144)
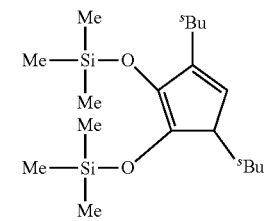
(5-145)
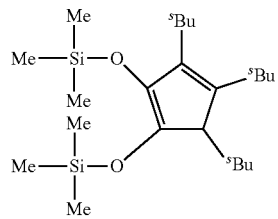
(5-146)
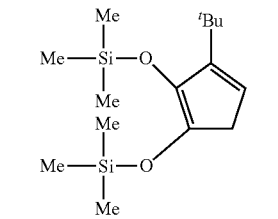
(5-147)
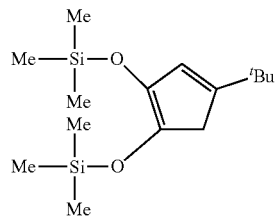
(5-148)

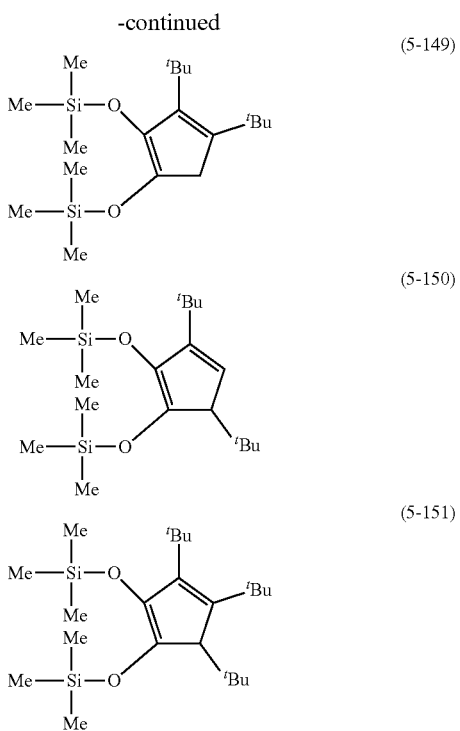

From the viewpoint of obtaining a cobalt complex (1) having vapor pressure and thermal stability suitable for a CVD material or an ALD material, (5-1), (5-2), (5-3), (5-4), (5-5), (5-6), (5-7), (5-8), (5-9), (5-10), (5-11), (5-12), (5-13), (5-14), (5-15), (5-16), (5-17), (5-18), (5-28), (5-29), (5-30), (5-31), (5-32), (5-33), (5-34), (5-35), (5-36), (5-93), (5-94), (5-95), (5-96), (5-97) or (5-98) is preferred, (5-1), (5-2), (5-3), (5-4), (5-5), (5-6), (5-7), (5-8), (5-9), (5-93), (5-94), (5-95), (5-96), (5-97) or (5-98) is more preferred, and (5-1), (5-3), (5-93) or (5-94) is even more preferred.

Examples of lithiating agents that can be used include alkyl lithiums such as methyl lithium, ethyl lithium, propyl lithium and butyl lithium, aryl lithiums such as phenyl lithium and tolyl lithium, and lithium dialkylamides such as lithium dimethylamide, lithium diethylamide and lithium diisopropylamide. From the viewpoint of a high yield, butyl lithium, lithium diethylamide and lithium diisopropylamide are preferred, and lithium diisopropylamide is especially preferred.

From the viewpoint of a high yield of lithium cyclopentadienide (4), the substituted cyclopentadienide (5) and the lithiating agent are preferably reacted in an organic solvent. There are no restrictions on the organic solvents that can be used as long as they do not impair the reaction. Specific examples include aliphatic hydrocarbons such as pentane, hexane, heptane, octane, cyclohexane, methylcyclohexane, ethylcyclohexane and petroleum ether, aromatic hydrocarbons such as benzene, toluene, xylene and ethylbenzene, and ethers such as diethyl ether, diisopropyl ether, dibutyl ether, cyclopentyl methyl ether (CPME), cyclopentylethyl ether (CPEE), tert-butyl methyl ether (MTBE), tetrahydrofuran (THF), dioxane and 1,2-dimethoxyethane. These organic solvents can be used alone or in mixtures of two or more at any ratio.

From the viewpoint of a high yield of lithium cyclopentadienide (4), the substituted cyclopentadienide (5) and the lithiating agent are preferably reacted in an inert gas atmosphere. Specific examples of inert gases include nitrogen, helium, neon, argon, krypton and xenon. Nitrogen or argon is preferred. There are no particular restrictions on the reaction temperature and the reaction time. These can be any reaction temperature and reaction time commonly used by those skilled in the art to produce organic lithium compounds. Specifically, a high yield of lithium cyclopentadienide (4) can be obtained by selecting a reaction temperature in a range from −80° C. to 120° C. and selecting a reaction time in a range from 10 minutes to 120 hours.

A lithium cyclopentadienide (4) obtained by reacting a substituted cyclopentadiene (5) with a lithiating agent can be refined or left unrefined for use as a raw material in Production Method 1. When a lithium cyclopentadienide (4) is refined, it can be refined using a refining method commonly used by those skilled in the art to refine organic lithium compounds. Specific examples of refining methods include filtration, extraction, decantation and crystallization.

From the viewpoint of a high yield of cobalt complex (1), Production Method 1 is preferably carried out in an inert gas atmosphere. Specific examples of inert gases include helium, neon, argon, krypton, xenon and nitrogen gas. Nitrogen gas or argon is preferred from the viewpoint of low cost.

From the viewpoint of a high yield of cobalt complex (1), Production Method 1 is preferably carried out in an organic solvent. There are no restrictions on the organic solvents that can be used as long as they do not impair the reaction. Specific examples include aliphatic hydrocarbons such as pentane, hexane, heptane, octane, cyclohexane, methylcyclohexane, ethylcyclohexane and petroleum ether, aromatic hydrocarbons such as benzene, toluene, xylene, ethylbenzene, propylbenzene, isopropylbenzene, butylbenzene, isobutylbenzene, sec-butylbenzene, tert-butylbenzene, and 1,3,5-trimethylbenzene (mesitylene), and ethers such as diethyl ether, diisopropylether, dibutyl ether, cyclopentyl methyl ether (CPME), cyclopentylethyl ether (CPEE), tert-butyl methyl ether (MTBE), tetrahydrofuran (THF), dioxane and 1,2-dimethoxyethane. These organic solvents can be used alone or in mixtures of two or more at any ratio. From the viewpoint of a high yield of cobalt complex (1), the organic solvent is preferably hexane, heptane, toluene or ether, and more preferably CPME, MTBE, diethyl ether or THF.

There are no particular restrictions on the reaction temperature and the reaction time used in Production Method 1. These can be any reaction temperature and reaction time commonly used by those skilled in the art to produce organic metal complexes. Specifically, a high yield of cobalt complex (1) can be obtained by selecting a reaction temperature in a range from −80° C. to 120° C. and selecting a reaction time in a range from 10 minutes to 120 hours.

There are no particular restrictions on the molar ratios of the trisphosphine complex (3), lithium cyclopentadienide (4) and diene used in Production Method 1. From the viewpoint of a high yield of cobalt complex (1), use of from 0.9 to 1.5 mol. eq. lithium cyclopentadienide (4) and from 1.0 to 10.0 mol. eq. diene per mol. eq. of trisphosphine complex (3) is preferred, and use of from 1.0 to 1.2 mol. eq. lithium cyclopentadienide (4) and from 2.0 to 5.0 mol. eq. diene per mol. eq. of trisphosphine complex (3) is especially preferred.

A cobalt complex (1) obtained using Production Method 1 can be refined using a refining method commonly used by those skilled on the art to refine organic metal compounds. Specific examples of refining methods include filtration, extraction, centrifugation, decantation, distillation, sublimation, crystallization and column chromatography.

An alkyl halogen can be added during the refining step of Production Method 1 to remove phosphine compound byproducts. There are no particular restrictions on the alkyl halide that is used as long as it does not impair the reaction. Examples include methyl chloride, ethyl chloride, propyl chloride, isopropyl chloride, butyl chloride, isobutyl chloride, tert-butyl chloride, methyl bromide, ethyl bromide, propyl bromide, isopropyl bromide, butyl bromide, isobutyl bromide, tert-butyl bromide, methyl iodide, ethyl iodide, propyl iodide, isopropyl iodide, butyl iodide, isobutyl iodide and tert-butyl iodide. From the viewpoint of low cost, methyl iodide or ethyl iodide is preferred. There are no particular restrictions on the amount of alkyl halide used. The amount is preferably from 1.0 to 20.0 mol. eq. and more preferably from 1.0 to 5.0 mol. eq. alkyl halide per mol. eq. of trisphosphine complex (3) from the viewpoint of =a high yield of a cobalt complex (1) of the present invention.

The following is a detailed description of the method used to produce a cobalt-containing thin film using, as a raw material in a vapor phase deposition method based on a chemical reaction, a cobalt complex (1) of the present invention. In the present specification, a vapor phase deposition method based on a chemical reaction means a method for creating a cobalt-containing thin film by decomposing a vaporized cobalt complex (1) on a substrate. Specifically, this method can be a CVD method such as the thermal CVD method, plasma CVD method or photo CVD method, or the ALD method. A CVD method is preferred from the viewpoint of a good film-forming speed and the ALD method is preferred from the viewpoint of a good step coverage. For example, when a cobalt-containing thin film is formed using a CVD method or the ALD method, the cobalt complex (1) can be vaporized and supplied to a reaction chamber, and the cobalt complex (1) can be decomposed on a substrate mounted inside the reaction chamber to form a cobalt-containing thin film on the substrate. The method used to decompose the cobalt complex (1) can be any method commonly used by those skilled in the art to create a metal-containing thin film. Specific examples include reacting the cobalt complex (1) with a reaction gas or applying heat, plasma or light to the cobalt complex (1).

When a reaction gas is used, the reaction gas can be a reducing gas or an oxidizing gas. A reducing gas is preferred as the reaction gas because it can prevent deterioration in the substrate when film is formed on a substrate made from a material susceptible to oxidation such as a metal or metal nitride. Specific examples of reducing gases include ammonia, hydrogen, monosilane, hydrazine, formic acid; a borane-amine complex such as a borane-dimethylamine complex or borane-trimethylamine complex; an unsaturated hydrocarbon having from 4 to 7 carbon atoms such as 1-butene, 2-butene, isobutene, 1-pentene, 2-pentene, 2-methyl-1-butene, 2-methyl-2-butene, 3-methyl-1-butene, 1-hexene, 2-hexene, 3-hexene, 2-methyl-1-pentene, 2-methyl-2-pentene, 4-methyl-2-pentene, 4-methyl-1-pentene, 3-methyl-1-pentene, 3-methyl-2-pentene, 2-ethyl-1-butene, 2,3-dimethyl-1-butene, 2,3-dimethyl-2-butene, 3,3-dimethyl-1-butene, 1,3-butadiene, 1,3-pentadiene, 1,4-pentadiene, isoprene, 1,3-hexadiene, 2,4-hexadiene, 2-methyl-1,3-pentadiene, 3-methyl-1,3-pentadiene, 4-methyl-1,3-pentadiene, 2-ethyl-1,3-butadiene, 3-methyl-1,4-pentadiene or 2,3-dimethyl-1,3-butadiene; or a cyclic unsaturated hydrocarbon having from 6 to 10 carbon atoms such as 1,3-cyclohexadiene, 1,4-cyclohexadiene, 1-methyl-1,3-cyclohexadiene, 2-methyl-1,3-cyclohexadiene, 5-methyl-1,3-cyclohexadiene, 3-methyl-1,4-cyclohexadiene, α-phellandrene, β-phellandrene, α-terpinene, β-terpinene, γ-terpinene or limonene. From the viewpoint of fewer restrictions due to the specifications of the film-forming device and ease of handling, the reducing gas is preferably ammonia, hydrogen, formic acid, 1,3-cyclohexadiene, 1,4-cyclohexadiene, α-terpinene, β-terpinene, γ-terpinene or limonene. When an oxidizing gas is used, specific examples include oxygen, ozone, water vapor, hydrogen peroxide, laughing gas, hydrogen chloride, nitric acid gas and acetate. Oxygen, ozone or water vapor is preferred. The amount of reaction gas used depends on the reactivity of the materials and the capacity of the reaction chamber. When the capacity of the reaction chamber is from 1 to 10 L, there are no particular restrictions on the flow rate of the reaction gas. From an economic viewpoint, a flow rate from 1 to 10,000 sccm is preferred. In the present specification, sccm is the unit used to indicate the flow rate of a gas. When converted to an ideal gas, 1 sccm indicates movement of the gas at a speed of 2.68 mmol/h.

When a cobalt-containing thin film is produced using a CVD method or the ALD method, the cobalt-containing thin film can be produced using any decomposition method. A combination of decomposition methods can also be used. The method used to supply the cobalt complex (1) to the reaction chamber can be any method commonly used by those skilled in the art, including bubbling and liquid vaporization supply systems.

The carrier gas and diluent gas used to produce a cobalt-containing thin film using a CVD method or the ALD method are preferably nitrogen gas or an inert gas such as helium, neon, argon, krypton or xenon. From an economic viewpoint, nitrogen gas or argon is preferred.

The flow rate of the carrier gas and the diluent gas depends on the capacity of the reaction chamber. When the capacity of the reaction chamber is from 1 to 10 L, there are no particular restrictions on the flow rate of the carrier gas, and a flow rate of 1 to 10,000 sccm is preferred from an economic viewpoint.

The substrate temperature when a cobalt-containing thin film is formed using a CVD method or the ALD method depends on whether heat, plasma or light is used and the type of reaction gas being used. For example, when light or plasma is not used and the reaction gas is ammonia or a cyclic unsaturated hydrocarbon, there are no restrictions on the substrate temperature, and a substrate temperature from 200° C. to 1000° C. is preferred from an economic viewpoint. From the viewpoint of a good film forming speed, a substrate temperature from 250° C. to 800° C. is preferred and a substrate temperature from 300° C. to 800° C. is more preferred. When light, plasma, ozone or hydrogen peroxide are used, a cobalt-containing thin film can be produced at a temperature below 200° C.

Examples of a cobalt-containing thin film obtained using the cobalt-containing thin film production method of the present invention include metallic cobalt thin film, cobalt oxide thin film, cobalt nitride thin film, and cobalt oxynitride thin film. After a metallic cobalt thin film has been created, a cobalt-containing composite thin film can be obtained by heat-treating the substrate at a predetermined temperature. For example, when a metallic cobalt thin film has been created on a silicon substrate, a cobalt silicide thin film such as $Co_2Si$, $CoSi$ or $CoSi_2$ can be obtained by performing heat treatment at a temperature from 300° C. to 900° C. When combined with another metal material, a cobalt-containing composite thin film can be obtained. For example, a cobalt silicide thin film can be obtained by combining a cobalt complex (1) of the present invention with a silicon material. Examples of silicon materials include monosilane, disilane, trisilane, tetraethoxysilane, dimethyldimethoxysilane, bis(tert-butylamino)silane, bis(diethylamino)silane and tris(dimethylamino)silane. A cobalt-containing composite thin film can also be obtained by combining a cobalt complex (1) of the present invention with a metal material containing a typical metal such as aluminum or magnesium, a transition metal such as titanium, zirconium, hafnium, niobium, tantalum or tungsten, or a rare earth metal such as lanthanum or neodymium. When a cobalt-containing composite thin film is formed using a CVD method or the ALD method, a cobalt complex (1) of the present invention and another metal material can be supplied separately to the reaction chamber or can be mixed together and then supplied to the reaction chamber.

When a cobalt-containing thin film of the present invention is used as a constituent element, a high-performance semiconductor device can be manufactured with improved reliability and responsiveness. Examples of semiconductor devices include semiconductor memory devices such as DRAM, FeRAM, PRAM, MRAM, ReRAM and flash memory, and field effect transistors. Examples of constituent elements include gate electrodes for transistors, contacts on diffusion layers in source-drain sections, and copper wiring sheet layers/liner layers.

EXAMPLES

The following is a more detailed description of the present invention with reference to examples. The present invention, however, is not limited to these examples. The compounds described in Reference Examples 1-6, Examples 1-7 and Examples 10-15 were all produced in an argon atmosphere. The THF, diethyl ether, dichloromethane and hexane are dehydrated products of Kanto Chemical Co., Ltd.

Reference Example 1

[Formula 38]

8.18 g (85.1 mmol) of 3-methyl-2-cyclopentenone and 9.47 g (93.6 mmol) of triethyl amine were dissolved in 100 mL of hexane, and 18.91 g (85.1 mmol) of trifluoromethanesulfoxy(trimethyl)silane was dropped under ice-cooled conditions. Afterwards, the reaction mixture was stirred for 2 hours at 25° C. The resulting insoluble matter was filtered off using celite and the filtrate was concentrated under reduced pressure. The resulting crude material was distilled under reduced pressure (distillation temperature: 59-60° C., back pressure: $1.1 \times 10^3$ Pa) to obtain 10.97 g of a 1-methyl-3-trimethylsilyloxy-1,3-cyclopentadiene as a colorless liquid. The yield was 77%.

$^1$HNMR (500 MHz, $C_6D_6$, δ/ppm): 6.06 (m, 1H), 5.09 (m, 1H), 2.64 (m, 2H), 1.79 (s, 3H), 0.21 (s, 9H).

Reference Example 2

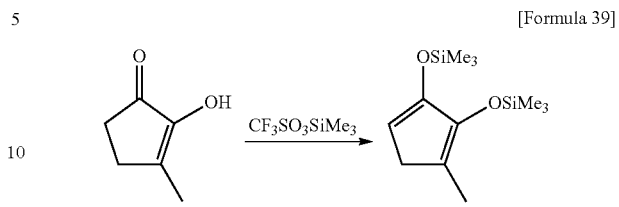

[Formula 39]

6.3 g (56.2 mmol) of 2-hydroxy-3-methyl-2-cyclopentenone and 11.8 g (117.7 mmol) of triethyl amine were dissolved in a mixed solvent of 100 mL hexane and 50 mL of THF, and 25.1 g (112.9 mmol) of trifluoromethanesulfoxy(trimethyl)silane was dropped under ice-cooled conditions. After stirring the reaction mixture for 2 hours at 25° C., the solvent was removed under reduced pressure. The resulting product was distilled under reduced pressure (distillation temperature: 90° C., back pressure: $2.4 \times 10^2$ Pa) to obtain 8.98 g of a 1-methyl-2,3-bis(trimethylsilyloxy)-1,3-cyclopentadiene as a colorless liquid. The yield was 62%.

$^1$HNMR (400 MHz, $CDCl_3$, δ/ppm): 4.85 (t, J=2.1 Hz, 1H), 2.47 (d, J=2.1 Hz, 2H), 1.70 (s, 3H), 0.13 (s, 9H), 0.08 (s, 9H).

Reference Example 3

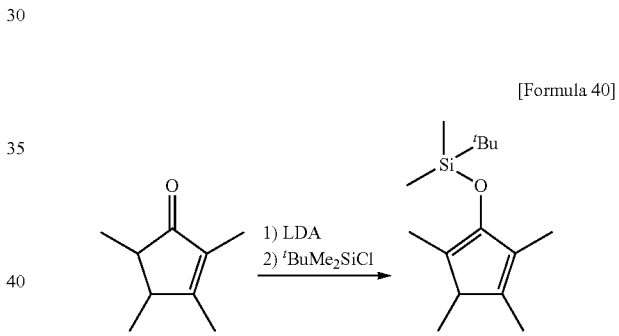

[Formula 40]

A hexane solution of buthyllithium (2.65 M, 60.0 mL) was added to 17.2 g (170 mmol) of diisopropylamine in 40 mL of THF at −70° C., and the reaction mixture was stirred for 15 minutes at 25° C. to prepare a lithium diisopropylamide (LDA) solution. Then, 50 mL of THF and 21.3 g (154 mmol) of 2,3,4,5-tetramethyl-2-cyclopentenone were added to an another vessel the contents were cooled to −70° C., and the lithium diisopropylamide solution was added. The reaction mixture was stirred for 6 hours at 25° C. and concentrated under reduced pressure. Next, 50 mL of THF and 50 mL of hexane were added to the residue, the solution was cooled to −70° C., a hexane (20 mL) solution of 26.4 g (175 mmol) of chloro (tert-butyl) dimethylsilane was added, and the reaction mixture was stirred for 2 hours at 25° C. The resulting insoluble matter was filtered off using celite and the filtrate was concentrated under reduced pressure. The resulting viscous liquid was distilled under reduced pressure (distillation temperature: 72° C., back pressure: $6.0 \times 10^1$ Pa) to obtain 30.4 g of a 1,3,4,5-tetramethyl-2-tert-butyldimethylsilyloxy-1,3-cyclopentadiene as a colorless liquid. The yield was 78%.

$^1$HNMR (500 MHz, $C_6D_6$, δ/ppm): 2.39 (q, J=7.3 Hz, 1H), 1.81 (s, 3H), 1.80 (s, 3H), 1.74 (s, 3H), 1.06 (s, 9H), 0.98 (d, J=7.3 Hz, 3H), 0.15 (s, 6H).

Example 1

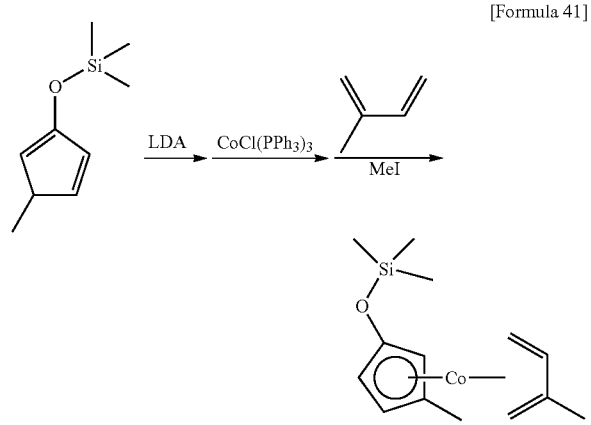

[Formula 41]

30 mL of THF was added to 8.10 g (47.9 mmol) of the 1-methyl-3-trimethylsilyloxy-1,3-cyclopentadiene prepared in Reference Example 1, and then 32 mL (1.5 mol/L, 48.0 mmol) of a THF solution of lithium diisopropylamide was added at 0° C. After stirring the mixture for 1 hour at 25° C., it was added to a suspension prepared by adding 200 mL of toluene to 42.2 g (47.7 mmol) of chlorotris(triphenylphosphine)cobalt. After stirring the mixture for 2 hours, 9.70 g (142 mmol) of 2-methylbuta-1,3-diene was added. After stirring the mixture for 13 hours at 25° C., 36.3 g (256 mmol) of iodomethane was added. After stirring the reaction mixture for 2 hours at 25° C., the solvent was removed under reduced pressure. Next, 200 mL of hexane was added to the remaining oily substance, and the suspension was stirred vigorously at 25° C. After filtering the resulting suspension, the solvent was removed from the filtrate under reduced pressure. The remaining liquid was distilled under reduced pressure (distillation temperature: 120° C., back pressure: 14 Pa) to obtain 5.70 g of ($\eta^5$-3-methyl-1-trimethylsilyloxycyclopentadienyl)($\eta^4$-2-methylbuta-1,3-diene)cobalt as a red liquid (yield: 40%).

$^1$H-NMR (400 MHz, $C_6D_6$, δ/ppm) 4.91 (m, 1H), 4.68 (br, 1H), 4.56 (br, 1H), 4.17 (br, 1H), 2.08 (br, 3H), 1.59 (s, 3H), 1.51 (brs, 2H), 0.15 (s, 9H), 0.01 (br, 2H).

$^{13}$C-NMR (100 MHz, $C_6D_6$, δ/ppm): 93.4, 87.4, 79.1, 74.4, 72.2, 70.4, 38.0, 35.8, 30.5, 22.9, 14.2, 0.16.

Example 2

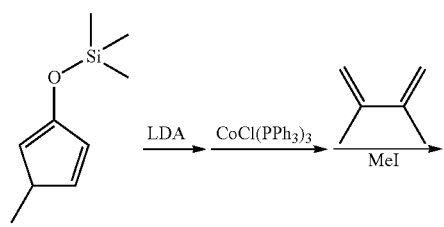

[Formula 42]

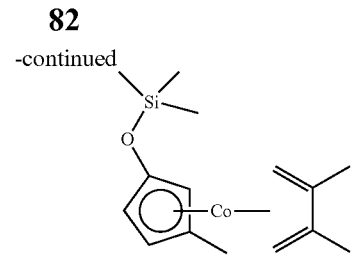

10 mL of THF was added to 1.33 g (7.90 mmol) of the 1-methyl-3-trimethylsilyloxy-1,3-cyclopentadiene prepared in Reference Example 1, and then 5.3 mL (1.5 mol/L, 7.95 mmol) of a THF solution of lithium diisopropylamide was added at 0° C. After stirring the mixture for 1 hour at 25° C., it was added to a suspension prepared by adding 50 mL of toluene to 6.98 g (7.92 mmol) of chlorotris(triphenylphosphine)cobalt. After stirring the mixture for 3 hours, 2.20 g (26.8 mmol) of 2,3-dimethylbuta-1,3-diene was added. After stirring the mixture for 2 hours at 25° C., 4.60 g (32.4 mmol) of iodomethane was added. After stirring the reaction mixture for 15 hours at 25° C., the solvent was removed under reduced pressure. Next, 100 mL of hexane was added to the remaining oily substance, and the suspension was stirred vigorously at 25° C. After filtering the resulting suspension, the solvent was removed from the filtrate under reduced pressure. The remaining liquid was distilled under reduced pressure (distillation temperature: 133° C., back pressure: 41 Pa) to obtain 1.35 g of ($\eta^5$-3-methyl-1-trimethylsilyloxycyclopentadienyl)($\eta^4$-2,3-dimethylbuta-1,3-diene)cobalt as a red liquid (yield: 56%).

$^1$H-NMR (400 MHz, $C_6D_6$, δ/ppm) 4.46 (br, 1H), 4.43 (br, 1H), 4.08 (br, 1H), 2.08 (s, 3H), 2.05 (s, 3H) 1.61 (br, 2H), 1.57 (s, 3H), 0.16 (s, 9H), -0.10 (br, 1H), -0.15 (br, 1H).

$^{13}$C-NMR (100 MHz, $C_6D_6$, δ/ppm): 90.4, 90.3, 86.6, 74.7, 72.5, 70.2, 39.4, 38.2, 30.5, 19.8, 19.7, 13.8, 0.2.

Example 3

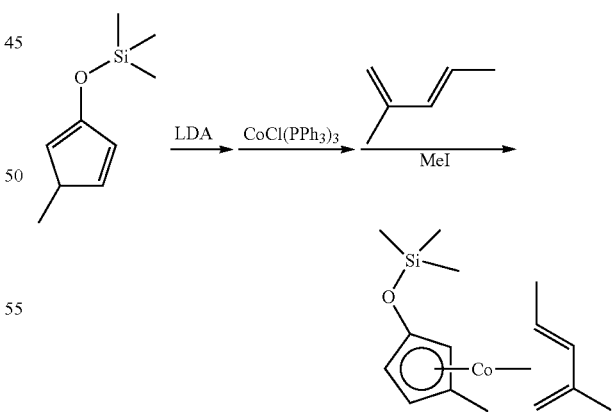

[Formula 43]

30 mL of THF was added to 9.06 g (53.8 mmol) of the 1-methyl-3-trimethylsilyloxy-1,3-cyclopentadiene prepared in Reference Example 1, and then 36.0 mL (1.5 mol/L, 54.0 mmol) of a THF solution of lithium diisopropylamide was added at 0° C. After stirring the mixture for 1 hour at 25° C., it was added to a suspension prepared by adding 200 mL of toluene to 47.5 g (53.9 mmol) of chlorotris(triphenylphosphine)cobalt. After stirring the mixture for 1 hour, 10.6 g (129 mmol) of 2-methylpenta-1,3-diene was added. After stirring the mixture for 17 hours at 25° C., 29.7 g (209 mmol) of iodomethane was added. After stirring the reaction mixture for 3 hours at 25° C., the solvent was removed under reduced pressure. Next, 200 mL of hexane was added to the remaining oily substance, and the suspension was stirred vigorously at 25° C. After filtering the resulting suspension, the solvent was removed from the filtrate under reduced pressure. The remaining liquid was distilled under reduced pressure (distillation temperature: 110° C., back pressure: 19 Pa) to obtain 6.12 g of ($\eta^5$-3-methyl-1-trimethylsilyloxycyclopentadienyl)($\eta^4$-2-methylpenta-1,3-diene)cobalt as a red liquid (yield: 37%).

$^1$H-NMR (400 MHz, C$_6$D$_6$, δ/ppm) 4.44 (br, 1H), 4.34 (br, 1H), 4.03 (br, 1H), 3.43 (br, 1H), 1.83 (s, 3H), 1.37 (br, 3H), 1.25 (br, 1H), 0.94 (br, 3H), 0.15 (br, 1H), −0.05 (s, 9H), −0.33 (br, 1H).

$^{13}$C-NMR (100 MHz, C$_6$D$_6$, δ/ppm): 90.8, 86.8, 83.0, 77.2, 73.7, 72.4, 67.3, 46.8, 38.3, 23.1, 19.0, 14.2, 0.10.

Example 4

[Formula 44]

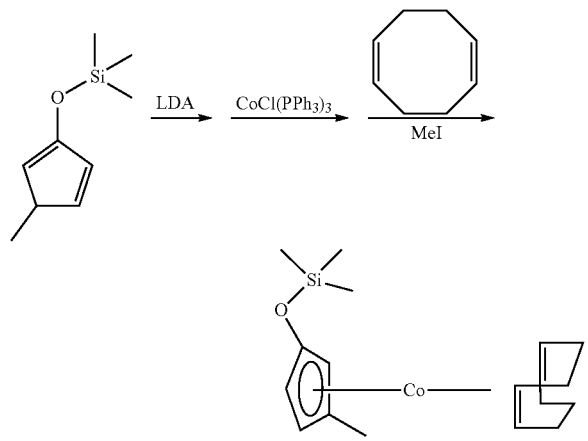

20 mL of THF was added to 1.61 g (9.57 mmol) of the 1-methyl-3-trimethylsilyloxy-1,3-cyclopentadiene prepared in Reference Example 1, and then 6.4 mL (1.5 mol/L, 9.60 mmol) of a THF solution of lithium diisopropylamide was added at 0° C. After stirring the mixture for 1 hour at 25° C., it was added to a suspension prepared by adding 100 mL of toluene to 8.49 g (9.63 mmol) of chlorotris(triphenylphosphine)cobalt. After stirring the mixture for 2 hours, 3.90 g (36.1 mmol) of 1,5-cyclooctadiene was added. After stirring the mixture for 1 hour at 25° C., 6.52 g (45.9 mmol) of iodomethane was added. After stirring the reaction mixture for 15 hours at 25° C., the solvent was removed under reduced pressure. Next, 200 mL of hexane was added to the remaining oily substance, and the suspension was stirred vigorously at 25° C. After filtering the resulting suspension, the solvent was removed from the filtrate under reduced pressure. The remaining liquid was distilled under reduced pressure (distillation temperature: 140° C., back pressure: 5 Pa) to obtain 1.20 g of ($\eta^5$-3-methyl-1-trimethylsilyloxycyclopentadienyl)($\eta^4$-1,5-cyclooctadiene)cobalt as a red liquid (yield: 38%).

$^1$H-NMR (400 MHz, C$_6$D$_6$, δ/ppm) 4.87 (br, 1H), 4.60 (br, 1H), 3.92 (br, 1H), 3.30 (m, 2H), 3.20 (m, 2H), 2.57 (m, 4H), 1.85 (m, 4H), 1.24 (s, 3H), 0.11 (s, 9H).

$^{13}$C-NMR (100 MHz, C$_6$D$_6$, δ/ppm): 88.2, 78.4, 76.0, 74.4, 67.9, 67.1, 32.9, 32.3, 12.4, 0.20.

Example 5

[Formula 45]

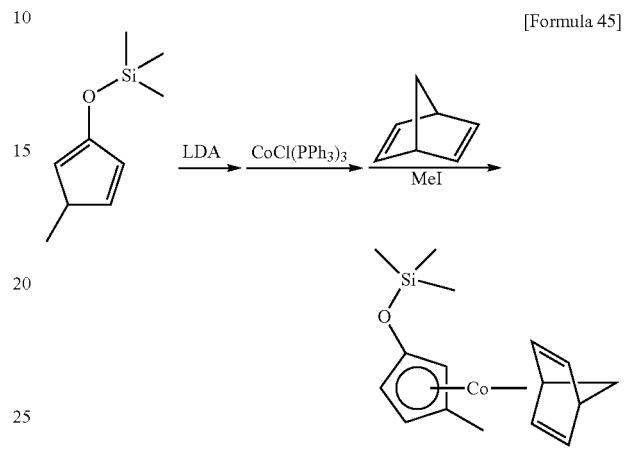

20 mL of THF was added to 2.47 g (14.7 mmol) of the 1-methyl-3-trimethylsilyloxy-1,3-cyclopentadiene prepared in Reference Example 1, and then 9.8 mL (1.5 mol/L, 14.7 mmol) of a THF solution of lithium diisopropylamide was added at 0° C. After stirring the mixture for 1 hour at 25° C., it was added to a suspension prepared by adding 100 mL of toluene to 12.9 g (14.6 mmol) of chlorotris(triphenylphosphine)cobalt. After stirring the mixture for 24 hours, 4.90 g (53.2 mmol) of 2,5-norbornadiene was added. After stirring the mixture for 16 hours at 25° C., 11.9 g (83.8 mmol) of iodomethane was added. After stirring the reaction mixture for 24 hours at 25° C., the solvent was removed under reduced pressure. Next, 200 mL of hexane was added to the remaining oily substance, and the suspension was stirred vigorously at 25° C. After filtering the resulting suspension, the solvent was removed from the filtrate under reduced pressure. The remaining liquid was distilled under reduced pressure (distillation temperature: 100° C., back pressure: 3 Pa) to obtain 1.53 g of ($\eta^5$-3-methyl-1-trimethylsilyloxycyclopentadienyl)($\eta^4$-2,5-norbornadiene)cobalt as a red liquid (yield: 31%).

$^1$H-NMR (400 MHz, C$_6$D$_6$, δ/ppm) 5.15 (br, 1H), 4.57 (br, 1H), 4.33 (br, 1H), 3.30 (br, 2H), 2.64 (s, 4H) 1.18 (s, 3H), 0.95 (br, 2H), 0.10 (s, 9H).

$^{13}$C-NMR (100 MHz, C$_6$D$_6$, δ/ppm): 85.8, 75.8, 74.8, 72.1, 55.0, 44.3, 28.9, 28.5, 12.4, 0.2.

Example 6

[Formula 46]

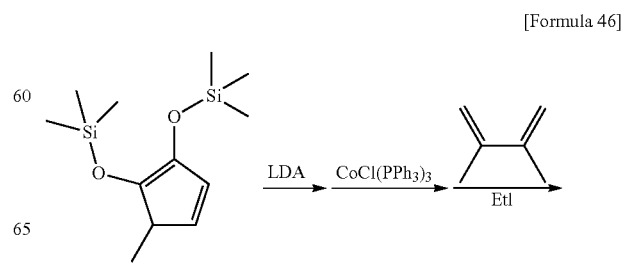

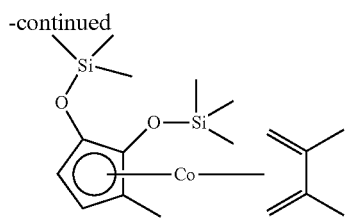

10 mL of THF was added to 2.17 g (8.46 mmol) of the 1-methyl-2,3-bis (trimethylsilyloxy)-1,3-cyclopentadiene prepared in Reference Example 2, and then 5.6 mL (1.5 mol/L, 8.40 mmol) of a THF solution of lithium diisopropylamide was added at 0° C. After stirring the mixture for 1 hour at 25° C., it was added to a suspension prepared by adding 100 mL of toluene to 7.45 g (8.45 mmol) of chlorotris (triphenylphosphine)cobalt. After stirring the mixture for 1 hour, 2.90 g (35.3 mmol) of 2,3-dimethylbuta-1,3-diene was added. After stirring the mixture for 1 hour at 25° C., 6.23 g (39.9 mmol) of iodomethane was added. After stirring the reaction mixture for 14 hours at 25° C., the solvent was removed under reduced pressure. Next, 100 mL of hexane was added to the remaining oily substance, and the suspension was stirred vigorously at 25° C. The resulting suspension was filtered to obtain 2.12 g of ($\eta^5$-1-methyl-2,3-bis (trimethylsilyloxy)cyclopentadienyl)($\eta^4$-2,3-dimethylbuta-1,3-diene)cobalt as a red liquid (yield: 64%).

$^1$H-NMR (400 MHz, $C_6D_6$, δ/ppm) 4.60 (br, 1H), 3.82 (br, 1H), 2.08 (s, 3H), 2.04 (s, 3H), 1.71 (br, 1H), 1.62 (s, 3H), 1.59 (br, 1H), 0.25 (s, 9H), 0.23 (s, 9H), −0.17 (br, 1H), −0.26 (br, 1H).

$^{13}$C-NMR (100 MHz, $C_6D_6$, δ/ppm): 116.5, 113.0, 90.3, 89.7, 77.6, 65.6, 62.2, 40.0, 36.1, 18.6, 17.9, 10.0, 0.99, 0.50.

Example 7

[Formula 47]

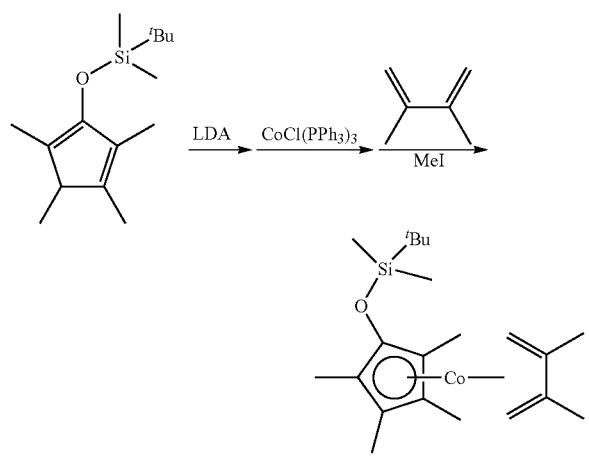

10 mL of THF was added to 2.10 g (8.32 mmol) of the 1,3,4,5-tetramethyl-2-tert-butyldimethylsilyloxy-1,3-cyclopentadiene prepared in Reference Example 3, and then 5.5 mL (1.5 mol/L, 8.25 mmol) of a THF solution of lithium diisopropylamide was added at 0° C. After stirring the mixture for 1 hour at 25° C., it was added to a suspension prepared by adding 100 mL of tolueneto 7.33 g (8.32 mmol) of chlorotris(triphenylphosphine)cobalt. After stirring the mixture for 1 hour, 2.90 g (35.3 mmol) of 2,3-dimethylbuta-1,3-diene was added. After stirring the mixture for 1 hour at 25° C., 6.52 g (45.9 mmol) of iodomethane was added. After stirring the reaction mixture for 14 hours at 25° C., the solvent was removed under reduced pressure. Next, 100 mL of hexane was added to the remaining oily substance, and the suspension was stirred vigorously at 25° C. The resulting suspension was filtered to obtain 2.77 g of ($\eta^5$-1,3,4,5-tetramethyl-2-tert-butyldimethylsilyloxycyclopentadienyl) ($\eta^4$-2,3-dimethylbuta-1,3-diene)cobalt as a red liquid (yield: 85%).

$^1$H-NMR (400 MHz, $C_6D_6$, δ/ppm) 1.92 (s, 6H), 1.81 (s, 6H), 1.79 (s, 6H), 1.22 (br, 2H), 1.01 (s, 9H), 0.05 (s, 6H), −0.33 (br, 2H).

Example 8

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; ammonia gas flow rate: 120 sccm; diluent gas flow rate: 60 sccm; substrate: Ru; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 250° C. Argon was used as the carrier gas and the diluent gas. When the thin film produced in this manner was verified using fluorescent X-ray analysis, characteristic X rays based on cobalt were =detected.

Example 9

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; ammonia gas flow rate: 120 sccm; diluent gas flow rate: 60 sccm; substrate: Ru; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 200° C. Argon was used as the carrier gas and the diluent gas. When the thin film produced in this manner was verified using fluorescent X-ray analysis, characteristic X rays based on cobalt were detected.

Comparative Example 1

A cobalt-containing thin film was produced with the thermal CVD method using bis (ethylcyclopentadienyl)cobalt (Co($\eta^5$-$C_5H_4CH_2CH_3$)$_2$) as the material. A schematic view of the device used to produce the thin film is shown in FIG. 1. The following were the thin film production conditions.

Carrier gas flow rate: 20 sccm; ammonia gas flow rate: 120 sccm; diluent gas flow rate: 60 sccm; substrate: Si; film formation time: 1 hour; reaction chamber pressure: 1.3 kPa; material canister temperature: 48° C.; material vapor pressure: 13.3 Pa; material canister internal pressure: 13.3 kPa; material feed rate: 0.020 sccm; substrate temperature: 250°

C. Argon was used as the carrier gas and the diluent gas. When the thin film produced in this manner was verified using fluorescent X-ray analysis, characteristic X rays based on cobalt were not detected.

It is clear from the results for Example 8, Example 9 and Comparative Example 1 that cobalt complexes (1) of the present invention are materials that can be used to produce a cobalt-containing thin film at a low temperature of 250° C. or less without using an oxidizing gas and without using light or plasma. These materials can be used to form a thin film in a wide range of applications.

Reference Example 4

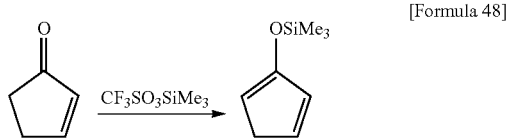

[Formula 48]

4.55 g (55.4 mmol) of 2-cyclopentenone and 6.13 g (60.6 mmol) of triethylamine were dissolved in 30 mL of hexane, and 12.9 g (58.1 mmol) of trifluoromethanesulfoxy (trimethyl)silane was dropped under ice-cooled conditions. Afterwards, the reaction mixture was stirred for 30 minutes at 25° C. The resulting insoluble matter was filtered off using celite and the filtrate was concentrated under reduced pressure. The resulting crude material was distilled under reduced pressure (distillation temperature: 45° C., back pressure: $1.8 \times 10^3$ Pa) to obtain 4.11 g of a 2-trimethylsilyloxy-1,3-cyclopentadiene as a colorless liquid. The yield was 48%.

$^1$H-NMR (400 MHz, $C_6D_6$, δ/ppm): 6.39-6.42 (m, 1H), 6.20-6.22 (m, 1H), 5.22-5.24 (m, 1H), 2.74 (m, 2H), 0.19 (s, 9H).

Reference Example 5

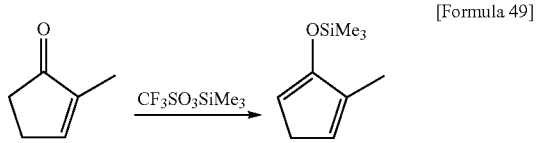

[Formula 49]

6.07 g (63.1 mmol) of 2-methyl-2-cyclopentenone and 7.30 g (72.1 mmol) of triethylamine were dissolved in 50 mL of hexane, and 14.1 g (63.6 mmol) of trifluoromethanesulfoxy(trimethyl)silane was dropped under ice-cooled conditions. Afterwards, the reaction mixture was stirred for 18 hours at 25° C. The resulting insoluble matter was filtered off using celite and the filtrate was concentrated under reduced pressure. The resulting crude material was distilled under reduced pressure (distillation temperature: 51° C., back pressure: $1.8 \times 10^3$ Pa) to obtain 4.37 g of a 2-methyl-3-trimethylsilyloxy-1,3-cyclopentadiene as a colorless liquid. The yield was 41%.

$^1$H-NMR (400 MHz, $C_6D_6$, δ/ppm): 5.95 (m, 1H), 5.20 (m, 1H), 2.72 (m, 2H), 1.96 (brs, 3H), 0.20 (s, 9H).

Reference Example 6

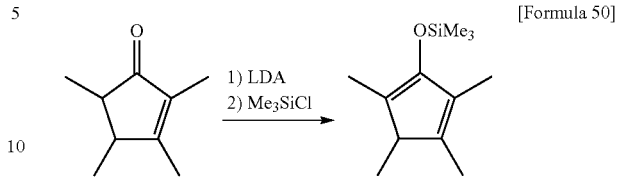

[Formula 50]

50 mL of THF was added to 23.3 g (169 mmol) of 2,3,4,5-tetramethyl-2-cyclopentenone, and 115 ml of a THF solution of lithium diisopropylamide (1.5 mol/L, 173 mmol) was added to the resulting solution at −70° C. The reaction mixture was stirred for 4 hours at 25° C. and concentrated under reduced pressure. Next, 50 mL of THF and 50 mL of hexane were added to the residue, the solution was cooled to −70° C., a hexane (20 mL) solution of 18.9 g (174 mmol) of chlorotrimethylsilane was added, and the reaction mixture was stirred for 15 hours at 25° C. The resulting insoluble matter was filtered off using celite and the filtrate was concentrated under reduced pressure. The resulting viscous liquid wasdistilled under reduced pressure (distillation temperature: 78° C., back pressure: $1.8 \times 10^3$ Pa) to obtain 26.5 g of a 1,2,4,5-tetramethyl-3-trimethylsilyloxy-1,3-cyclopentadiene as a yellow liquid. The yield was 75%.

$^1$H-NMR (400 MHz, $C_6D_6$, δ/ppm): 2.40 (q, J=7.2 Hz, 1H), 1.81 (s, 3H), 1.79 (s, 3H), 1.74 (s, 3H), 0.98 (d, J=7.2 Hz, 3H), 0.20 (s, 9H).

Example 10

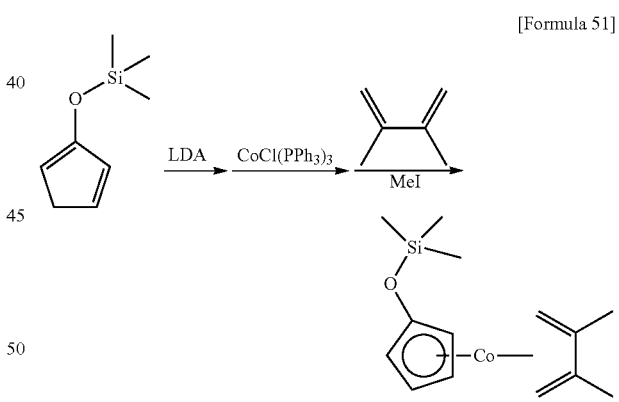

[Formula 51]

10 mL of THF was added to 745 mg (4.82 mmol) of the 2-trimethylsilyloxy-1,3-cyclopentadiene synthesized in Reference Example 4, and then 3.2 mL (1.5 mol/L, 4.80 mmol) of a THF solution of lithium diisopropylamide was added at 0° C. After stirring the mixture for 2 hours at 25° C., it was added to a suspension prepared by mixing 3.78 g (4.28 mmol) of chlorotris(triphenylphosphine)cobalt and 30 mL of toluene. After stirring the mixture for 2 hours at 25° C., 1.09 g (13.3 mmol) of 2,3-dimethylbuta-1,3-diene was added. After stirring the mixture for 2 hours at 25° C., 1.89 g (13.3 mmol) of iodomethane was added and the reaction mixture was stirred for 17 hours at 25° C. The resulting suspension was filtered and the filtrate was concentrated under reduced pressure. The remaining liquid was distilled under reduced pressure (distillation temperature: 72° C., back pressure: 15 Pa) to obtain 209 mg of a ($\eta^5$-trimethylsilyloxycyclopentadienyl) ($\eta^4$-2,3-dimethylbuta-1,3-diene) cobalt as a red liquid (yield: 17%).

$^1$H-NMR (400 MHz, $C_6D_6$, δ): 4.48 (m, 2H), 4.16 (m, 2H), 2.09 (s, 6H), 1.80 (brs, 2H), 0.14 (s, 9H), −0.21 (brs, 2H).

$^{13}$C-NMR (100 MHz, $C_6D_6$, δ): 126.8, 91.3, 74.0, 71.4, 37.1, 20.0, 0.13.

Example 11

[Formula 52]

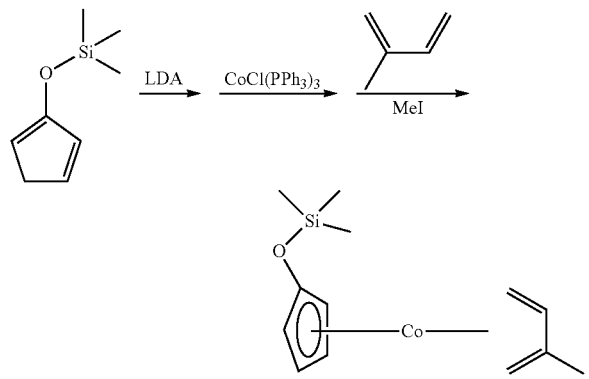

40 mL of THF was added to 10.9 g (71.0 mmol) of the 2-trimethylsilyloxy-1,3-cyclopentadiene synthesized in Reference Example 4, and then 48.0 mL (1.5 mol/L, 72.0 mmol) of a THF solution of lithium diisopropylamide was added at 0° C. After stirring the mixture for 2 hours at 25° C., it was added to a suspension prepared by mixing 63.2 g (71.7 mmol) of chlorotris(triphenylphosphine)cobalt and 500 mL of toluene at 25° C. After stirring the mixture for 2 hours at 25° C., 17.3 g (253 mmol) of 2-methylbuta-1,3-diene was added. After stirring the mixture for 18 hours at 25° C., 30.8 g (217 mmol) of iodomethane was added and the reaction mixture was stirred for 1 hour at 25° C. The resulting suspension was filtered and the filtrate was concentrated under reduced pressure. The remaining liquid was distilled under reduced pressure (distillation temperature: 72° C., back pressure: 62 Pa) to obtain 5.11 g of a ($\eta^5$-trimethylsilyloxycyclopentadienyl) ($\eta^4$-2-methylbuta-1,3-diene) cobalt as a red liquid (yield: 26%).

$^1$H-NMR (400 MHz, $C_6D_6$, δ): 4.97 (m, 1H), 4.73 (m, 1H), 4.52 (m, 1H), 4.17 (m, 1H), 4.05 (m, 1H), 2.08 (s, 3H), 1.83 (br, 1H), 1.72 (br, 1H), 0.14 (s, 9H), −0.07 (br, 1H), −0.17 (br, 1H).

$^{13}$C-NMR (100 MHz, $C_6D_6$, δ): 127.3, 94.1, 78.9, 73.6, 73.0, 71.1, 70.5, 36.5, 33.0, 23.1, 0.09.

Example 12

[Formula 53]

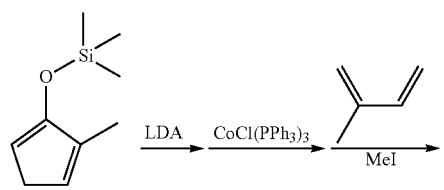

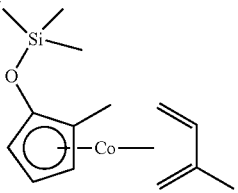

40 mL of THF was added to 4.30 g (25.6 mmol) of the 2-methyl-3-trimethylsilyloxy-1,3-cyclopentadiene synthesized in Reference Example 5, and then 17.0 mL (1.5 mol/L, 25.5 mmol) of a THF solution of lithium diisopropylamide was added at 0° C. After stirring the mixture for 1 hour at 25° C., it was added to a suspension prepared by mixing 22.5 g (25.5 mmol) of chlorotris(triphenylphosphine)cobalt and 200 mL of toluene at 25° C. After stirring the mixture for 2 hours at 25° C., 5.45 g (80.0 mmol) of 2-methylbuta-1,3-diene was added. After stirring the mixture for 1 hour at 25° C., 11.4 g (80.3 mmol) of iodomethane was added and the reaction mixture was stirred for 16 hours at 25° C. The resulting suspension was filtered and the filtrate was concentrated under reduced pressure. The remaining liquid was distilled under reduced pressure (distillation temperature: 69° C., back pressure: 41 Pa) to obtain 2.17 g of a ($\eta^5$-methyl-2-trimethylsilyloxycyclopentadienyl) ($\eta^4$-2-methylbuta-1,3-diene) cobalt as a red liquid (yield: 29%).

$^1$H-NMR (400 MHz, $C_6D_6$, δ): 4.56-4.89 (m, 2H), 4.00-4.24 (m, 2H), 2.02 (s, 3H), 1.79 (br, 1H), 1.72 (brs, 4H), 0.15 (s, 9H), −0.11 (br, 1H), −0.18 (br, 1H).

Example 13

[Formula 54]

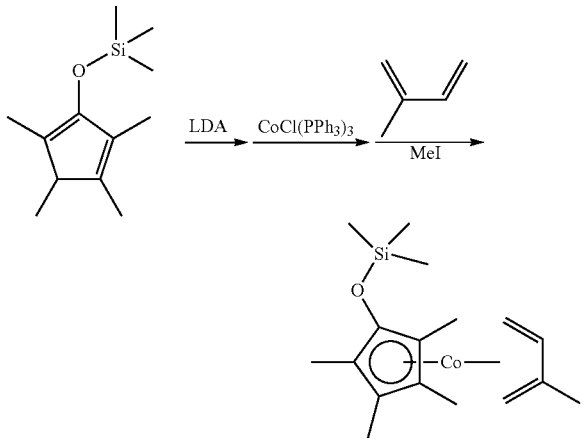

150 mL of THF was added to 26.5 g (126 mmol) of the 1,2,4,5-tetramethyl-3-trimethylsilyloxy-1,3-cyclopentadiene synthesized in Reference Example 6, and then 85.0 mL (1.5 mol/L, 128 mmol) of a THF solution of lithium diisopropylamide was added at 0° C. After stirring the mixture for 1 hour at 25° C., it was added to a suspension prepared by mixing 111 g (126 mmol) of chlorotris(triphenylphosphine) cobalt and 500 mL of toluene at 25° C. After stirring the mixture for 1 hour at 25° C., 34.0 g (500 mmol) of 2-methylbuta-1,3-diene was added. After stirring the mixture for 16 hours at 25° C., 53.6 g (377 mmol) of iodomethane was added and the reaction mixture was stirred for 5 hours at 25° C. The resulting suspension was filtered and the filtrate was concentrated under reduced pressure. The remaining liquid was distilled under reduced pressure (distillation temperature: 82° C., back pressure: 42 Pa) to obtain 4.75 g of a ($\eta^5$-1,2,3,4-tetramethyl-5-trimethylsilyloxycyclopentadienyl)($\eta^4$-2-methylbuta-1,3-diene)cobalt as a red liquid (yield: 11%).

$^1$H-NMR (400 MHz, $C_6D_6$, δ): 4.33 (m, 1H), 1.93 (s, 3H), 1.90 (s, 3H), 1.87 (s, 3H), 1.73 (s, 3H), 1.66 (s, 3H), 1.41 (m, 1H), 1.24 (br, 1H), 0.14 (brs, 9H), −0.16 (m, 1H), −0.23 (br, 1H).

Example 14

[Formula 55]

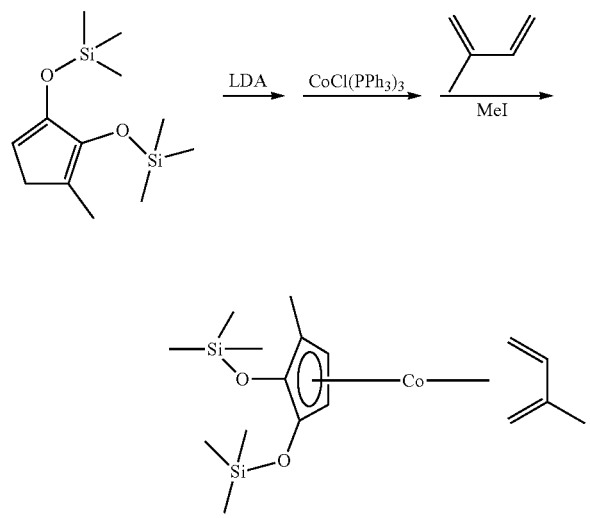

200 mL of THF was added to 19.6 g (76.4 mmol) of the 1-methyl-2,3-bis (trimethylsilyloxy)-1,3-cyclopentadiene synthesized in Reference Example 2, and then 55.0 mL (1.5 mol/L, 82.5 mmol) of a THF solution of lithium diisopropylamide was added at 0° C. After stirring the mixture for 1 hour at 25° C., it was added to a suspension prepared by mixing 67.0 g (76.0 mmol) of chlorotris(triphenylphosphine)cobalt and 500 mL of toluene at 25° C. After stirring the mixture for 2 hours at 25° C., 17.0 g (250 mmol) of 2-methylbuta-1,3-diene was added. After stirring the mixture for 2 hours at 25° C., 34.2 g (241 mmol) of iodomethane was added and the reaction mixture was stirred for 17 hours at 25° C. The resulting suspension was filtered and the filtrate was concentrated under reduced pressure. The remaining liquid was distilled under reduced pressure (distillation temperature: 96° C., back pressure: 26 Pa) to obtain 15.4 g of a [$\eta^5$-1-methyl-2,3-bis(trimethylsilyloxy)cyclopentadienyl]($\eta^4$-2-methylbuta-1,3-diene)cobalt as a red liquid (yield: 53%).

$^1$H-NMR (400 MHz, $C_6D_6$, δ): 4.68 (br, 1H), 4.57 (br, 1H), 3.55 (br, 1H), 2.11 (brs, 3H), 1.79 (br, 1H), 1.74 (br, 1H), 1.70 (brs, 3H), 0.25 (brs, 18H), 0.00 (br, 1H), −0.14 (br, 1H).

Example 15

[Formula 56]

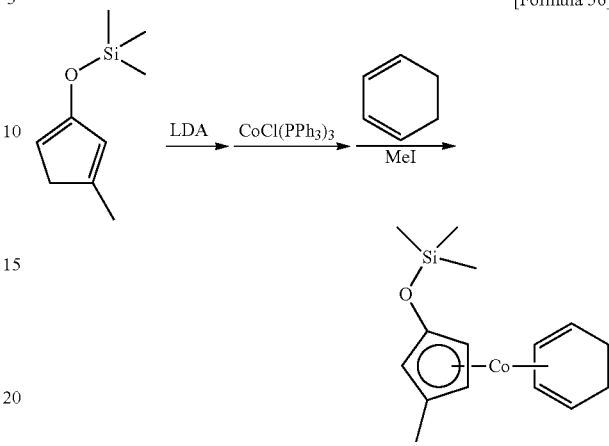

100 mL of THF was added to 17.2 g (102 mmol) of the 1-methyl-3-trimethylsilyloxy-1,3-cyclopentadiene synthesized in Reference Example 1, and then 70 mL (1.5 mol/L, 105 mmol) of a THF solution of lithium diisopropylamide was added at 0° C. After stirring the mixture for 2 hours at 25° C., it was added to a suspension prepared by adding 250 mL of toluene to 91.8 g (104 mmol) of chlorotris(triphenylphosphine)cobalt. After stirring the mixture for 2 hours, 10.7 g (133 mmol) of cyclohexa-1,3-diene was added. After stirring the mixture for 20 hours at 25° C., 45.6 g (321 mmol) of iodomethane was added. After stirring the mixture for 2 hours at 25° C., the solvent was removed under reduced pressure. Next, 250 mL of hexane was added to the remaining oily substance, and the suspension was stirred vigorously at 25° C. After filtering the resulting suspension, the solvent was removed from the filtrate under reduced pressure. The remaining liquid was distilled under reduced pressure (distillation temperature: 92° C., back pressure: 24 Pa) to obtain 8.55 g of ($\eta^5$-1-methyl-3-trimethylsilyloxycyclopentadienyl)($\eta^4$-cyclohexa-1,3-diene)cobalt as a red liquid (yield: 27%).

$^1$H-NMR (400 MHz, $C_6D_6$, δ/ppm) 4.97 (m, 1H), 4.88 (m, 1H), 4.80 (m, 1H), 4.36 (m, 1H), 4.02 (m, 1H), 2.89 (m, 1H), 2.71 (m, 1H), 1.73 (s, 3H), 1.68-1.78 (m, 2H), 1.60-1.95 (m, 2H), 0.15 (s, 9H).

Example 16

A cobalt-containing thin film was produced with the thermal CVD method using the ($\eta^5$-trimethylsilyloxycyclopentadienyl)($\eta^4$-2-methylbuta-1,3-diene)cobalt synthesized in Example 11 as the material. A schematic view of the device used to produce the thin film is shown in FIG. 1. The following were the thin film production conditions.

Carrier gas flow rate: 20 sccm; ammonia gas flow rate: 120 sccm; diluent gas flow rate: 60 sccm; substrate: Ru; film formation time: 1 hour; reaction chamber pressure: 1.3 kPa; material canister temperature: 51° C.; material vapor pressure: 13.3 Pa; material canister internal pressure: 13.3 kPa; material feed rate: 0.02 sccm; substrate temperature: 250° C. Argon was used as the carrier gas and the diluent gas. When the thin film produced in this manner was verified using fluorescent X-ray analysis, characteristic X rays based on cobalt were detected.

Example 17

A cobalt-containing thin film was produced with the thermal CVD method using the ($\eta^5$-trimethylsilyloxycyclopentadienyl)($\eta^4$-2-methylbuta-1,3-diene)cobalt synthesized in Example 11 as the material. A schematic view of the device used to produce the thin film is shown in FIG. 1. The following were the thin film production conditions.

Carrier gas flow rate: 20 sccm; ammonia gas flow rate: 120 sccm; diluent gas flow rate: 60 sccm; substrate: Ir; film formation time: 1 hour; reaction chamber pressure: 1.3 kPa; material canister temperature: 51° C.; material vapor pressure: 13.3 Pa; material canister internal pressure: 13.3 kPa; material feed rate: 0.02 sccm; substrate temperature: 250° C. Argon was used as the carrier gas and the diluent gas. When the thin film produced in this manner was verified using fluorescent X-ray analysis, characteristic X rays based on cobalt were detected.

Example 18

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; 1,3-cyclohexadiene flow rate: 5 sccm; diluent gas flow rate: 25 sccm; substrate: Ru; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 19

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; 1,3-cyclohexadiene flow rate: 5 sccm; diluent gas flow rate: 25 sccm; substrate: Ir; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 20

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; α-terpinene flow rate: 2 sccm; diluent gas flow rate: 28 sccm; substrate: Ru; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 21

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; α-terpinene flow rate: 2 sccm; diluent gas flow rate: 28 sccm; substrate: Ir; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 22

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; limonene flow rate: 3 sccm; diluent gas flow rate: 27 sccm; substrate: Ru; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 325° C. Argon was used as the carrier gas and the diluent gas. When the thin film produced in this manner was verified using fluorescent X-ray analysis, characteristic X rays based on cobalt were detected.

Example 23

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; limonene flow rate: 3 sccm; diluent gas flow rate: 27 sccm; substrate: Ir; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 325° C. Argon was used as the carrier gas and the diluent gas. When the thin film produced in this manner was verified using fluorescent X-ray analysis, characteristic X rays based on cobalt were detected.

Example 24

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; ammonia gas flow rate: 5 sccm; 1,3-cyclohexadiene flow rate: 5 sccm; diluent gas flow rate: 20 sccm; substrate: Ru; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 25

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; ammonia gas flow rate: 5 sccm; 1,3-cyclohexadiene flow rate: 5 sccm; diluent gas flow rate: 20 sccm; substrate: Ir; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 26

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; ammonia gas flow rate: 10 sccm; α-terpinene flow rate: 2 sccm; diluent gas flow rate: 18 sccm; substrate: Ru; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 27

A cobalt-containing thin film was produced with the thermal CVD method using the ($\eta^5$-3-methyl-1-trimethylsilyloxycyclopentadienyl)($\eta^4$-2-methylbuta-1,3-diene)cobalt synthesized in Example 1 as the material. A schematic view of the device used to produce the thin film is shown in FIG. 1. The following were the thin film production conditions.

Carrier gas flow rate: 20 sccm; ammonia gas flow rate: 10 sccm; α-terpinene flow rate: 2 sccm; diluent gas flow rate: 18 sccm; substrate: Ir; film formation time: 1 hour; reaction chamber pressure: 1.3 kPa; material canister temperature: 63° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 28

A cobalt-containing thin film was produced with the thermal CVD method using the [$\eta^5$-1-methyl-2,3-bis(trimethylsilyloxy)cyclopentadienyl] ($\eta^4$-2-methylbuta-1,3-diene)cobalt synthesized in Example 14 as the material. A schematic view of the device used to produce the thin film is shown in FIG. 1. The following were the thin film production conditions.

Carrier gas flow rate: 20 sccm; 1,3-cyclohexadiene flow rate: 7.5 sccm; diluent gas flow rate: 30 sccm; substrate: Ru; film formation time: 1 hour; reaction chamber pressure: 1.3 kPa; material canister temperature: 84° C.; material vapor pressure: 54.8 Pa; material canister internal pressure: 6.7 kPa; material feed rate: 0.17 sccm; substrate temperature: 300° C. Argon was used as the carrier gas and the diluent gas. When the thin film produced in this manner was verified using fluorescent X-ray analysis, characteristic X rays based on cobalt were detected.

Example 29

A cobalt-containing thin film was produced with the thermal CVD method using the [$\eta^5$-1-methyl-2,3-bis(trimethylsilyloxy)cyclopentadienyl] ($\eta^4$-2-methylbuta-1,3-diene)cobalt synthesized in Example 14 as the material. A schematic view of the device used to produce the thin film is shown in FIG. 1. The following were the thin film production conditions.

Carrier gas flow rate: 20 sccm; 1,3-cyclohexadiene flow rate: 7.5 sccm; diluent gas flow rate: 30 sccm; substrate: Ir; film formation time: 1 hour; reaction chamber pressure: 1.3 kPa; material canister temperature: 84° C.; material vapor pressure: 54.8 Pa; material canister internal pressure: 6.7 kPa; material feed rate: 0.17 sccm; substrate temperature: 300° C. Argon was used as the carrier gas and the diluent gas. When the thin film produced in this manner was verified using fluorescent X-ray analysis, characteristic X rays based on cobalt were detected.

Example 30

A cobalt-containing thin film was produced with the thermal CVD method using the ($\eta^5$-1-methyl-3-trimethylsilyloxycyclopentadienyl)($\eta^4$-cyclohexa-1,3-diene)cobalt synthesized in Example 15 as the material. A schematic view of the device used to produce the thin film is shown in FIG. 1. The following were the thin film production conditions.

Carrier gas flow rate: 20 sccm; 1,3-cyclohexadiene flow rate: 7.5 sccm; diluent gas flow rate: 30 sccm; substrate: Ru; film formation time: 1 hour; reaction chamber pressure: 1.3 kPa; material canister temperature: 80° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 31

A cobalt-containing thin film was produced with the thermal CVD method using the ($\eta^5$-1-methyl-3-trimethylsilyloxycyclopentadienyl)(η⁴-cyclohexa-1,3-diene)cobalt synthesized in Example 15 as the material. A schematic view of the device used to produce the thin film is shown in FIG. 1. The following were the thin film production conditions.

Carrier gas flow rate: 20 sccm; 1,3-cyclohexadiene flow rate: 7.5 sccm; diluent gas flow rate: 30 sccm; substrate: Ir; film formation time: 1 hour; reaction chamber pressure: 1.3 kPa; material canister temperature: 80° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 32

A cobalt-containing thin film was produced with the thermal CVD method using the (η⁵-1-methyl-3-trimethylsilyloxycyclopentadienyl)(η⁴-cyclohexa-1,3-diene)cobalt synthesized in Example 15 as the material. A schematic view of the device used to produce the thin film is shown in FIG. 1. The following were the thin film production conditions.

Carrier gas flow rate: 20 sccm; ammonia gas flow rate: 5 sccm; 1,3-cyclohexadiene flow rate: 6 sccm; diluent gas flow rate: 25 sccm; substrate: Ru; film formation time: 1 hour; reaction chamber pressure: 1.3 kPa; material canister temperature: 80° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

Example 33

A cobalt-containing thin film was produced with the thermal CVD method using the (η⁵-1-methyl-3-trimethylsilyloxycyclopentadienyl)(η⁴-cyclohexa-1,3-diene)cobalt synthesized in Example 15 as the material. A schematic view of the device used to produce the thin film is shown in FIG. 1. The following were the thin film production conditions.

Carrier gas flow rate: 20 sccm; ammonia gas flow rate: 5 sccm; 1,3-cyclohexadiene flow rate: 6 sccm; diluent gas flow rate: 25 sccm; substrate: Ir; film formation time: 1 hour; reaction chamber pressure: 1.3 kPa; material canistertemperature: 80° C.; material vapor pressure: 13.3 Pa; material canister internal pressure: 13.3 kPa; material feed rate: 0.02 sccm; substrate temperature: 300° C. Argon was used as the carrier gas and the diluent gas. When the thin film produced in this manner was verified using fluorescent X-ray analysis, characteristic X rays based on cobalt were detected.

It is clear from the results for Examples 16-33 that cobalt complexes (1) of the present invention are materials that can be used to produce a cobalt-containing thin film without using an oxidizing gas and without using light or plasma.

KEY TO THE DRAWINGS

1: Material canister
2: Constant temperature bath
3: Reaction chamber
4: Substrate
5: Reaction gas inlet
6: Dilution gas inlet
7: Carrier gas inlet
8: Mass flow controller
9: Mass Flow Controller
10: Mass flow controller
11: Oil rotary pump
12: Exhaust The present invention was described above in detail with reference to specific embodiments, but it should be clear to those skilled in the art that various changes and modifications are possible without departing from the spirit and scope of the present invention.

The invention claimed is:
1. A cobalt complex represented by Formula (1)

[Formula 1]

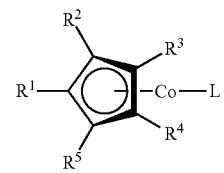

(1)

where $R^1$ is a silyloxy group represented by Formula (2)

[Formula 2]

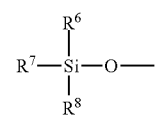

(2)

where $R^6$, $R^7$ and $R^8$ each independently represent an alkyl group having from 1 to 6 carbon atoms; $R^2$ is a hydrogen atom, an alkyl group having from 1 to 6 carbon atoms, or a silyloxy group represented by Formula (2); $R^3$, $R^4$ and $R^5$ each independently represent a hydrogen atom or an alkyl group having from 1 to 6 carbon atoms; and L is a diene having from 4 to 10 carbon atoms].

2. A cobalt complex according to claim 1, wherein $R^3$, $R^4$ and $R^5$ are each independently a hydrogen atom or a methyl group.

3. A cobalt complex according to claim 1, wherein $R^6$, $R^7$ and $R^8$ are each independently an alkyl group having from 1 to 4 carbon atoms.

4. A method for producing a cobalt complex according to claim 1, the method comprising the steps of: reacting a trisphosphine complex represented by Formula (3)

[Formula 3]

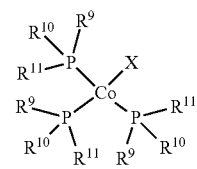

(3)

where $R^9$, $R^{10}$ and $R^{11}$ are each independently a phenyl group, a tolyl group, an alkyl group having from 1 to 6 carbon atoms, or an alkyloxy group having from 1 to 6 carbon atoms; and X is a halogen atom with a lithium cyclopentadienide represented by Formula (4)

[Formula 4]

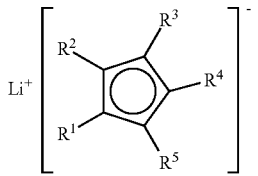

(4)

where $R^1$, $R^2$, $R^3$, $R^4$ and $R^5$ are the same as $R^1$, $R^2$, $R^3$, $R^4$ and $R^5$ in Formula (1); and reacting the product with a diene having from 4 to 10 carbon atoms.

5. A method for producing a cobalt-containing thin film using, as a raw material in a vapor phase deposition method based on a chemical reaction, a cobalt complex represented by Formula (1)

[Formula 1]

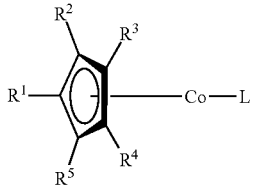

(1)

[where $R^1$ is a silyloxy group represented by Formula (2)

[Formula 2]

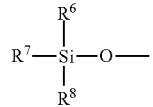

(2)

where $R^6$, $R^7$ and $R^8$ each independently represent an alkyl group having from 1 to 6 carbon atoms; $R^2$ is a hydrogen atom, an alkyl group having from 1 to 6 carbon atoms, or a silyloxy group represented by Formula (2); $R^3$, $R^4$ and $R^5$ each independently represent a hydrogen atom or an alkyl group having from 1 to 6 carbon atoms; and L is a diene having from 4 to 10 carbon atoms].

6. A method for producing a cobalt-containing thin film according to claim 5, wherein the vapor phase deposition method based on a chemical reaction is the chemical vapor phase deposition method.

7. A method for producing a cobalt-containing thin film according to claim 5, wherein a decomposition gas is used in the vapor phase deposition method based on a chemical reaction.

8. A method for producing a cobalt-containing thin film according to claim 7, wherein a reductive gas is used as the decomposition gas.

9. A method for producing a cobalt-containing thin film according claim 5, wherein the cobalt-containing thin film is a metal cobalt thin film.

10. A cobalt-containing thin film produced using a method for producing a cobalt-containing thin film according to claim 5.

11. A semiconductor device using a cobalt-containing thin film according to claim 10 as at least one of a transistor gate electrode, a contact on a diffusion layer in a source-drain section, and a copper wiring sheet layer/liner layer.

\* \* \* \* \*